United States Patent
Pauls et al.

(10) Patent No.: US 8,895,545 B2
(45) Date of Patent: *Nov. 25, 2014

(54) ACRYLAMIDE DERIVATIVES AS FAB I INHIBITORS

(71) Applicant: Affinium Pharmaceuticals, Inc., Toronto (CA)

(72) Inventors: Heinz W. Pauls, Oakville (CA); Jailall Ramnauth, Brampton (CA); Peter Sampson, Oakville (CA); Andras Toro, Oxnard, CA (US)

(73) Assignee: Debiopharm International SA, Lausanne (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/644,351

(22) Filed: Oct. 4, 2012

(65) Prior Publication Data

US 2013/0237523 A1   Sep. 12, 2013

Related U.S. Application Data

(63) Continuation of application No. 12/374,444, filed as application No. PCT/CA2007/001277 on Jul. 19, 2007, now Pat. No. 8,318,720.

(60) Provisional application No. 60/832,058, filed on Jul. 20, 2006.

(51) Int. Cl.
| | |
|---|---|
| *C07D 471/04* | (2006.01) |
| *C07D 405/12* | (2006.01) |
| *C07D 409/12* | (2006.01) |
| *C07D 213/73* | (2006.01) |
| *C07D 401/12* | (2006.01) |
| *C07D 495/04* | (2006.01) |
| *A61K 31/4427* | (2006.01) |
| *A61P 31/04* | (2006.01) |
| *C07D 498/04* | (2006.01) |
| *A01N 43/90* | (2006.01) |

(52) U.S. Cl.
CPC ............ *C07D 471/04* (2013.01); *C07D 498/04* (2013.01); *A01N 43/90* (2013.01)
USPC .............. 514/211.06; 514/211.1; 514/212.07; 514/214.02; 514/220; 514/221; 540/491; 540/501; 540/552; 540/567; 540/569

(58) Field of Classification Search
USPC ......................... 540/491, 501, 552, 567, 569; 514/211.06, 211.1, 212.07, 214.02, 514/220, 221
See application file for complete search history.

(56) References Cited

U.S. PATENT DOCUMENTS

| | | | |
|---|---|---|---|
| 3,828,068 | A | 8/1974 | Minieri |
| 4,154,943 | A | 5/1979 | Kuehne |
| 4,977,159 | A | 12/1990 | Sevrin et al. |
| 5,416,193 | A | 5/1995 | Desai |
| 5,614,551 | A | 3/1997 | Dick et al. |
| 5,624,941 | A | 4/1997 | Barth et al. |
| 5,932,743 | A | 8/1999 | Collini et al. |
| 5,985,867 | A | 11/1999 | Rodgers et al. |
| 5,989,832 | A | 11/1999 | Trias et al. |
| 6,133,260 | A | 10/2000 | Matzke et al. |
| 6,174,878 | B1 | 1/2001 | Gamache et al. |
| 6,184,380 | B1 | 2/2001 | Chiu et al. |
| 6,187,341 | B1 | 2/2001 | Johnson et al. |
| 6,194,429 | B1 | 2/2001 | Guinn et al. |
| 6,194,441 | B1 | 2/2001 | Roberts et al. |
| 6,198,000 | B1 | 3/2001 | Hawkins |
| 6,221,859 | B1 | 4/2001 | Dorso et al. |
| 6,221,864 | B1 | 4/2001 | Hirayama et al. |
| 6,235,908 | B1 | 5/2001 | Fey |
| 6,239,113 | B1 | 5/2001 | Dawson et al. |
| 6,239,141 | B1 | 5/2001 | Allen et al. |
| 6,248,363 | B1 | 6/2001 | Patel et al. |
| 6,267,985 | B1 | 7/2001 | Chen et al. |
| 6,277,836 | B1 | 8/2001 | Borody |
| 6,288,239 | B1 | 9/2001 | Hollingsworth et al. |
| 6,291,462 | B1 | 9/2001 | Bartholomaeus et al. |
| 6,294,192 | B1 | 9/2001 | Patel et al. |
| 6,303,572 | B1 | 10/2001 | Rowe |
| 6,309,663 | B1 | 10/2001 | Patel et al. |
| 6,333,045 | B1 | 12/2001 | Yasueda et al. |
| 6,340,689 | B1 | 1/2002 | Dubois et al. |
| 6,346,391 | B1 | 2/2002 | Oethinger et al. |
| 6,367,985 | B1 | 4/2002 | Lee et al. |
| 6,372,752 | B1 | 4/2002 | Staveski et al. |
| 6,388,070 | B1 | 5/2002 | Deshpande et al. |
| 6,395,746 | B1 | 5/2002 | Cagle et al. |
| 6,399,629 | B1 | 6/2002 | Chamberland et al. |
| 6,406,880 | B1 | 6/2002 | Thornton |
| 6,423,341 | B1 | 7/2002 | Yamaguchi |

(Continued)

FOREIGN PATENT DOCUMENTS

| | | |
|---|---|---|
| CA | 2444597 A1 | 10/2002 |
| CA | 2568914 A1 | 12/2005 |
| CA | 2776849 A1 | 5/2011 |
| CN | 102675311 A | 9/2012 |
| EP | 0407200 A1 | 1/1991 |
| EP | 0953570 A1 | 11/1999 |

(Continued)

OTHER PUBLICATIONS

Abou-Gharbia et al., "Psychotropic Agents: Synthesis and Antipsychotic Activity of Substituted B-Carbolines," *J. Med. Chem.*, 30(6):1100-1105 (1987).

(Continued)

*Primary Examiner* — Bruck Kifle
(74) *Attorney, Agent, or Firm* — Goodwin Procter LLP

(57) ABSTRACT

In part, the present invention is directed to antibacterial compounds.

20 Claims, 2 Drawing Sheets

(56) References Cited

U.S. PATENT DOCUMENTS

| | | |
|---|---|---|
| 6,423,741 B1 | 7/2002 | Khanuja et al. |
| 6,428,579 B1 | 8/2002 | Valentini |
| 6,432,444 B1 | 8/2002 | Fischetti et al. |
| 6,432,670 B1 | 8/2002 | Payne et al. |
| 6,436,980 B1 | 8/2002 | Leger et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf et al. |
| 6,846,819 B1 | 1/2005 | Miller et al. |
| 6,951,729 B1 | 10/2005 | DeWolf et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,449,458 B2 | 11/2008 | Bhamidipati et al. |
| 7,524,843 B2 | 4/2009 | Miller et al. |
| 7,538,108 B2 | 5/2009 | Singh et al. |
| 7,557,125 B2 | 7/2009 | Miller et al. |
| 7,563,892 B1 | 7/2009 | Singh et al. |
| 7,741,339 B2 | 6/2010 | Burgess et al. |
| 7,790,709 B2 | 9/2010 | Berman et al. |
| 7,790,716 B2 | 9/2010 | Miller et al. |
| 7,879,872 B2 | 2/2011 | Berman et al. |
| 7,989,448 B2 | 8/2011 | Singh et al. |
| 8,153,652 B2 | 4/2012 | Burgess et al. |
| 8,163,902 B2 | 4/2012 | Bhamidipati et al. |
| 8,173,646 B2 | 5/2012 | Miller et al. |
| 8,211,888 B2 | 7/2012 | Singh et al. |
| 8,211,889 B2 | 7/2012 | Singh et al. |
| 8,263,613 B2 | 9/2012 | Pauls et al. |
| 8,318,720 B2 | 11/2012 | Pauls et al. |
| 8,450,307 B2 | 5/2013 | Sargent et al. |
| 2001/0016662 A1 | 8/2001 | Golik et al. |
| 2003/0232850 A1 | 12/2003 | Miller et al. |
| 2004/0053814 A1 | 3/2004 | Brandt et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2006/0211657 A1 | 9/2006 | Singh et al. |
| 2006/0234983 A1 | 10/2006 | Singh et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |
| 2010/0130470 A1 | 5/2010 | Pauls et al. |
| 2011/0124633 A1 | 5/2011 | Berman et al. |
| 2012/0010127 A1 | 1/2012 | Berman et al. |
| 2013/0237523 A1 | 9/2013 | Pauls et al. |
| 2013/0281442 A1 | 10/2013 | Hafkin |
| 2014/0051666 A1 | 2/2014 | Partridge et al. |
| 2014/0107106 A1 | 4/2014 | Sargent et al. |

FOREIGN PATENT DOCUMENTS

| | | | |
|---|---|---|---|
| EP | | 1000935 A1 | 5/2000 |
| HU | | 210679 A2 | 7/1993 |
| HU | | 0203122 A2 | 1/2003 |
| WO | WO-93/04035 A1 | | 3/1993 |
| WO | WO-95/18619 A1 | | 7/1995 |
| WO | WO-96/00730 A1 | | 1/1996 |
| WO | WO-97/48696 A1 | | 12/1997 |
| WO | WO-98/57952 A1 | | 12/1998 |
| WO | WO-99/24406 A1 | | 5/1999 |
| WO | WO-00/27628 A1 | | 5/2000 |
| WO | WO-00/57933 A1 | | 10/2000 |
| WO | WO-01/26652 A1 | | 4/2001 |
| WO | WO-01/26654 A1 | | 4/2001 |
| WO | WO-01/27103 A1 | | 4/2001 |
| WO | WO-01/41573 A1 | | 6/2001 |
| WO | WO-01/48248 A2 | | 7/2001 |
| WO | WO-01/70172 A2 | | 9/2001 |
| WO | WO-02/10332 A1 | | 2/2002 |
| WO | WO-02/42273 A2 | | 5/2002 |
| WO | WO-02/48097 A1 | | 6/2002 |
| WO | WO-02/064572 A1 | | 8/2002 |
| WO | WO-03/086396 A1 | | 10/2003 |
| WO | WO-03/088897 A2 | | 10/2003 |
| WO | WO-2004/014869 A2 | | 2/2004 |
| WO | WO-2004/052890 A1 | | 6/2004 |
| WO | WO-2004/082586 A2 | | 9/2004 |
| WO | WO-2005/090367 A1 | | 9/2005 |
| WO | WO-2007/053131 A2 | | 5/2007 |
| WO | WO-2007/067416 A2 | | 6/2007 |
| WO | WO-2008/009122 A1 | | 1/2008 |
| WO | WO-2008/064274 A1 | | 5/2008 |
| WO | WO-2008/098374 A1 | | 8/2008 |
| WO | WO-2009/003136 A1 | | 12/2008 |
| WO | WO-2011/002999 A1 | | 1/2011 |
| WO | WO-2011/061214 A1 | | 5/2011 |
| WO | WO-2011/156811 A2 | | 12/2011 |
| WO | WO-2013/190384 A1 | | 12/2013 |

OTHER PUBLICATIONS

Ahsan et al., "Reserpine Analogues: Synthesis of β-Carboline Derivatives," *J. Chem.Soc.*, pp. 3928-3920 (1963).

Annesley et al "Glucuronidation of prodrug reactive site: isolation and characterization of oxymethylglucuronide metabolite of fosphenytoin" *Clin Chem*. May 2001;47(5):910-8.

(56) References Cited

OTHER PUBLICATIONS

Barkema et al., "Invited Review: The Role of Cow, Pathogen, and Treatment Regimen in the Therapeutic Success of Bovine *Staphylococcus aureus* Mastitis," *Journal Dairy Science*, 89:1877-1895 (2006).
Bergler et al., "Protein EnvM is the NADH-dependent Enoyl-ACP Reductase (FabI) of *Escherichia coli*," *J. Biological Chemistry*, 269(8):5493-5496 (1994).
Claus et al., "Formaldehydabspaltende Phenolcarbonsaurederivate" *Mh. Chem.* 97:271-279 (1966).
Database CA on STN, AN 7:66733, Rosenmund et al., *Chem Ber.* 103(2): 496-509 (1970).
Database CAOLD on STN, AN CA51:10524d, Hellman et al. (1953).
Database CAPLUS on STN, AN 1977:439214. Misztal et al. *Arch Immuno Ther Exp.* 24(6):851-862 (1976).
Database CAPLUS on STN, AN 1986:68547, Stuetz, et al., *J. Med Chem.*, 29(1): 112-25 (1986).
Database CAPLUS on STN, AN 1991:428908, Fuse et al., EP407200A1 (1991).
Database CAPLUS on STN, AN 1999;325910 Aslanian , et al., WO99/24406. (1999).
Database Crossfire Beilstein, 1966, Database accession No. 2819049, 2819050, XP002216033.
Ettmayer et al., "Lessons learned from marketed and investigational prodrugs", J Med Chem, 47(10):2393-2404 (2004).
European Search Report for EP 11 793 310.1 mailed Oct. 30, 2013, 9 pages.
Grassberger et al., "Preparation and Antibacterial Activities of New 1,2,3-Diazaborine Derivatives and Analogues," *J. Med. Chemistry*, 27:947-953 (1984).
Heath et al., "A Triclosan-Resistant Bacterial Enzyme," *Nature*, 406:145-146 (2000).
Heath et al., "Regulation of Fatty Acid Elongation and Initiation by Acyl-Acyl Carrier Protein in *Escherichia coli*," *J. Biological Chemistry*, 271(4):1833-1836 (1996).
Heck, Richard F., *Organic Reactions*, 1982, 27, pp. 345-390.
Heimbach et al., "Absorption rate limit considerations for oral phosphate prodrugs," *Pharm Res.* Jun. 2003;20(6):848-56.
Himmler et al., "Synthesis and Antibacterial in Vitro Activity of Novel Analogues of Nematophin," *Bioorganic & Medicinal Chemistry Letters*, 8(15): 2045-2050 (Aug. 1998).
Hungarian Search Report dated Dec. 31, 2003.
International Preliminary Report on Patentability dated Jan. 20, 2009, for PCT/CA2007/001277.
International Search Report and Written Opinion for International Application No. PCT/IB2013/001780 mailed Dec. 3, 2013, 12 pages.
International Search Report and Written Opinion for International Application No. PCT/US2011/040187 mailed Nov. 30, 2011.
International Search Report dated Apr. 20, 2005 for PCT/US2002/10332.
International Search Report dated Apr. 21, 2004 for PCT/US2003/38706.
International Search Report dated Feb. 22, 2001 for PCT/US2000/27619.
International Search Report dated Jan. 25, 2001 for PCT/US2000/27844.
International Search Report dated Jan. 29, 2001 for PCT/US2000/27591.
International Search Report dated Jun. 14, 2007 for PCT/US2005/019805.
International Search Report dated Jun. 5, 2008 for PCT/CA2008/000300.
International Search Report dated Oct. 13, 2004 for PCT/IB2004/001261.
International Search Report dated Oct. 26, 2007 for PCT/CA2007/001277.
International Search Report dated Oct. 4, 2000 for PCT/US2000/15154.
International Search Report dated Sep. 12, 2007 for PCT/US2006/045903.
Jianxiong Li et al., "Synthesis and Antistaphylococcal Activity of Nematophin and Its Analogs," *Bioorganic & Medicinal Chemistry Letters* Oxford, GB, 7(10):1349-1352, (1997) XP004136332.
Jossang-Yanagida et al., "Tetrahydropyridoazepines and Tetrahydropyridoazepinones from the Corresponding Dihydroquinolones," *J. Heterocyclic Chemistry*, 15:249-251 (1978).
Kaplan and Hafkin "F1-2005—In Vitro and In Vivo Absorption Properties of AFN-1252, a Novel Specific-Spectrum Anti-Staphylcoccal Agent," 233—New Agents on Bacterial Membranes Presentation Abstract Tuesday, Sep. 15, 2009, 9:00 AM-11:00 AM.
Kaplan et al., "F1-2006—Correlation of AFN-1252 Phase 0 Microdosing and Phase 1 Pharmacokinetics," 233—New Agents on Bacterial Membranes Presentation Abstract Tuesday, Sep. 15, 2009, 9:00 AM-11:00 AM.
Karlowsky et al., "AFN-1252, a FabI Inhibitor, Demonstrates a *Staphylococcus*-Specific Spectrum of Activity," *Antimicrobial Agents and Chemotherapy*, 53(8):3544-3548 (2009).
Karlowsky et al., "In Vitro activity of API-1252, a Novel FabI inhibitor, against Clinical Isolates of *Staphylococcus aureus* and *Staphylococcus epidermidis*", *Antimicrobial Agents and Chemotherapy*, 51(4):1580-1581 (Apr. 2007).
Kearney et al., "The in vitro enzymic labilities of chemically distinct phosphomonoester prodrugs", Pharm Res, 9(4):497-503 (1992).
Leppik et al., "Pharmacokinetics and safety of a phenytoin prodrug given i.v. or i.m. in patients," Neurology, Mar. 1990;40(3 Pt 1):456-60.
Levy et al., "Molecular Basis of Triclosan Activity," *Nature* 398:383-384 (1999).
McMurray et al., "Triclosan Targets Lipid Synthesis," *Nature*, 394:531-532 (1998).
Miller et al., "Discovery of Aminopyridine-Based Inhibitors of Bacterial Enoyl-ACP Reductase (FABI)" *J. Med. Chem.*, 45:3246-3256 (2002).
Misztal et al., "Synthesis and Pharmacologic Properties of Pyridol Derivatives of 3-Methylaminoindole 2-Methyltryptamine and Isostryptamine," *Archivum Immnologiae et Therapiae Experimentalis*, 24(6):851-862 (1976).
Pachter et al., "The Chemistry of Hortiamine and 6-Methoxyhetsinine," *J. Amer. Chem.*, 83:635-642 (1961).
Patent Abstract of Japan vol. 2000, No. 02, Feb. 29, 2000, JP 11-302173.
Payne et al., "Discovery of a Novel and Potent Class of FabI-Directed Antibacterial Agents," *Am Soc for Microbiology*, 46(10):3118-3124 (2002).
Payne et al., *Drug Discovery Today*, 537-543 (2001).
Ramnauth et al., "2,3,4,5-Tetrahydro-1H-pyrido[2,3-b and e][1,4]diazepines as inhibitors of the bacterial enoyl ACP reductase, Fab I", *Bioorganic & Medicinal Chemistry Letters*, 19(18):5359-5362 (2009).
Rehse et al., "Dopaminanaloge 1,2,3,4-Tetrahydro-β-Carboline," *Arch. Pharm.*, 311(1): 11-18.
Seefeld et al., "Indole Naphthyridinones as Inhibitors of Bacterial Enoyl-ACP Reductases FabI and FabK" *J. Med. Chem.* 46:1627-1635 (2003).
Shoji et al., "Two Novel Alkaloids from Evodia Rutaecarpa," *J. Natural Products*, 52(5):1160-1162 (1989).
Sladowska et al. "Synthesis and properties of amides of 1-benzyl-3-methyl and 1-butyl-3-phenyl-7-methyl-4-oxo-2-thioxo (2,4-dioxo)-1,2,3,4-tetrahydropyrido-[2,3-d]pyrimidine-6-carboxylic acids" *Farmaco Edizione Scientifica* 41:954-963 (1986).
Stutz et al. "Synthesis and Structure-Activity Relationships of Naftifine-Related Allylamine Antimycotics," *Journal of Medicinal Chemistry*, 29(1):112-125 (1986).
Turnowsky et al., "envM Genes of *Salmonella typhimurium* and *Escherichia coli*," *J. Bacteriology*, 171(12):6555-6565 (1989).
Varia et al., "Phenytoin Prodrugs III: Water-Soluble Prodrugs for Oral and/or Parenteral Use", J Pharm Sci, 73(8):1068-1073 (1984).
Varia et al., "Phenytoin prodrugs IV: Hydrolysis of various 3-(hydroxymethyl)phenytoin esters", J Pharm Sci, 73(8):1074-1080 (1984).

(56) References Cited

OTHER PUBLICATIONS

Varia et al., "Phenytoin prodrugs V: In vivo evaluation of some water-soluble phenytoin prodrugs in dogs", J Pharm Sci, 73(8):1080-1087 (1984).

Varia et al., "Phenytoin prodrugs VI: In vivo evaluation of a phosphate ester prodrug of phenytoin after parenteral administration to rats", J Pharm Sci, 73(8):1087-1090 (1984).

Ward et al., "Kinetic and Structural Characteristics of the Inhibition of Enoyl (Acyl Carrier Protein) Reductase by Triclosan," *Biochemistry*, 38:12514-12525 (1999).

ACRYLAMIDE DERIVATIVES AS FAB I INHIBITORS

RELATED APPLICATIONS

This application is a continuation of U.S. Ser. No. 12/374,444, filed Nov. 25, 2009, which is the National Stage Entry of International Application No. PCT/CA07/01277, filed Jul. 19, 2007, which claims priority to provisional application U.S. Ser. No. 60/832,058, filed Jul. 20, 2006, each of which is hereby incorporated by reference in its entirety.

GOVERNMENT SUPPORT

The invention was made with support provided by the National Institute of Health; the government, therefore, has certain rights in the invention.

INTRODUCTION

Infections caused by or related to bacteria are a major cause of human illness worldwide, and the frequency of resistance to standard antibiotics has risen dramatically over the last decade. Hence, there exists an unmet medical need and demand for new agents acting against bacterial targets.

Examples of potential bacterial targets are those enzymes involved in fatty acid biosynthesis. While the overall pathway of saturated fatty acid biosynthesis is similar in all organisms, the fatty acid synthase (FAS) systems vary considerably with respect to their structural organization. It is believed that vertebrates and yeast possess a FAS in which all the enzymatic activities are encoded on one or two polypeptide chains, respectively, and the acyl carrier protein (ACP) is an integral part of the complex. In contrast, in bacterial FAS, it is known that each of the reactions is catalyzed by a distinct, monofunctional enzyme and the ACT is a discrete protein. Therefore, it may be possible to achieve selective inhibition of the bacterial system by appropriate agents.

One such potential bacterial target is the FabI protein. FabI (previously designated EnvM) is believed to function as an enoyl-ACP reductase in the final step of the four reactions involved in each cycle of bacterial fatty acid biosynthesis. It is believed that in this pathway, the first step is catalyzed by β-ketoacyl-ACP synthase, which condenses malonyl-ACP with acetyl-CoA (FabH, synthase III). It is believed that in subsequent rounds, malonyl-ACP is condensed with the growing-chain acyl-ACP (FabB and FabF, synthases I and II, respectively). The second step in the elongation cycle is thought to be ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP. Finely, in step four, trans-2-enoyl-ACP is converted to acyl-ACP by an NADH (or NADPH)-dependent enoyl-ACP reductase (Fab I). Further rounds of this cycle, adding two carbon atoms per cycle, would eventually lead to palmitoyl-ACP (16C), where upon the cycle is stopped largely due to feedback inhibition of Fab I by palmitoyl-ACP. Thus, Fab I is believed to be a major biosynthetic enzyme and is a key regulatory point in the overall synthetic pathway of bacterial fatty acid biosynthesis.

In some bacteria the final step of fatty acid biosynthesis is catalyzed by Fab I only, in others by FabK, an NADH and FMN dependent reductase, still others utilize both FabI and FabK. The present invention provides, in part, compounds and compositions with FabI inhibiting properties.

SUMMARY

In part, the present invention is directed towards compounds with FabI inhibiting properties as well as other enzymes. Other uses for the subject compounds and compositions will be readily disernable to those of skill in the art.

In part, the present invention is directed towards compounds that will affect multiple species, so-called "wide spectrum" anti-bacterials. Alternatively, subject compounds that are selective for one or more bacterial or other non-mammalian species, and not for one or more mammalian species (especially human), may be identified.

In part, the present invention is directed towards pharmaceutical compositions comprising a compound with FabI inhibiting properties.

The subject compositions may be administered by one of a variety of means known to those of skill in the art. The subject compounds may be prepared as described herein and as known to those of skill in the art.

Whole-cell antimicrobial activity for the antibacterial compositions of the present Invention may be determined by broth microdilution using the National Committee for Clinical Laboratory Standards (NCCLS) recommended procedure. Document M7-A5, "Methods for Dilution Susceptibility Tests for Bacteria that Grow Aerobically". The compositions of the present invention may be tested, for example, in serial two-fold dilutions ranging from 0.06 to 32 mcg/mL. A panel of up to 12 or more bacterial strains may be evaluated in the assay. A panel may consist of, for example, the following laboratory strains: *Enterococcus faecalis* 29212, *Staphylococcus aureus* 29213, *Staphylococcus aureus* 43300, *Moraxella catarrhalis* 49143, *Haemophilus influenzae* 49247, *Streptococcus pneumoniae* 49819, *Staphylococcus epidermidis* 1024939, *Staphylococcus epidermidis* 1024961, *Escherichia coli* AG100 (AcrAB$^+$), *Escherichia coli* AG100A (AcrAB$^-$), *Pseudornonas aeruginosa* K767 (MexAB$^+$, OprM$^+$), *Pseudomonas aeruginosa* K1119 (MexAB$^-$, OprM$^-$). The minimum inhibitory concentration (MIC) may then be determined as the lowest concentration of the subject composition that inhibited visible growth. A spectrophotometer may be used to assist in determining the MIC endpoint.

Non-limiting examples of bacteria that the antibacterial compounds or compositions of the present invention may be used to either destroy or inhibit the growth of include a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Francisella, Pasturetta, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudornonas, Aeromonas, Rickettsia, Chlamydia, Borrelia, Propionibacterium acnes*, and *Mycoplasma*, and further including, but not limited to a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis*, coagulase negative *Staphylococci, Staphylococcus aureus, Staphylococcus epidermidis, Corynebacterium diptheriae, Gardnerella vaginalis, Mycobacterium tuberculosis, Mycobacterium bovis, Mycobacterium*, ulcer arts, *Mycobacterium leprae, Actinomyctes israelii, Listeria monocytogenes, Bordetella pertusis, Bordatella parapertusis, Bordetella hronchiseptica, Escherichia coli, Shigella dysenteriae, Haemophilus influenzae, Haemophilus aegyptius, Haemophilus parainfluenzae, Haemophilus* ducreyi, Bordetella, Salmonella typhi, Citrobactoer freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsti, Helicobacter pylori or Chlamydia trachomitis.

In another aspect, the subject compounds or compositions may be used to treat bacterial infections.

In certain embodiments, the present invention provides antibacterial compositions of the present invention, and methods of using the same, for the reduction and abatement of at least one of the bacteria caused disorders or conditions based on a therapeutic regimen. In certain aspects, the present invention contemplates monitoring such disorders or conditions as part of any therapeutic regimen, which may be administered over the short-term and/or long-term. These aspects of the invention may be particularly helpful in preventive care regimes.

In another aspect of the present invention, the antibacterial compounds or compositions of the present invention may be used in the manufacture of a medicament to treat any of the foregoing bacteria related conditions or diseases. In certain embodiments, the present invention is directed to a method for formulating compounds of the present invention in a pharmaceutically acceptable carrier or excipient.

In part, the present invention also relates to inhibitors and compositions comprising inhibitors of enzymes similar to FabI either structurally or functionally, such as, for example, FabK which is also believed to play a role in bacterial fatty acid synthesis.

In another aspect of the present invention, the antibacterial compounds of the present invention may be used to disinfect an inanimate surface by administering the antibacterial compound to the inanimate surface.

For continuous intravenous infusion, e.g., drip or push, the antibacterial agent can be provided in a sterile dilute solution or suspension (collectively hereinafier "i.v. injectable solution"). The i.v. injectable solution may be formulated such that the amount of antibacterial agent (or antibacterial agents) provided in a 1 L solution would provide a dose, if administered over 15 minutes or less, of at least the median effective dose, or less than 100 times the $ED_{50}$, or less than 10 or 5 times the $ED_{50}$. The i.v. injectable solution may be formulated such that the total amount of antibacterial agent (or antibacterial agents) provided in 1 L solution administered over 60, 90, 120 or 240 minutes would provide an $ED_{50}$ dose to a patient, or less than 100 times the $ED_{50}$, or less than 10 or 5 times the $ED_{50}$. In other embodiments, a single i.v, "bag" provides about 0.25 mg to 5000 mg of antibacterial agent per liter i.v. solution, or 0.25 mg to 2500 mg, or 0.25 mg to 1250 mg.

In another embodiment of the invention it will be desirable to include monitoring or diagnostic regimes or kits with subject antibacterial compounds or methods based on FabI inhibitors described herein, and instructions for use of these compositions or methods.

In another aspect, the present invention also provides for kits containing at least one dose of a subject composition, and often many doses, and other materials for a treatment regimen. For example, in one embodiment, a kit of the present invention contains sufficient subject composition for from five to thirty days and optionally equipment and supplies necessary to measure one or more indices relevant to the treatment regiment. In another embodiment, kits of the present invention contain all the materials and supplies, including subject compositions, for carrying out any methods of the present invention. In still another embodiment, kits of the present invention, as described above, additionally include instructions for the use and administration of the subject compositions.

The dosage may be selected to modulate metabolism of the bacteria in such a way as to inhibit or stop growth of said bacteria or by killing said bacteria. The skilled artisan may identify this amount as provided herein as well as by using other methods known in the art.

As explained herein in greater detail, the invention will readily enable the design and implementation of trials in warm-blooded animals, including humans and mammals, necessary for easily determining or tailoring the form and dose for any composition of the present invention.

These embodiments of the present invention, other embodiments, and their features and characteristics, will be apparent from the description, drawings and claims that follow.

DETAILED DESCRIPTION

Introduction

The present invention is directed in part towards novel compositions that inhibit bacterial enzymes, and methods of making and using the same. In certain aspects, inhibitors and other compounds of the invention may be found by a structure-guided medicinal chemistry effort.

Figure 1:
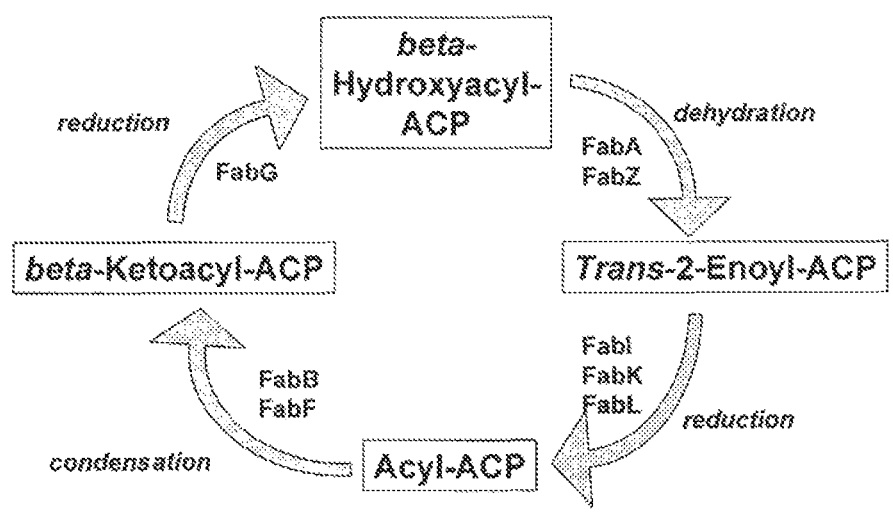
FIG. 1 depicts the bacterial fatty acid biosynthesis cycle via a Type II or dissociated fatty acid synthase system.

Bacterial fatty acid biosynthesis is believed to proceed via a Type II or dissociated fatty acid synthase system, in contrast to the mammalian Type I system. The overall process is believed to proceed in two stages—initiation and cyclical elongation. Enoyl-ACP reductase is part of the elongation cycle, in which malonyl-ACP is condensed with a growing acyl chain by b-ketoacyl-ACP synthase (FabB, FabF, FabH). The β-ketoester is reduced by β-ketoacyl-ACP reductase, which is then dehydrated to the trans-unsaturated acyl-ACP. The trans-unsaturated acyl-ACP is then reduced by enoyl-ACP reductase. (See FIG. 1).

The enoyl-ACP reductase step is believed to be accomplished by FabI in *E. coli* and other gram negative organisms and *Staphylococci*. In certain gram-positive organisms, FabI paralogs exist. In *Streptococcus pneumoniae*, the enzymatic step is believed to be accomplished by the FabK protein, which has limited homology with the *S. aureus* FabI protein. In *B. subtilis* and *E. faecalis*, genes encoding both FabI and FabK exist. In *Mycobacterium tuberculosis* a FabI paralog termed InhA exists.

Enoyl-ACP reductase is believed to be the enzymatic target of the antimicrobial product triclosan.

Figure 2:
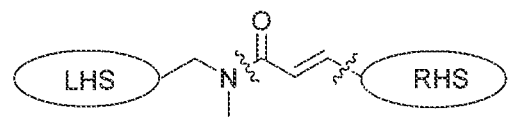
FIG. 2 depicts a simplified view of ene-amide core flanked by LHS (left-hand side) and RHS (right-hand side) moieties.

In certain embodiments, the design of new analogs having FabI inhibiting properties is based on viewing the analogs as consisting of a central acrylamide flanked by two relatively hydrophobic groups, conveniently denoted as left-hand side (LHS) and right-hand side (RHS) as put forth in U.S. Provisional Patent Application 60/431,406. Schematically this is depicted in FIG. 2, where a dumbbell like structure provides one way of viewing certain of the subject compositions (the central bond disconnections that is envisioned in a retrosynthetic sense are shown with dashed lines).

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria and plants.

The term "enzyme inhibitor" refers to any compound that prevents an enzyme from effectively carrying out its respective biochemical roles. Therefore a "FabI inhibitor" is any compound that inhibits FabI from carrying out its biochemical role. The amount of inhibition of the enzyme by any such compound will vary and is described herein and elsewhere.

The term "antibiotic agent" shall mean any drug that is useful in treating, preventing, or otherwise reducing the severity of any bacterial disorder, or any complications thereof, including any of the conditions, disease, or complications arising therefrom and/or described herein. Antibiotic agents include, for example, cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and the like. Other general categories of antibiotic agents which may be part of a subject composition include those agents known to those of skill in the art as antibiotics and that qualify as (with defined terms being in quotation marks); "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. §355(a) ("regulatory approved drug"); any agent that is or was subject to a human drug application under 21 U.S.C. §379(g) ("human drug"). (All references to statutory code for this definition refer to such code as of the original filing date of this provisional application.) Other antibiotic agents are disclosed herein, and are known to those of skill in the art. In certain embodiments, the term "antibiotic agent" does not include an agent that is a FabI inhibitor, so that the combinations of the present invention in certain instances will include one agent that is a FabI inhibitor and another agent that is not.

The term "synergistic" is art recognized and refers to two or more components working together so that the total effect is greater than the sum of the effect of the components.

The term "illness" as used herein refers to any illness caused by or related to infection by an organism.

The term "bacterial illness" as used herein refers to any illness caused by or related to infection by bacteria.

The term "polynucleotide(s)" is art recognized and refers to any polyribonucleotide or polydeoxyribonucleotide, that may be unmodified RNA or DNA or modified RNA or DNA. "Polynucleotide(s)" include, without limitation, single- and double-stranded DNA. DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "polypeptide(s)" is art recognized and refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond, formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxy sation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, $2^{nd}$ Ed., T. E. Creighton, W.H. Freeman and Company, New York (1993) and Wold, P., Posttranslational Protein Modifications: Perspectives and Prospects, pgs. 1-12 in *POSTTRANSLAIONAL COVALENT MODIFICATION OF PROTEINS*, B. C. Johnson, Ed., Academic Press, Mew York (1983); Setter et al., *Meth Emzymol.* 182:626-646 (1990) and Rattan et al., *Protein Synthesis: Posttranslational Modifications and Aging*, Ann. N.Y. Acad. Sci. 663:48-62 (1992). Polypeptides may be branched or cyclic, with or without branching. Cyclic, branched and branched circular polypeptides may result from post-translational natural processes and may be made by entirely synthetic methods, as well.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangementof two atoms or groups around a double bond such that the stems or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, md the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described ip well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, care or mitigation of a disease or illness; substances which affect the stracture or function of the body; or pro-drugs, which become biologically active or more active after they have been placed in a physiological environment. Antibiotic agents and FabI/Fab K inhibitors are examples of therapeutic agents.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficent amount to produce a at a reasonable benefit/risk ratio applicable to such treatment.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intentend environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be eovalerttly bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposahle on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "emantiomers" refer to two stereoisomers of a compound which are non-superimposable mirror images of one another. "Diasteomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal is 50% of test subjects. The term "therapeutic index" is an art-recognized term winch refers to the therapeutic index of a drug, defined as $LD_{50}/ED_{50}$.

The term "$K_i$" is art-recognized and refers to the dissociation constant of the enzyme-inhibitor complex.

The term "antimicrobial" is art-recognized and refers to the ability of the compounds of the present invention to prevent, inhibit or destroy the growth of microbes such as bacteria, fungi, protozoa and viruses.

The term "antibacterial" is art-recognized and refers to the ability of the compounds of the present invention to prevent, inhibit or destroy the growth of microbes of bacteria.

The term "microbe" is art-recognized and refers to a microscopic organism. In certain embodiments the term microbe is applied to bacteria. In other embodiments the term refers to pathogenic forms of a microscopic organism.

The term "prodrug" is art-recognized and is intended to encompass compounds which, under physiological conditions, are converted into the antibacterial agents of the present invention. A common method for making a prodrug is to select moieties which are hydrolyzed under physiological conditions to provide the desired compound. In other embodiments, the prodrug is converted by an enzymatic activity of the host animal or the target bacteria.

The term "structure-activity relationship" or "(SAR)" is art-recognized and refers to the way in which altering the molecular structure of a drug or other compound alters its interaction with a receptor, enzyme, nucleic acid or other target and the like.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamide, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamide, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heleroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatorns. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indoiizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyi, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl ether, alkylthio, sulfonyl, ketone, aldehyde, ester, a heterocyclyl, an aromatic or heteroaromatic moiety, —CF$_3$, —CN, or the like.

The term "carbocylce" is art-recognized and refers to an aromatic or non-aromatic ring in which each atom of the ring is carbon.

The term "nitro" is art-recogonized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

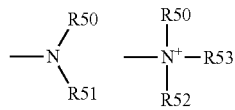

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring strusture; R61 represents an aryl, a cycloalkyl, a cycloalkenyl, a heterocycle or a polycycle; and m is zero or an integer in the range of 1 to 8. In certain embodiments, only one of R50 or R51 may be a carbonyl e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

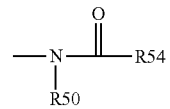

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

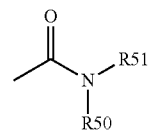

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognised, and includes such moieties as may be represented by the general formulas:

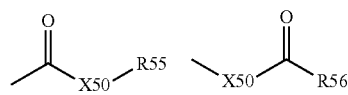

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

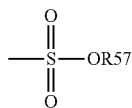

in which R57 is an electron pair, hydrogen, alkyl, cycloalkyl, or aryl.

The term "sulfate" is art recognized and includes a moiety that may be represented by the general formula:

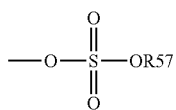

in which R57 is as defined above.

The term "sulfonamido" is art recognised and includes a moiety that may be represented by the general formula:

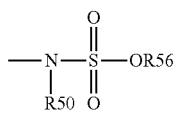

in which R50 and R56 are as defined above.

The term "sulfamoyl" is art-recognized and refers to a moiety that may be represented by the general formula:

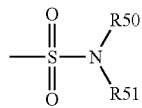

in which R50 and R51 are as defined above.

The term "sulfonyl" is art-recognized and refers to a moiety that may be represented by the general formula:

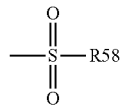

in which R58 is one of the following: hydrogen, alkyl, alkenyl, alkynyl, cycloalkyl, heterocyclyl, aryl or heteroaryl.

The term "sulfoxido" is art-recognixed and refers to a moiety that may be represented by the general formula:

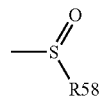

in which R58 is defined above.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonly, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluormethanesulfonyl, norafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomrs, R- and S-enantiomerss diasteremers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enautiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, eliminations or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67$^{th}$ Ed., 1986-87, inside cover. Also for purposes of this invention, the term "hydrocarbon" is contemplated to include all permissible compounds having at least one hydrogen, and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2$^{nd}$ ed., Wiley: New York, 1991).

The term "hydroxyl-protecing group" is art-recognized and refers to those groups intended to protect a hydroxyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorohenzyl; acyl groups and substituted acyl-such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylenyl, and p-toluenesulfonyl-aminocarbonyl. Preferred amino-blocking groups are benzyl (—CH$_2$C$_6$H$_5$), acyl [C(O)R1] or SiR1$_3$ where R1 is C$_1$-C$_4$ alkyl, halomethyl, or 2-halo-suhstituted-(C$_2$-C$_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A qualification of the level of electron-withdrawing capability is given by the Hammett sigma ($\sigma$) constant. This well known constant is described in many references, for instance, March, *Advanced Organic Chemistry* 251-59 (McGraW Hill Book Company: New York, 1977). The Hammett constant values are generally negative for electron donating groups ($\sigma(P)$=–0.66 for NH$_2$) and positive for electron withdrawing groups ($\sigma(P)$=0.78 for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "modulation" is art-recognized and refers to up regulation (i.e., activation or stimulation), down regulation (i.e., inhibition or suppression) of a response, or the two in combination or apart.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or oilier unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effect therefrom).

A "patient," "subject" or "host" to be treated by the subject method may mean either a human or non-human animal.

The term "mammal" is known in the art, and exemplary mammals include humans, primates, bovines, porcine, canines, felines, and rodents (e.g., mice and rats).

The term "bioavallable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion, of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyi cellulose, ethyl cellulose and cellulose acetate; (4) powdered tragacanth; (5) malt; (6) gelatin; (7) tale; (8) excipients, such as cocoa butter and suppository waxes; (9) oils, such as peanut oil, cottonseed oil, safflower oil, sesame oil, olive oil, corn oil and soybean oil; (10) glycols, such as propylene glycol: (11) polyols, such as glycerin, sorbitol, mannitol and polyethylene glycol; (12) esters, such as ethyl oleate and ethyl karate; (13) agar; (14) buffering agents, such as magnesium hydroxide and aluminum Hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration.

The terms "parenteral admimstation" and "administered parenterally" are art-recognised and refer to modes of admmistration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compositions described herein include compositions which otherwise correspond, thereto, and which, have the same general properties thereof (such as other compositions comprising FabI/Fab K inhibitors), wherein one or more simple variations of substituents or components are made which do not adversely affect the characteristics of the compositions of interest. In general, the components of the compositions of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

FaBI Inhibitors

The FabI inhibitor compounds of the present invention include those depicted by formula I:

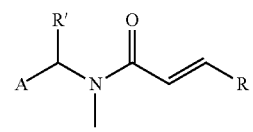

wherein, independently for each occurrence,

A is a monocyclic ring of 4-7 atoms containing 0-2 heteroaioms, a bicyclic ring of 8-12 atoms containing 0-4 heteroatoms or a tricyclic ring of 8-12 atoms containing 0-6 heteroatoms wherein the rings are independently aliphatic, aromatic, heteroaryl or heterocyclic in nature, the heteroatoms are selected from N, S or O and the rings are optionally substituted with one or more groups selected from $C_{1-4}$ alkyl, OR", CN, $OCF_3$, F, Cl, Br, I; wherein R" is H, alkyl, aralkyl, or heteroaralkyl; R' is H or alkyl;

R is

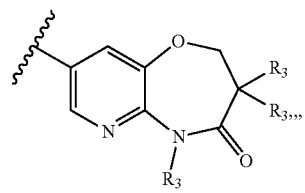

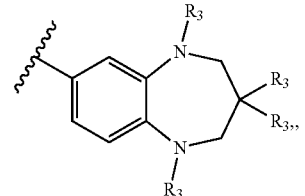

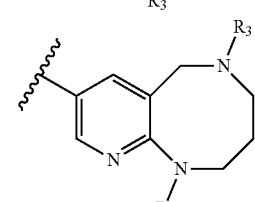

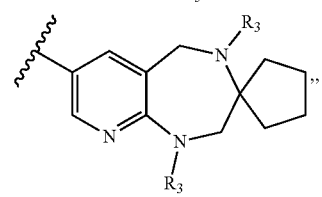

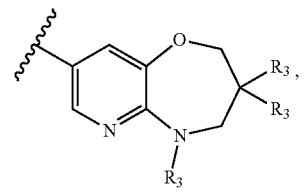

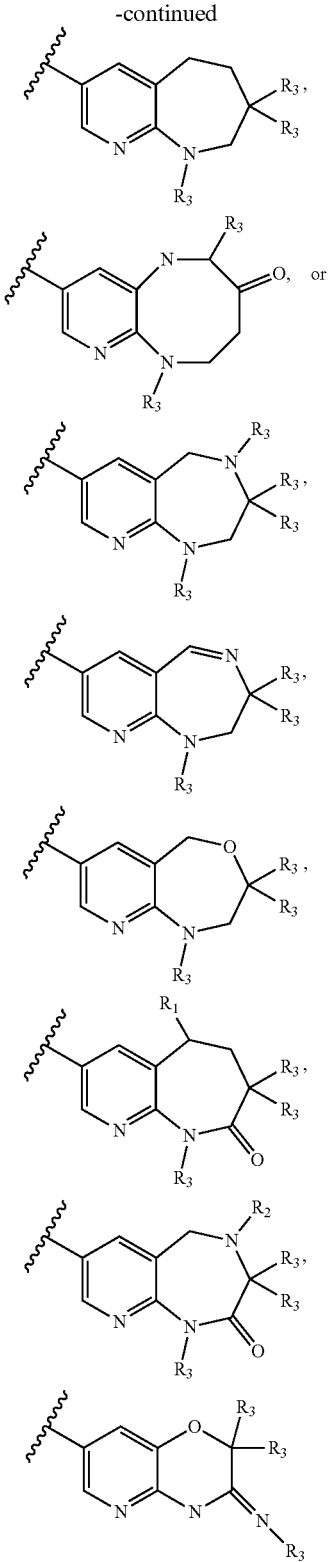

wherein, independently for each occurrence,

R₁ is H or OH;

R₂ is OH or —Ar; and

R₃ is each independently H, alkyl, carbonyl, sulfonyl, or aryl.

In a further embodiment, the present invention includes compounds of formula I and the attendant definitions, wherein A is selected from the following:

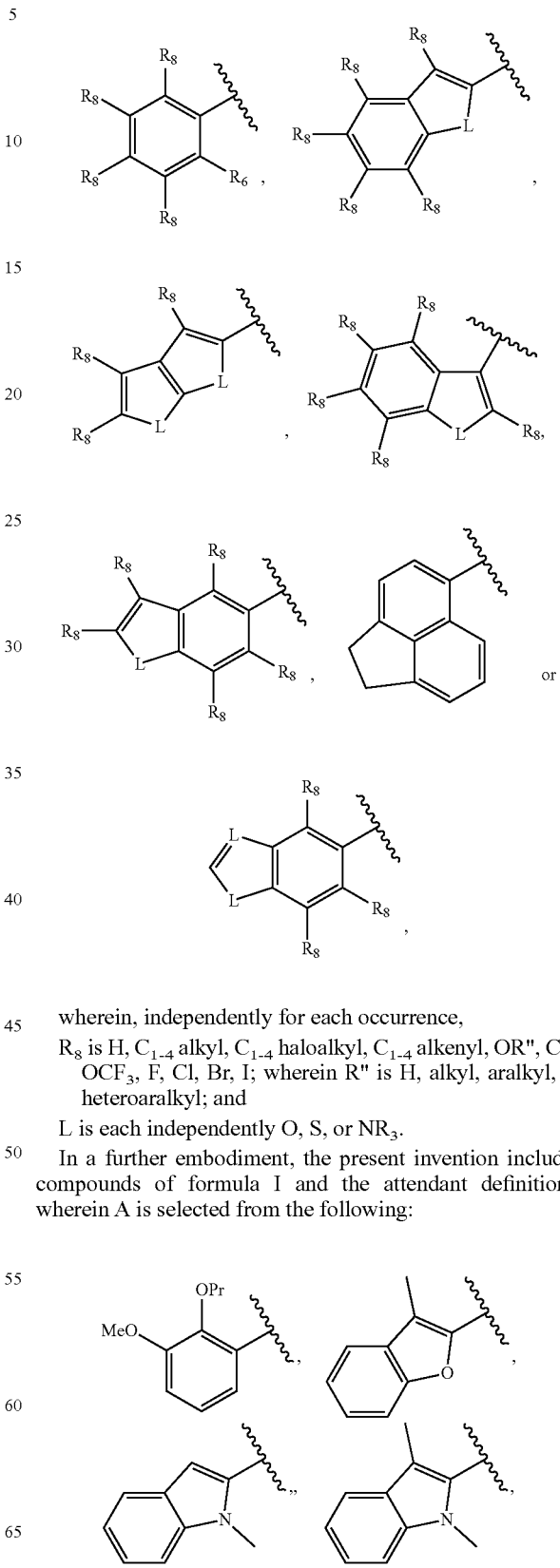

wherein, independently for each occurrence, $R_8$ is H, $C_{1-4}$ alkyl, $C_{1-4}$ haloalkyl, $C_{1-4}$ alkenyl, OR″, CN, $OCF_3$, F, Cl, Br, I; wherein R″ is H, alkyl, aralkyl, or heteroaralkyl; and L is each independently O, S, or $NR_3$.

In a further embodiment, the present invention includes compounds of formula I and the attendant definitions, wherein A is selected from the following:

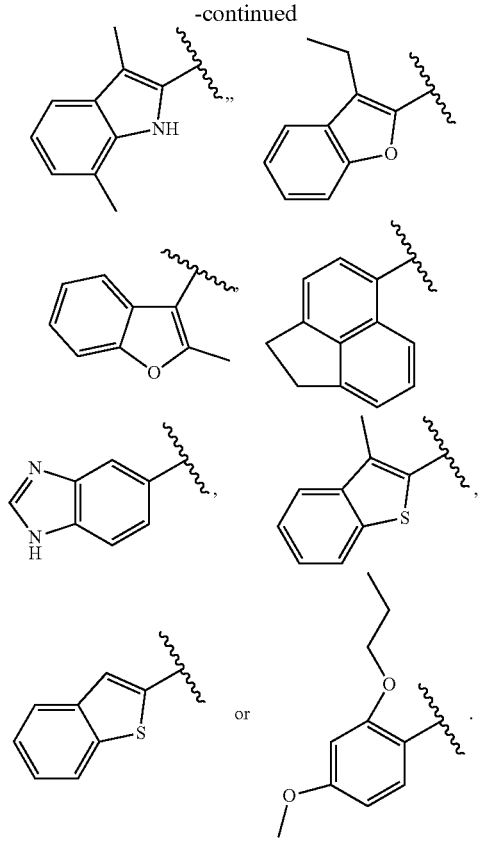

In a further embodiment, the present invention relates to compounds of formula I, wherein the compound has formula Ia:

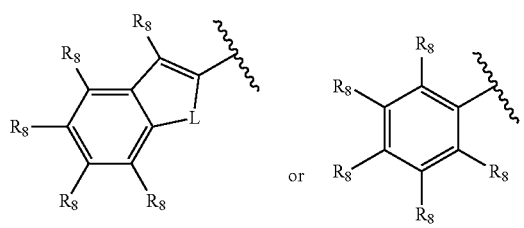

wherein,
R' and $R_3$ are as previously defined, and
A is selected from the following:

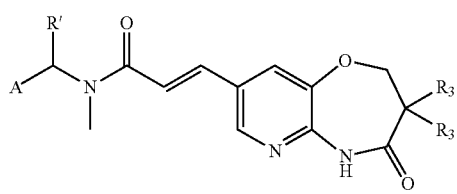

wherein L and $R_8$ are as previously defined.

In a further embodiment, the present invention relates to compounds of formula Ia and the attendant definitions, wherein R' is H.

In a further embodiment, the present invention relates to compounds of formula Ia and the attendant definitions, wherein R+ is methyl.

In a further embodiment, the present invention relates to compounds of formula Ia and the attendant definitions, wherein $R_3$ is methyl.

In a further embodiment, the present invention relates to compounds of formula Ia and the attendant definitions, wherein A is

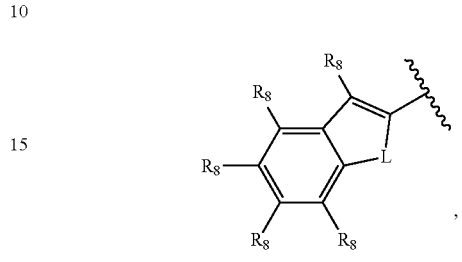

In a further embodiment, the present invention relates to compounds of formula Ia and the attendant definitions, wherein A is

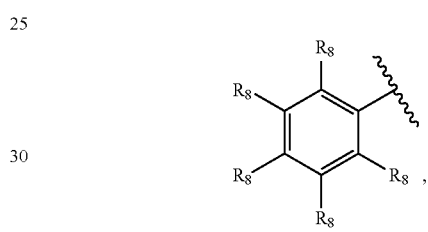

In a further embodiment, the present invention relates to compounds of formula Ia and the attendant definitions, wherein A is

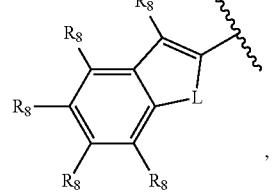

and L is O.

In a further embodiment, the present invention, relates to compounds of formula Ia and the attendant definitions, wherein A is

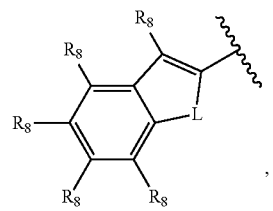

and L is N.

In a further embodiment, the present invention relates to compounds of formula Ia and the attendant definitions, wherein A is

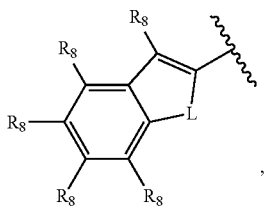

L is O, N or S, and $R_8$ is H or alkyl.

In a further embodiment, the present invention relates to compounds of formula Ia and the attendant definitions, wherein A is

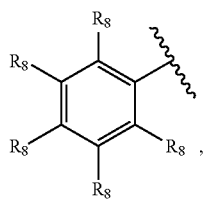

wherein $R_8$ is OR" or H, and R" is alkyl.

In a further embodiment, the present invention relates to compounds of formula I, wherein the compound has formula Ib:

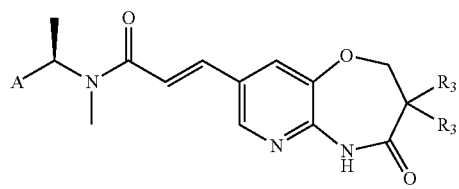

wherein, $R_3$ is as defined previously, and

A is selected from the following:

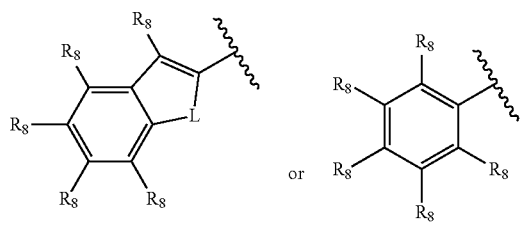

wherein L and $R_8$ are as previously defined.

In a further embodiment, the present invention relates to compounds of formula Ib and the attendant definitions, wherein $R_3$ is each independently H or alkyl.

In a further embodiment, the present invention relates to compounds of formula Ib and the attendant definitions, wherein A is

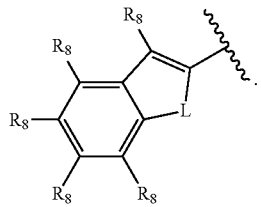

In a further embodiment, the present invention relates to compounds of formula Ib and the attendant definitions, wherein A is

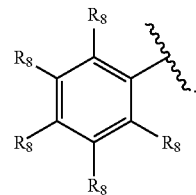

In a further embodiment, the present invention relates to compounds of formula Ib and the attendant definitions, wherein A is

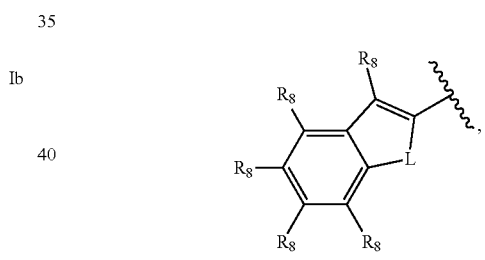

and L is O.

In a further embodiment, the present invention relates to compounds of formula Ib and the attendant definitions, wherein A is

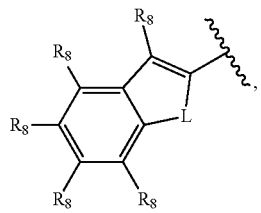

and $R_8$ is H or alkyl.

In a further embodiment, the present invention relates to compounds of formula Ib and the attendant definitions, wherein A is

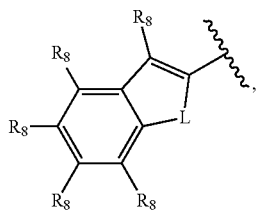

L is O or S, and $R_8$ is H or alkyl.

In a further embodiment, the present invention relates to compounds of formula Ib and the attendant definitions, wherein A is

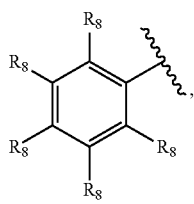

$R_8$ is H or OR", and R" is alkyl.

In a further embodiment, the present invention relates to compounds of formula I, wherein the compound has formula Ic:

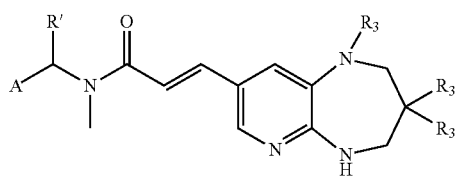

Ic wherein,

R' and $R_3$ are as defined previously, and

A is:

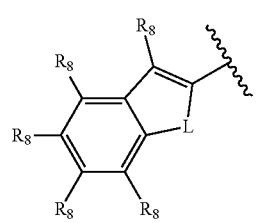

wherein L and $R_8$ are as previously defined.

In a further embodiment, the present invention relates to compounds of formula Ic and the attendant definitions, wherein R' is H.

In a further embodiment, the present invention relates to compounds of formula Ic and the attendant definitions, wherein $R_3$ is H.

In a further embodiment, the present invention relates to compounds of formula Ic, and the attendant definitions, wherein A is

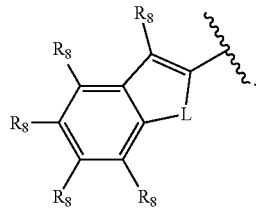

In a further embodiment, the present invention relates to compounds of formula Ic and the attendant definitions, wherein A is

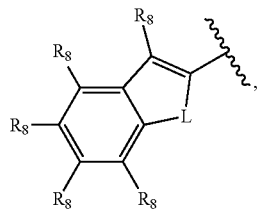

and L is O.

In a further embodiment, the present invention relates to compounds of formula Ic and the attendant definitions, wherein A is

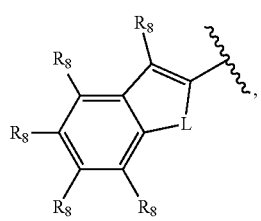

and L is S.

In a further embodiment, the present invention relates to compounds of formula Ic and the attendant definitions, wherein A is

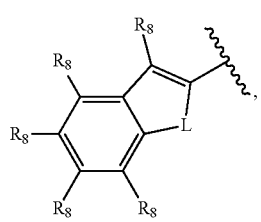

and $R_8$ is H, or alkyl.

In a further embodiment, the present invention relates to compounds of formula Ic and the attendant definitions, wherein A is

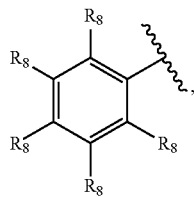

R$_8$ is H or OR", and R" is alkyl.

In a further embodiment, the present invention relates to compounds of formula I, wherein the compound has formula Id:

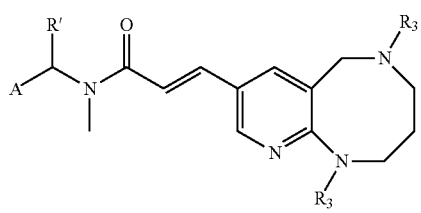

wherein,

R' and R$_3$ are as defined previously, and

A is selected from the following:

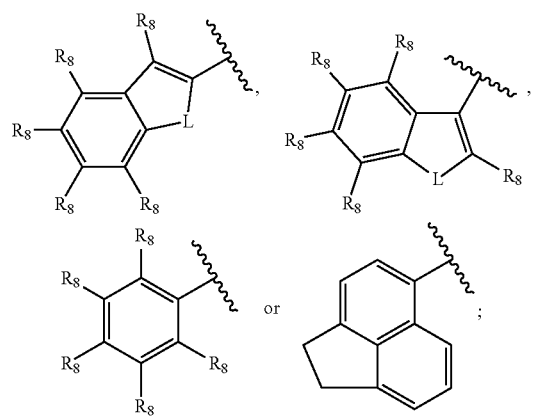

wherein L and R$_8$ are as previiusly defined.

In a further embodiment, the present invention relates to compounds of formula Id and the attendant definitions, wherein R' is H.

In a further embodiment, the present invention relates to compounds of formula Id and the attendant definitions, wherein R$_3$ is H.

In a further embodiment, the present invention relates to compounds of formula Id and the attendant definitions, wherein at least one nitrogen bonded R$_3$ is sulfonyl.

In a further embodiment, the present invention relates to compounds of formula Id and the attendant definitions, wherein at least one nitrogen bonded R$_3$ is methyl.

In a further embodiment, the present invention relates to compounds of formula Id and the attendant definitions, wherein at least one R$_3$ is aryl.

In a further embodiment, the present invention relates to compounds of formula Id and the attendant definitions, wherein at least one nitrogen bonded R$_3$ is

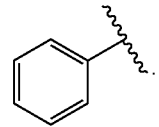

In a further embodiment, the present invention relates to compounds of formula Id and the attendant definitions, wherein at least one R$_3$ is Boc.

In a further embodiment, the present invention relates to compounds of formula Id and the attendant definitions, wherein A is

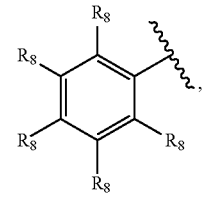

and R$_8$ is H or OR".

In a further embodiment, the present invention relates to compounds of formula Id and the attendant definitions, wherein A is

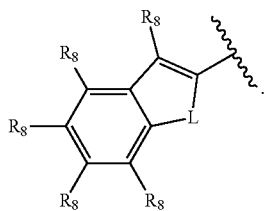

In a further embodiment, the present invention relates to compounds of formula Id And the attendant definitions, wherein A is

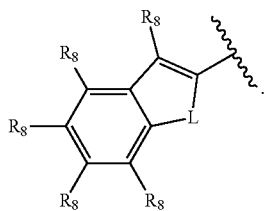

and L is O.

In a further embodiment, the present invention relates to compounds of formula Id and the attendant definitions, wherein A is

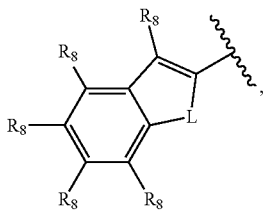

and L is S.

In a further embodiment, the present invention relates to compounds of formula Id and the attendant definitions, wherein A is

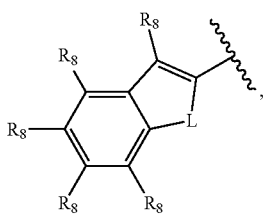

and L is NMe.

In a further embodiment, the present invention relates to compounds of formula Id and the attendant definitions, wherein A is

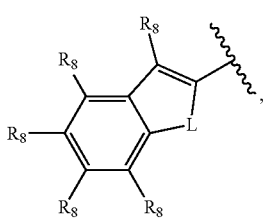

and $R_8$ is H or alkyl.

In a further embodiment the present invention relates to compounds of formula I, Wherein the compound has formula Ie:

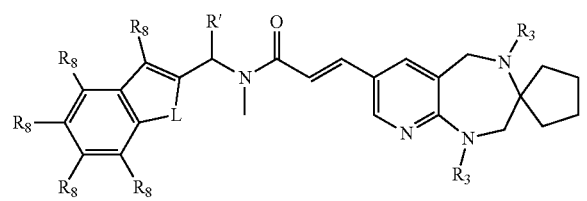

Ie wherein R', $R_3$, $R_8$ and L are as defined previously.

In a further embodiment, the present invention relates to compounds of formula Ie and the attendant definitions, wherein R' is H.

In a further embodiment, the present invention relates to compounds of formula Ie and the attendant definitions, wherein L is O.

In a further embodiment, the present invention relates to compounds of formula Ie and the attendant definitions, wherein $R_8$ is H or Me.

In a further embodiment, the present invention relates to compounds of formula I, wherein the compound has formula If:

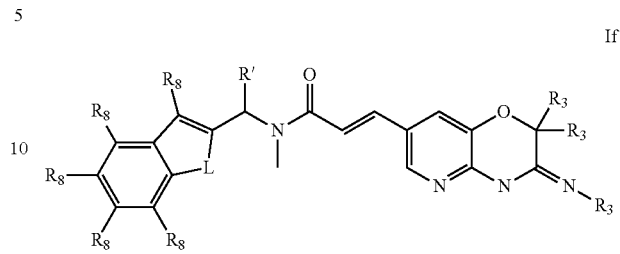

If wherein R', $R_3$, $R_8$, and L are as defined previously.

In a further embodiment, the present invention relates to compounds of formula If and the attendant definitions, wherein R' is H.

In a further embodiment, the present invention relates to compounds of formula If and the attendant definitions, wherein $R_3$ is H.

In a further embodiment, the present invention relates to compounds of formula If and the attendant definitions, wherein L is O.

In a further embodiment, the present invention relates to compounds of formula If and the attendant definitions, wherein L is S.

In a further embodiment, the present invention relates to compounds of formula If and the attendant definitions, wherein $R_3$ is alkyl.

In a further embodiment, the present invention relates to compounds of formula If and the attendant definitions, wherein $R_8$ is H or alkyl.

In a fintber embodiment, the present invention relates to compounds of formula I, wherein the compound has formula Ig:

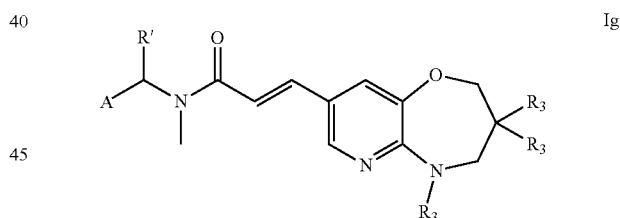

Ig wherein,
R' and $R_3$, are as defined previously, and
A is:

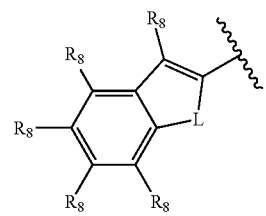

wherein L and $R_8$ are as previously defined.

In a further embodiment, the present invention relates to compounds of/formula Ig and the attendant definitions, wherein R' is H.

In a further embodiment, the present invention relates to compounds of formula Ig and the attendant definitions, wherein R₃ is H or alkyl.

In a further embodiment, the present invention relates to compounds of formula Ig and the attendant definitions, wherein A is

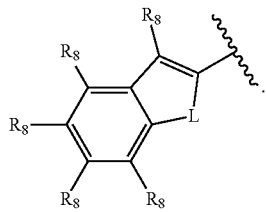

In a further embodiment, the present invention relates to compounds of formula Ig and the attendant definitions, wherein A is

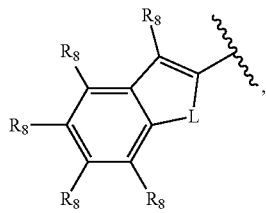

and L is O.

In a further embodiment, the present invention relates to compounds of formula Ig and the attendant definitions, wherein A is

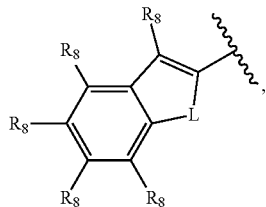

and L is NMe.

In a further embodiment, the present invention relates to compounds of formula Ig and the attendant definitions, wherein A is

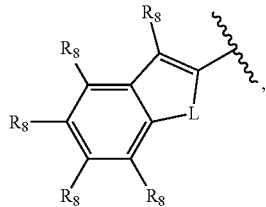

and L is S.

In a further embodiment, the present invention relates to compounds of formula Ig and the attendant definitions, wherein A is

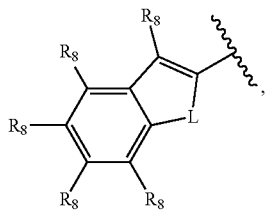

and R₈ is H, or alkyl.

In a further embodiment, the present invention relates to compounds of formula I, wherein the compound has formula Ih:

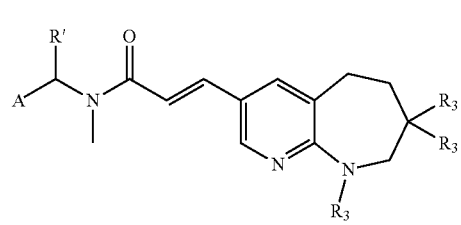

wherein,

R' and R₃ are as previously defined; and

A is:

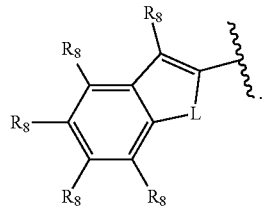

In a further embodiment, the present invention relates to compounds of formula Ih and the attendant definitions, wherein R' is H.

In a further embodiment, the present invention relates to compounds of formula Ih and the attendant definitions, wherein R₃ is H.

In a further embodiment, the present invention relates to compounds of formula Ih and the attendant definitions, wherein A is

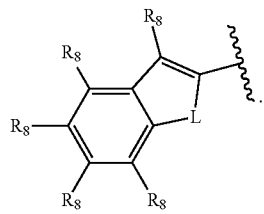

In a further embodiment, the present invention relates to compounds of formula Ih and the attendant definitions, wherein A is

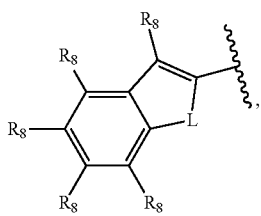

and L is O.

In a further embodiment, the present invention relates to compounds of formula Ih and the attendant definitions, wherein A is

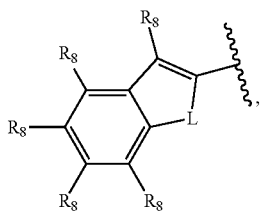

and L is S.

In a further embodiment, the present invention relates to compounds of formula Ih and the attendant definitions, wherein A is

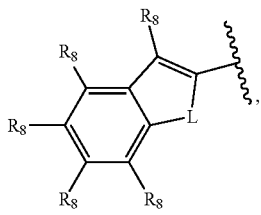

and $R_8$ is H or alkyl.

In a further embodiment, the present invention relates to compounds of formula I, wherein the compound has formula Ii:

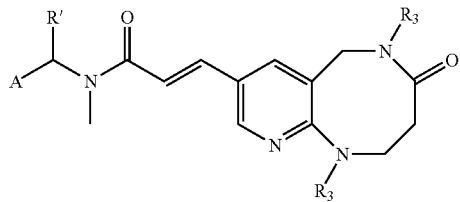

wherein,
R' and $R_3$ are as previously defined, and
A is:

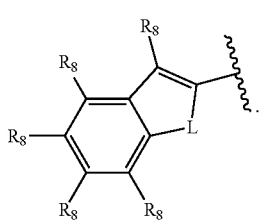

In a further embodiment, the present invention relates to compounds of formula Ii and the attendant definitions, wherein R' is H.

In a further embodiment, the present invention relates to compounds of formula Ii and the attendant definitions, wherein $R_3$ is H.

In a further embodiment, the present invention relates to compounds of formula Ii and the attendant definitions, wherein A is

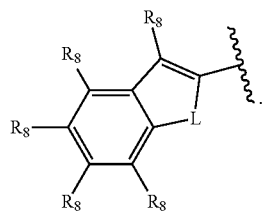

In a further embodiment, the present invention relates to compounds of formula Ii and the attendant definitions, wherein A is

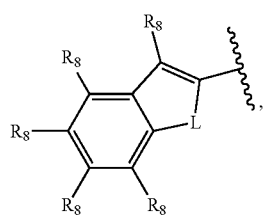

and L is O.

In a further embodiment, the present invention relates to compounds of formula Ii and the attendant definitions, wherein A is

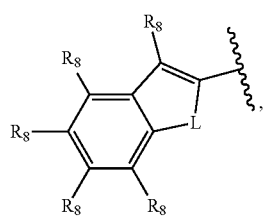

and L is S.

In a further embodiment, the present invention relates to compounds of formula Ii and the attendant definitions, wherein A is

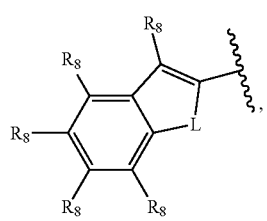

and $R_8$ is H or alkyl.

In a further embodiment, the present invention relates to compounds of formula I, wherein the compound has formula Ij:

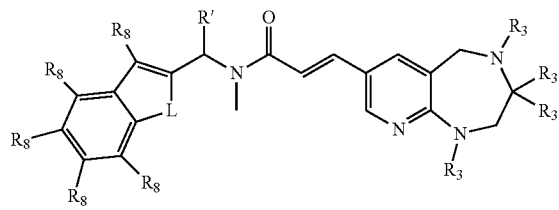

wherein,

R', $R_3$, $R_8$ and L are as previously defined.

In a further embodiment, the present invention relates to compounds of formula Ij and the attendant definitions, wherein L is O.

In a further embodiment, the present invention relates to compounds of formula Ij and the attendant definitions, wherein L is S.

In a further embodiment, the present invention relates to compounds of formula Ij and the attendant definitions, wherein R' is H.

In a further embodiment, the present invention relates to compounds of formula Ij and the attendant definitions, wherein $R_8$ is H or alkyl.

In a further embodiment, the present invention relates to compounds of formula Ij and the attendant definitions, wherein at least one $R_3$ is

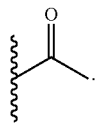 [SMILES: *C(C)=O]

In a further embodiment, the present invention relates to compounds of formula Ij and the attendant definitions, wherein at least one $R_3$ is

In a further embodiment, the present invention relates to compounds of formula Ij and the attendant definitions, wherein L is O, and $R_8$ is H or alkyl.

In a further embodiment, the present invention relates to compounds of formula Ij and the attendant definitions, wherein at each nitrogen bonded $R_3$ is H or alkyl.

In a further embodiment, the present invention relates to compounds of formula Ij and the attendant definitions, wherein each geminal $R_3$ is alkyl.

In a further embodiment, the present invention relates to compounds of formula Ij and the attendant definitions, wherein at least one $R_3$ is H.

In a further embodiment, the present invention relates to compounds of formula Ij and the attendant definitions, wherein the geminal $R_3$ are H and (R)-Me.

In a further embodiment, the present invention relates to compounds of formula Ij and the attendant definitions, wherein the geminal $R_3$ is H and (S)-Me.

In a further embodiment, the present invention relates to compounds of formula I, wherein the compound has formula Ik:

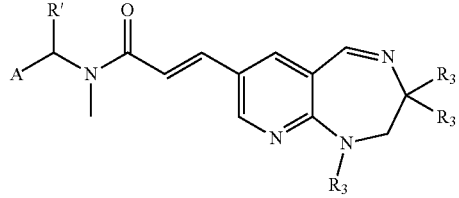

wherein,

R' and $R_3$ are as defined previously, and

A is:

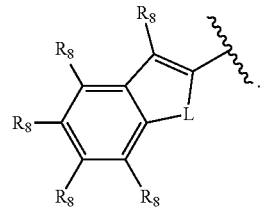

wherein $R_8$ and L are as defined previously.

In a further embodiment, the present invention relates to compounds of formula Ik and the attendant definitions, wherein R' is H.

In a further embodiment, the present invention relates to compounds of formula Ik and the attendant definitions, wherein A is

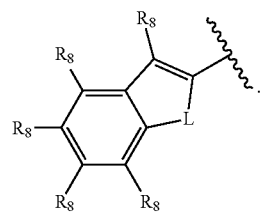

In a further embodiment, the present invention relates to compounds of formula Ik and the attendant definitions, wherein A is

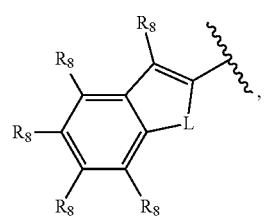

and L is O.

In a further embodiment, the present invention relates to compounds of formula Ik and the attendant definitions, wherein A is

[Structure: indole with R8 substituents and L]

an L is NMe.

In a further embodiment, the present invention relates to compounds of formula Ik and the attendant definitions, wherein A is

[Structure: benzofuran/benzothiophene-type with R8 substituents and L]

and R$_8$ is H or alkyl.

In a further embodiment, the present invention relates to compounds of formula I, wherein the compound has formula Il:

[Structure Il]

wherein,

R', R$_3$, R$_8$, and L are as previously defined.

In a further embodiment, the present invention relates to compounds of formula Il and the attendant definitions, wherein R$_3$ is H.

In a further embodiment, the present invention relates to compounds of formula Il and the attendant definitions, wherein L is O.

In a further embodiment, the present invention relates to compounds of formula Il and the attendant definitions, wherein R$_8$ is H or alkyl.

In a further embodiment the present invention relates to compounds of formula Il and the attendant definitions, wherein R$_3$ is H, L is O, and R$_8$ is H or alkyl.

In a further embodiment, the present invention relates to compounds of formula I, wherein the compound has formula Im:

[Structure Im]

wherein,

R', R$_3$, and R$_8$ are as previously defined.

In a further embodiment, the present invention relates to compounds of formula Im and the attendant definitions, wherein R' is H.

In a further embodiment, the present invention relates to compounds of formula Im and the attendant definitions, wherein the nitrogen bound R$_3$ is H.

In a further embodiment, the present invention relates to compounds of formula Im and the attendant definitions, wherein the geminal R$_3$ are H.

In a further embodiment, the present invention relates to compounds of formula Im and the attendant definitions, wherein L is O.

In a further embodiment, the present invention relates to compounds of formula Im and the attendant definitions, wherein R$_8$ is H or alkyl.

In a further embodiment the present invention relates to compounds of formula I, wherein the compound has formula In:

[Structure In]

wherein,

R', R$_2$ and R$_3$ are as defined previously, and

A is selected from the following:

[Structure: indole-type with R8 and L]

wherein R$_8$ and L are as defined previously.

In an embodiment, compounds of formula Io contemplated:

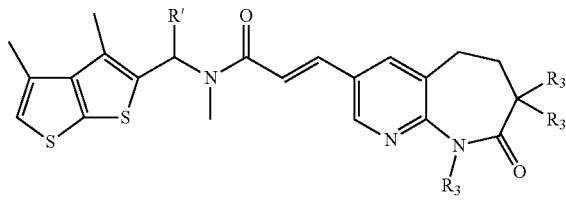

Io whre R' and R₃ are as previously defined.

In a further embodiment, the present invention relates to compounds of formula In and the attendant definitions, wherein R' is H.

In a further embodiment, the present invention relates to compounds of formula In and the attendant definitions, wherein R₃ is H.

In a further embodiment, the present invention relates to compounds of formula Im and the attendant definitions, wherein A is

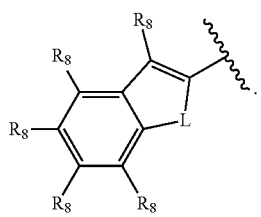

In a further embodiment, the present invention relates to compounds of formula In and the attendant definitions, wherein R₂ is phenyl.

In a further embodiment, the present invention relates to compounds of formula In and the attendant definitions, wherein A is

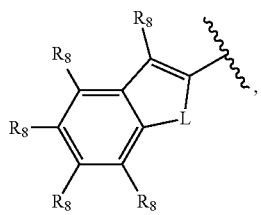

and L is N.

In a further embodiment, the present invention relates to compounds of formula In and the attendant definitions, wherein A is

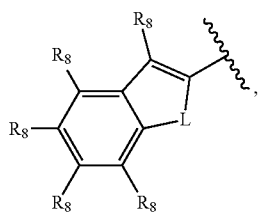

and R₈ is H or alkyl.

In a further embodiment, the present invention relates to compounds of formula In and the attendant definitions, wherein A is

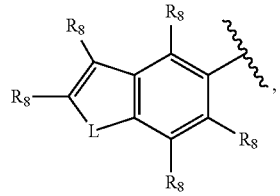

In a further embodiment, the present invention relates to compounds of formula In and the attendant definitions, wherein A is

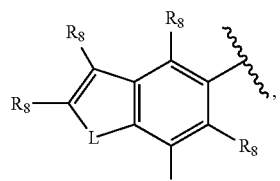

and L is NH.

In a further embodiment, the present invention relates to compounds of formula In and the attendant definitions, wherein A is

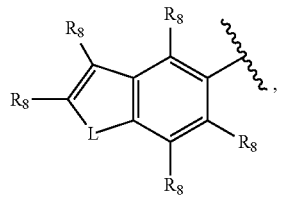

and R₈ is H or alkyl.

The present invention relates to, but is not limited to, the compounds wherein the compound is selected from the following list:
(E)-3-(7,7-Dimethyl-8-oxo-6,7,8,9-tetrahydro-5-oxa-1,9diaza-benzocyclohepten-3-yl)-N-(3-methoxy-2-propoxybenzyl)-N-methylacrylamide; (E)-3-(7,7-Dimethyl-6,7,8,9-tetrahydro-5-oxa-1,9-diaza-benzocyclohepten-3-yl)-N-methyl-N-(3-methyl-benzofuran-2-ylmethyl)acrylamide; 3-(7,7-dimethyl-8-oxo-6,7,8,9-tetrahydro-5-oxa-1,9-diaza-benzocyelohepten-3-yl)-N-methyl-N-[1-(R)-(3-methyl-benzofuran-2-yl)-ethyl)]acrylamide; (E)-3-(3,4-Dimethyl-2,3-dihydro-1H-pyrido[2,3-e][1,4]diazepin-7-yl)-N-methyl-N-(3-yl)-N-methyl-N-[1-(R)-(3-methyl-benzofuran-2-yl)-ethyl]acrylamide hydrochloride; (E)-3-(3,3-Dimethyl-2,3-dihydro-1H-pyrido[2,3-e][1,4]diazepin-7-yl)-N-methyl-N-(3-methylbenzofuran-2-ylmethyl)acrylamide; (E)-3-(3,4-Dimethyl-2,3-dihydro-1H-pyrido[2,3-e][1,4]diazepin-7-yl)-N-methyl-N-(3-methylbenzofuran-2-ylmethyl)acrylamide hydrochloride; (E)-7-{2-[Methyl-(3-methylbenzofuran-2-ylmethyl)carbamoyl]vinyl}-1,2,3,5-tetrahydropyrido[2,3-e][1,4]diazepine-4-carboxylic acid tert-butyl ester; (E)-3(4-Acetyl-2,3,4,5-tetrahydro-1H-pyrido[2,3-e][1,4]diazepin-7-yl)-N-methyl-N-(3-methylbenzofuran-2-ylmethyl)acrylamide hydrochloride; N-Methyl-N-(3-methylbenzofuran-2-ylmethyl)-3-(5,7,8,9-tetrahydro-6-oxa-1,9-diaza-benzocyclohepten-3-yl)-acrylamide; N-Methyl-N-(1-methyl-1H-indol-2-ylmethyl)-3-(5,7,8,9-tetrahydro-6-oxa-1,9-diaza-benzocyclohepten-3-yl)acrylamide: N-Methyl-N-(3-methyl-benzofuran-2-ylmethyl)-3-(4-methyl-2,3,4,5-tetrahydro-1H-pyrido[2,3-e][1,4]diazepin-7-yl)-acrylamode dihydrochloride: N-Methyl-N-(1-methyl-1H-indol-2-ylmethyl)-3-(4-methyl-2,3,4,5-tetrahydro-1H-pyrido[2,3-e][1,4]diazepin-7-yl)-acrylamide dihydrochloride: (E)-N-methyl-N-((3-methylbenzofuran-2-yl)methyl)-3-(6,7,8,9-tetrahydro-5H-pyrido[2,3-b]azepin-3-yl)acrylamide hydrochloride; (E)-N-methyl-N-((3-methylbenzo[b]thiphen-2-yl)methyl-3-(6,7,8,9-tetrahydro-5H-pyrido[2,3-b]azepin-3-yl)acrylamide hydrochloride; (E)-tert-butyl 7-(3-((1,2-dihydroacemaphthylen-5-yl)methyl)(methyl)amino)-3-oxoprop-1-enyl)-2,3-dihydro-1H-pyrido[2,3-e][1,4]diazepine-4(5H)-carboxylatel (S,E)-3-(3-benzyl-2,3,4,5-tetrahydro-1H-pyrido[2,3-e][1,4]diazepin-7-yl)-N-methyl-N-((3-methylbenzofuran-2-yl)methyl)acrylamide trifluoroacetate; (E)-N-methyl-N-((3-methylbenzo[b]thiphen-2-yl)methyl)-3-(2,3,4,5-tetrahydro-1H-pyrido[2,3-e][1,4]diazepin-7-yl)acrylamide hydrochloride; (E)-N-methyl-N-((3-methylbenzo[b]thiophen-2-yl)methyl-3-(2,3,4,5-tetrahydro-1H-pyrido[2,3-e][1,4]diazepin-7-yl)acrylamode hydrochloride; (E)-3-(3,3-dimethyl-2,3,4,5-tetrahydro-1H-pyrido[2,3-e][1,4]diazepin-7-yl)-N-methyl-N-((3-methyl-benzo[b]thiophen-2-yl)methyl)acrylamide hydrochloride; (E)-N-methyl-N-((3-methylbenzofuran-2-yl)methyl-3-(4-(methylsulfonyl)-2,3,4,5-tetrahydro-1H-pyrido[2,3-e][1,4]diazepin-7-yl)acrylamide hydrochloride; (E)-3-(3-spirocyclopentyl-2,3,4,5-tetrahydro-1H-pyrido[2,3-e][1,4]diazepin-7-yl)-N-methyl-N-((3-methylbenzofuran-2-yl)methyl)acrylamide trifluoroacetic acid; E)-N-methyl-3-((S)-3-methyl-2,3,4,5-tetrahydro-1H-pyrido[2,3-e][1,4]diazepin-7-yl)-N-((3-methyl-3a,7a-dihydrobenzofuran-2-yl)methyl)acrylamide trifluoroacetic acid; (R,E)-N-methyl-3-(3-methyl-2,3,4,5-tetrahydro-1H-pyrido[2,3-e][1,4]diazepin-7-yl)-N-((3-methylbenzofuran-2-yl)methyl)acrylamide trifluoroacetic acid salt; (E)-N-methyl-N-((3-methylbenzofuran-2-yl)methyl-3-(4-phenyl-2,3,4,5-tetrahydro-1H-pyrido[2,3-e][1,4]diazepin-7-yl)acrylamide; (E)-N-methyl-N-((3-methyl-1H-indol-2-yl)methyl-3-(1,2,3,5-tetrahydropyrido[2,3-e][1,4]oxazepin-7-yl)acrylamide; (E)-3-(2,2-dimethyl-3-oxo-3,4-dihydro-2H-pyrido[3,2-b][1,4]oxazin-7-yl)-N-methyl-N-((3-methyl-1H-indol-2-yl)methylacrylamide; (R,E)-(3,3-dimethyl-4-oxo-2,3,4,5-tetrahydropyrido[3,2-b][1,4]oxazepin-8-yl)-N-(3-ethylbenzofuran-2-yl)ethyl)-N-methylacrylamide; (E)-N-methyl-N-((3-methylbenzo[b]thiophen-2-yl)methyl-3-(4-oxo-1,2,3,4,5,6-hexahydropyrido[2,3-b][1,5]diazocin-8-yl)acrylamide, di-methane sulfonic salt; (E)-N-methyl-N-((3-methylbenzo[b]thiophen-2-yl)methyl-3-(4-oxo-1,2,3,4,5,6-hexahydropyrido[2,3-b][1,5]diazocin-8-yl)acrylamide, di-methane sulfonic salt; (R,E)-3-(3,3-dimethyl-2-oxo-1,2,3,5-tetrahydropyrido[2,3-e][1,4]oxazepin-7-yl)-N-(1-3-methoxy-2-propoxyphenyl)ethyl)-N-methylacrylamide; (E)-N-methyl-N-((3-methylbenzo[b]thiophen-2-yl)methyl)-3-(2,3,4,5-tetrahydro-1H-pyrido[2,3-b][1,4]diazepin-8-yl)acrylamide; (E)-N-methyl-3-(5-methyl-4-oxo-1,2,3,4,5,6-hexahydropyrido[2,3-b][1,5]diazocin-8-yl)-N-((3-methylbenzofuran-2-yl)methylacrylamide hydrochloride; (E)-N-(3-methoxy-2-propoxybenzyl)-N-methyl-3-(5-methyl-4-oxo-1,2,3,4,5,6-hexahydropyrido[2,3-b][1,5]diazocin-8-yl)acrylamide; (E)-N-methyl-3-(5-methyl-4-oxo-1,2,3,4,5,6-hexahydropyrido[2,3-b][1,5]diazocin-8-yl)-N-((3-methylbenzo[b]thiophen-2-yl)methyl)acrylamide; (E)-3-(5-hydroxy-8-oxo-6,7,8,9-tetrahydro-5H-pyrido[2,3-b]azepin-3-yl)-N-methyl-N-((3-methylbenzofuran-2-yl)methyl)acrylamide; (E)-3-(1,2,3,4,5,6-hexahydropyrido[2,3-b][1,5]diazocin-8-yl)-N-methyl-N-((3-methylbenzofuran-2-yl)methyl)acrylamide; (E)-3-((E)-2,2-dimethyl-3-(methylimino)-3,4-dihydro-2H-pyrido[3,2-b][1,4]oxazin-7-yl)-N-methyl-N-((3-methylbenzofuran-2-yl)methyl)acrylamide hydrochloride; (E)-3-((E)-2,2-dimethyl-3-(methylimino)-3,4-dihydro-2H-pyrido[3,2-b][1,4]oxazin-7-yl)-N-methyl-N-((3-methylbenzo[b]thiophen-2-yl)methyl)acrylamide; (E)-N-((1,3-dimethyl-1H-indol-2-yl)methyl)-N-methyl-3-(2-oxo-4-phenyl-2,3,4,5-tetrahydro-1H-pyrido[2,3-e][1,4]diazepin-7-yl)acrylamide; (E)-N-methyl-N-((3-methylbenzofuran-2-yl)methyl)-3-(2,3,4,5-tetrahydro-1H-pyrido[2,3-b][1,4]diazepin-8-yl)acrylamide.

Also included in the antibacterial compositions of the present invention are pharmaceutically acceptable addition salts and complexes of the FabI inhibitors. In cases wherein the inhibitors may have one or more chiral centers, unless specified, the present invention comprises each unique racemic compound, as well as each unique nonracemic compound.

In cases in which the inhibitors have unsaturated carbon-carbon double bonds, both the cis (Z) and trans (E) isomers are within the scope of this invention. In cases wherein inhibitors may exist in tautomeric forms, such as keto-enol tautomers, such as

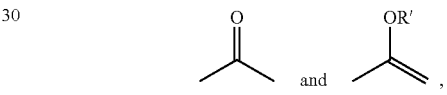

each tautomeric form is contemplated as being included within this invention, whether existing in equilibrium or locked in one form by appropriate substitution with R'. The meaning of any substituent at any one occurrence is independent of its meaning, or any other suhstituent's meaning, at any other occurrence.

Also included in the antibiotic compounds of the present invention are prodrugs of the FabI inhibitors.

A variety of subject compounds and intermediates of them may be made by a person of ordinary skill in the art using conventional reaction techniques. Non-limiting examples of compounds and methods of making them may be found in U.S. patent application Ser. Nos. 08/790,043, 10/009,219, 10/089,019, 09/968,129, 09/968,123, 09/968,236, 09/959,172, 09/979,560, 09/980,369, 10/089,755, 10/089,739, 10/089,740, and PCT Application Nos. PCT/US03/38706, WO 0027628 and WO 0210332.

Synthetic Routes to Compounds of Formula I

A generalized chemical approach to assembling compounds of formula I is based on viewing the analogs as consisting of a central ene-amide flanked by left-hand side (LHS) and right-hand side (RHS) moieties. Schematically, this is depleted in FIG. 2. Two possible bond disconnections envisioned in a retrosynthetic sense are shown with dashed lines. The examples illustrate some of the methods that can be used in the synthesis of compounds of formula I wherein the final covalent bond formed is via a Heck coupling between an alkene and a suitably halogenated right hand side moiety, or via a dehydrative coupling between a left hand side alkyl amine and an ene-carboxyilc acid. It will be recognixed by one skilled in the art that other disconnections are possible resulting in alternative modes of assembly of the compounds of the invention.

It will be recognized by one skilled in the art that other methods of LHS and RHS Synthesis can be employed in the preparation of said intermediates. Likewise other methods of amide and/or carbon-carbon bond formation may be used to assemble the compounds of the invention. It is also apparent that combinations of LHS and RHS other than those described above can be envisioned to prepare compounds falling within the scope of the invention as represented by formula I. These possibilities are futher detailed in the preparations and examples section to follow.

Acid addition salts of the compounds of formula I can be prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. This is illustrated by the preparation of hydrochloric acid salts as a final step in several of the general schemes shown above. Certain of the compounds form inner salts or zwitterions which may be acceptable. Cationic salts may be prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are some non-limiting examples of cations present n pharmaceutically acceptable salts.

Toxicology of Compounds

Acute toxicity can be assessed using increasing doses in mice and rodents. Exploratory acute toxicity in mice and/or rats after single dose may be undertaken to begin estimation of the therapeutic window of inhibitors and to identify the potential target organis of toxicity. As candidate selection nears, these studies may provide guidance for the selection of proper doses in multi-dose-studies, as well as establish any species specific differences in toxicities. These studies may be combined with routine PK measurements to assure proper dosages were achieved. Generally 3-4 doses will be chosen that are estimated to span a range having no effect through to higher doses that cause major toxic, but non-lethal, effects. Animals will be observed for effects on body weight, behavior and food consumption, and after euthanasia, hematology, blood chemistry, urinalysis, organ weight, gross pathology and histopathology will be undertaken.

Resistance Frequencies and Mechanism of Compounds

In vitro resistance frequencies in bacteria of interest can be estimated for compounds of formula I. Experiments can determine whether resistant isolates arise when challenged to grow on solid media at 1×, 2× and 4×MIC concentrations. For example with respect to S. aureus or E. coli, the experiments may use several recent clinical isolates of methicillin-sensitive and methicillin-resistant S. aureus and a laboratory strain of E. coli with acrA efflux pump defect. In addition, experiments may use several characterized triclosan-resistant S. aureus strains. The MICs of resistant strains isolated in this manner can then be determined. Subsequent experiments can determine whether resistant strains arise after serial passage of the strains in 0.5×MIC concentrations of each lead compound.

Mechanism of resistance may be determined in S. aureus laboratory strain, RN450 and in an E. coli laboratory strain carrying an acrA efflux pump mutation. Both high dose challenge (4×MIC) and sub-MIC serial passage may be used to obtain spontaneously arising resistant isolates. If no isolates are obtained with reasonable frequencies, chemical and physical mutagenesis methods can be used to obtain resistant isolates. The fabI gene from the chromosome of resistant isolates may be PCR amplified, then may be sequenced to determine whether changes in the FabI protein caused resistance. Triplicate PCR amplifications and sequences may be performed to assure that the observed sequence changes are correct, and did not arise from PCS errors during amplification. Strains carrying resistance mutations outside of the gene of interest may be documented and saved, characterized for their effects on susceptibilities of other antibiotics as evidence of possible efflux-mediated resistance mechanisms, characterized for their ability to alter compounds characterised for their effects on the expression of the specific mRNA and FabI protein.

Assays

Many different assay methods can be used to determine the activity of the compounds of the present invention. These assay methods include, for example, the following but also include other methods known to one of ordinary skill in the art.

S. aureus FabI Enzyme Inhibition Assay (NADH)

Assays are carried out in half-area, 96-well microtitre plates. Compounds are evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of S. aureus FabI. Inhibitors are typically varied over the range of 0.01-10 uM. The consumption of NADH is monitored for 20 minutes at 30° C. by following the change in absorbance at 340 nm. Initial velocities ate estimated from an exponential fit of the non-linear progress curves represented by the slope of the tangent at t=0 min. $IC_{50}$'s are estimated from a fit of the initial velocities to a standard, 4-pararmeter model and are typically reported as the mean±S.D. of duplicate determinations. Triclosan, a commercial antibacterial agent and inhibitor of FabI, may be included in an assay as a positive control. Compounds of this invention may have $IC_{50}$'s from about 5.0 micomolar to about 0.05 micromolar.

S. aureus FaBI Enzyme Inhibition Assay (NADPH) (Modified)

Assays are carried out in half-area, 96-well microtitre plates. Compounds are evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of S. aureus FabI. Inhibitors are typically varied over the range of 0.01-10 uM. The consumption of NADPH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

H. influenzae FaBI Enzyme Inhibition Assay

Assays are carried out in half-area, 96-well microtiter plates. Compounds are evaluated in 150-uL assay mixtures containing 100 mM, MES, 51 mM diethanolamine, 51 mM triethanolamine, pH 6.5 (MES=2-(N-morpholino)ethanesulfonic acid), 4% glycerol, 25 uM crotonoyl-ACP, 50 uM NADH, and an appropriate dilution of H. influenzae FabI (approximately 20 nM). Inhibitors are typically varied over the range of 0.01-10 uM. The consumption of NADH is monitored for 20 minutes at 30° C. by following the change in absorbance at 340 nm. Initial velocities are estimated from an exponential fit of the nou-linear progress curves. $IC_{50}$'s are estimated from a fit of the initial velocities to a standard, 4-parameter model, and are typically reported as the mean±S.D. of duplicate determinations. The apparent Ki is calculated assuming the inhibition is competitive with crotonoyl-ACP. A proprietary lead compound is eastrenfly included in all assays as a positive control.

E. coli FabI Enzyme Inhibition Assay

Assays are carried out in half-area, 96-well microtitre plates. Compounds are evaluated in 150-uL assay mixtures containing 100 mM NaADA, pH 6.5 (ADA=N-[2-acetamido]-2-iminodiacetic acid), 4% glycerol 0.25 mM crotonoyl CoA, 50 uM NADH, and an appropriate dilution of E. coli FabI. Inhibitors are typically varied over the range of 0.01-10 uM. The consumption of NADH is monitored for 20 minutes at 30° C. by following the change in absorbance at 340 mm. Initial velocities are estimated from an exponential fit of the non-linear progress curves represented by the slope of the tangent at t=0 min. $IC_{50}$'s are estimated from a fit of the initial velocities to a standard 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 100.0 micromolar to about 0.05 micromolar.

Preparation and Purification of Crotonoyl-ACP

Reactions contain 5 mg/mL E. coli apo-ACP, 0.8 mM crotonoyl-CoA (Fluka), 10 mM $MgCl_2$, and 30 uM S. pneumoniae ACP synthase in 50 mM NaHEPES, pH 7.5. The mixture is gently mixed on a magnetic stirrer at 23° C. for 2 hr, and the reaction is terminated by the addition of 15 mM EDTA and cooling on ice. The reaction mixture is filtered through a 0.2 micron filter (Millipore) and applied to a MonoQ column (Pharmacia) equilibrated with 20 mM Tris-Cl pH 7.5. The column is washed with buffer until all non-adherent material is removed (as observed by UV detection), and the crotonoyl-ACP is eluted with a linear gradient of 0 to 400 mM NaCl.

S. aureus FabI Enzyme Inhibition Assay Using Crotonoyl-ACP

Assays are carried out in half-area, 96-well microtitre plates. Compounds are evaluated in 100 uL assay mixtures containing 100 mM NaADA, pH 6.5 (ADA=N-(2-acetamido)-2-iminodiacetic acid), 4% glycerol, 25 nM crotonoyl-ACP, 50 uM NADPH, and an appropriate dilution of S. aureus Fab I (approximately 20 nM). Inhibitors are typically varied over the range of 0.01-30 uM. The consumption of NADPH is monitored for 30 minutes at 30° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 mierornolar to about 0.01 micromolar. The apparent Ki is calculated from Equation 2 assuming the inhibition is competitve with crotonoyl-ACP. More specifically, measured $IC_{50}$ values for 24 compounds of the present invention, as provided in the representative list above, ranged from less than about 0.02 μM to about 25 μM with 11 of these having an $IC_{50}$ of less than 1.

H. pylori FaBI Enzyme Inhibition Assay using Crotonoyl-ACP

Assays are carried out in half-area, 96-well microtitre plates. Compounds are evaluated in 100 uL assay mixttrres containing 100 mM NaADA, pH 6.5 (ADA=N-(2-acetamido)-2-immodiacetlc acid), 4% glycerol, 10 uM crotonoyl-ACP, 50 uM NADH, 100 mM ammonium acetate, and an appropriate dilution of H. pylori Fab I (approximately 15 nM). Inhibitors are typically varied over the range of 0.025-30 uM. The consumption of NADH is monitored for 30 minutes at 25° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent Ki is calculated from Equation 2 assuming the inhibition is competitve with crotonoyl-ACP.

$$v = \text{Range}/(1+[I]/IC50)s + \text{Background} \qquad \text{Equation 1}$$

$$Ki(\text{app}) = IC50/(1+[S]/Ks) \qquad \text{Equation 2}$$

Assays are carried out in half-area, 96-well microtitre plates. Compounds are evaluated in 100 uL assay mixtures containing 100 mM MES, 51 mM diethanolamine, 51 mM triethanolamine, pH 6.5 [MES=2-(N-morpholino)ethanesulfonic acid], 4% glycerol buffer, 100 mM $NH_4Cl$, 25 μM crotonoyl-ACP, 50 μM NADH, and 15 nM S. pneumoniae FabK. Inhibitors are typically varied over the range of 0.025-30 uM. The consumption of NADH is monitored for 30 minutes at 30° C. by following the change in absorbance at 340 nm. Initial velocities are estimated from a linear fit of the progress curves. $IC_{50}$'s are estimated from a fit of the initial velocities to a standard, 4-paramcter model (Equation 1) and are typically reported as the mean±S.D. of duplicate determinations. Compounds of this invention in this assay have $IC_{50}$'s fiord about 60.0 micromolar to about 0.01 micromolar. The apparent $K_i$ is calculated from Equation 2 assuming the inhibition is competitve with crotonoyl-ACP.

Antimicrobial Activity Assay

Whole-cell antimicrobial activity is determined by broth microdilution using the National Committee for Clinical Laboratory Standards (NCCLS) recommended procedure, Document M7-A5, "Methods for Dilution Susceptibility Tests for Bacteria that Grow Aerobically". The compound is tested in serial two-told dilutions ranging from 0.06 to 64 mcg/mL. A panel of 12 strains are evaluated in the assay. This panel consists of the following laboratory strains: Enterococcus faecalis 29-212, Staphylococcus aureus 29213, Staphylococcus aureus 43300, Moraxella catarrhalis 49143, Haemophilus influenzae 49247, Streptococcus pneumoniae 49619, Staphylococcus epidermidis 1024939, Staphylococcus epidermidis, 1024961, Escherichia coli AG100 (AcrAB+), Escherichia coli AG100A (AcrAB ), Pseudomonas aeruginosa K767 (MexAB+, OprM+), Pseudomonas aeruginosa K1119 (MexAB−, OprM−). The minimum inhibitory concentration (MIC) is determined as the lowest concentration of compound that inhibited visible growth. A spectrophotometer is used to assist in determining the MIC endpoint.

MIC assays may be performed using the microdilution method in a 96 well format. The assays may be performed in 96 well plates with a final volume of 100 μl cation-adjusted Mueller Hinton broth containing 2 fold serial dilutions of compounds ranging from 32 to 0.06 μg/ml. Bacterial growth may be measured at 600 nm using a Molecular Devices SpectraMax 340PC spectrophotometer. MICs can then be determined by an absorbance threshold algorithm and confirmed in some cases by inspecting the plates over a light box.

Minimum Bactericidal Concentration (MBC) may be determined by plating aliquots of MIC dilution series that did not show bacterial growth onto Petri plates containing appropriate semi-solid growth media. The lowest compound concentration that resulted in >99% killing of bacterial cells (relative to initial bacterial inocula in MIC test) is defined as the MBC.

Several strain panels may be used at various points in the compound progression Scheme. The primary panel may include single prototype strains of both community- and hospital-acquired pathogens for determining initial activities and spectra of activity. Secondary panel compositions will depend on the results of the primary panels, and will include 10-20 strains of relevant species that will include community acquired and antibiotic-resistant hospital acquired strains of *Staphylococcus aureus* and coagulase negative *Staphylcocci* together with other strains that are sensitive to the new compounds, and negative control strains. The secondary panels will be used during optimization of lead chemical series. Tertiary panels will include 100-200 clinical strains of *S. aureus* and coagulase negative *Staphylococci* together with other relevant strains as for the secondary panels. The tertiary panels will be utilized during the compound candidate selection stage and preclinical studies to generate bacterial population efficacy parameters such as $MIC_{50}$ and $MIC_{90}$.

Using the assay described above, measured MIC values against *Staphylococcus aureus* 29213 for 24 compounds of the present invention, as provided in the representative list above, ranged from less than about 0.06 µg/ml to greater than about 30 µg/ml with 9 of these compounds having an MIC of less than 1.

*Franciscella tularensis* in vitro Efficacy Studies

Routine MIC testing of *F. tularensis* may be undertaken on compounds that have demonstrated enzymatic activity inhibition against the *F. tularensis* FabI protein. The MIC testing of *F. tularensis* may be outsourced to a facility with BL3 capabilities, and with experience in handling *F. tularensis* cultures in the laboratory. The studies may be undertaken with the recommended methods tor antimicrobial susceptibility testing of *F. tularensis.*

*Helicobacter pylori* in vitro Efficacy Studies

Routine MIC testing of *H. pylori* may be undertaken on compounds that have demonstrated enzymatic activity inhibition against the *H. pylori* FabI protein. The studies may be undertaken with the recommended methods for antimicrobial susceptibility testing of *H. pylori.*

Cytotoxicity Assays

Cytotoxicity of the new compounds may be evaluated by the Alamar Blue assay according the manufacturers instructions. Human cell lines (e.g. Jurkat) grown in 96 well plates may be exposed to serial dilutions of the tested compounds. After adding Alamar Blue, cell viability may be determined by measuring the absorbance of the reduced and oxidized forms of Alamar Blue at 570 nm and 600 nm. Cytotoxicity may be reported as $LD_{50}$, the concentration that causes a 50% reduction in cell viability.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce file required dosage for any individual agent contained in the compositions (e.g., the FabI inhibitor) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the ceil culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Formulation

The antibacterial compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal, and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in m aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl, pyrrolidine, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl, alcohol, isopropyl alcohol, ethyl carbonate, ethyl acetate, benzyl alcohol, benzyl benzoate, propylene glycol 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propelkol) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional phannaoeutieally acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In certain embodiments, the subject compounds may be formulated as a tablet, pill capsule or other appropriate ingestible formulation (collectively hereinafter "tablet"), to provide a therapeutic dose in 10 tablets or fewer. In another example, a therapeutic dose is provided in 50, 40, 30, 20, 15, 10, 5 or 3 tablets.

In a certain embodiment, the antibacterial agent is formulated for oral administration as a tablet or an aqueous solution or suspension. In another embodiment of the tablet form of the antibacterial agent, the tablets are formulated such that the amount of antibacterial agent (or antibacterial agents) provided in 20 tablets, if taken together, would provide a dose of at least the median effective dose ($ED_{50}$), e.g., the dose at which at least 50% of individuals exhibited the quantal effect of inhibition of bacterial cell growth or protection (e.g., a statistically significant reduction in infection). In a further embodiment, the tablets are formulated such that the total amount of antibacterial agent (or antibacterial agents) provided in 10, 5, 2 or 1 tablets would provide at least an $ED_{50}$ dose to a patient (human or non-human mammal). In other embodiments, the amount of antibacterial agent (or antibacterial agents) provided in 20, 10, 5 or 2 tablets taken in a 24 hour time period would provide a dosage regimen providing, on average, a mean plasma level of the antibacterial agent(s) of at least the $ED_{50}$ concentration (the concentration for 50% of maximal effect of, e.g., inhibiting bacterial cell growth). In other embodiments less than 100 times, 10 times, or 5 times the ED50 is provided. In other embodiments, a single dose of tablets (1-20 tablets) provides about 0.25 mg to 1250 mg of an antibacterial agent(s).

Likewise, the antibacterial agents can be formulated for parenteral administration, as for example, for subcutaneous, intramuscular or intravenous injection, e.g., the antibacterial agent can be provided in a sterile solution or suspension (collectively hereinafter "injectable solution"). The injectable solution is formulated such that the amount of antibacterial agent (or antibacterial agents) provided in a 200 cc bolus injection would provide a dose of at least the median effective dose, or less than 100 times the $ED_{50}$, or less than 10 or 5 times the $ED_{50}$. The injectable solution may be formulated such that the total amount of antibacterial agent (or antibacterial agents) provided in 100, 50, 25, 10, 5, 2.5, or 1 cc injections would provide an $ED_{50}$ dose to a patient, or less than 100 times the $ED_{50}$ or less than 10 or 5 times the $ED_{50}$. In other embodiments, the amount of antibacterial agent (or antibacterial agents) provided in a total volume of 100 cc, 50, 25, 5 or 2 cc to be injected at least twice in a 24 hour time period would provide a dosage regimen providing, on average, a mean plasma level of the antibacterial agent(s) of at least the $ED_{50}$ concentration, or less than 100 times the $ED_{50}$, or less than 10 or 5 times the $ED_{50}$. In other embodiments, a single dose injection provides about 0.25 mg to 1250 mg of antibacterial agent.

Efficacy of Treatment

The efficacy of treatment with the subject compositions may be determined in a number of fashions known to those of skill in the art.

In one exemplary method, the median survival rate of the bacteria or bacteria median survival time or life span for treatment with a subject, composition may be compared to other forms of treatment with the particular FabI inhibitor, or with other antibiotic agents. The decrease in median bacteria survival rate or time or life span for treatment with a subject composition as compared to treatment with another method may be 10, 25, 50, 75, 100, 150, 200, 300, 400% even more. The period of time for observing any such decrease may be about 3, 5, 10, 15, 30, 60 or 90 or more days. The comparison may be made against treatment with the particular FabI inhibitor contained in the subject composition, or with other antibiotic agents, or administration of the same or different agents by a different method, or administration as part of a different drug delivery device than a subject composition. The comparison may be made against the same or a different effective dosage of the various agents. The different regiments compared may use measurements of bacterial levels to assess efficacy.

Alternatively, a comparison of the different treatment regimens described above may be based on the effectiveness of the treatment, using standard indicies for bacterial infections known to those of skill in the art. One method of treatment may be 10%, 20%, 30%, 50%, 75%, 100%, 150%, 200%, 300% more effective, than another method.

Alternatively, the different treatment regimens may be analyzed by comparing the therapeutic index for each of them, with treatment with a subject composition as compared to another regimen having a therapeutic index two, three, five or seven times that of, or even one, two, three or more orders of magnitude greater than, treatment with another method using the same or different FabI inhibitor.

As a non-limiting example, to determine if compounds are bactericidal or bacteriostatic at relevant concentrations, and to examine the kinetics of bacterial killing the following experiment may be performed with *S. aureus, S. epidermidis* and appropriate control strains and antibiotics. To fresh logarithmic cultures at $10^7$ viable cells/ml, compound may be added to reach concentrations of X1, X2 or X4 the MIC. Control cultures will receive no compound. At 1 hour intervals, aliquots will be diluted and plated for determining viable counts. Plots of viable cells vs. time for up to 24 hours will reveal bactericidal/bacteriostatic properties of the compounds, and also show the kill kinetics. These experiments are important to determine whether these inhibitors have time-dependent or concentration-dependent effects, and will be used to help set appropriate dosages in vivo in combination with pharmacokinetic and pharmacodynamic measurements.

In the practice of the instant methods, the antibacterial compositions of the present invention inhibit bacterial FabI with a $K_i$ of 5 µM or less, 1 µM or less, 100 nM or less, 10 nM or less or even 1 nM or less. In treatment of humans or other animals, the subject method may employ FabI inhibitors which are selective for the bacterial enzyme relative to the host animals' enoyl CoA hydratase, e.g., the $K_i$ for inhibition of the bacterial enzyme is at least one order, two orders, three orders, or even four or more orders of magnitude less than the $K_i$ for inhibition of enoyl CoA hydratase from the human (or other animal). That is, the practice of the subject method in vivo in animals utilizes FabI inhibitors with therapeutic indexes of at least 10, 100 or 1000.

Similarly, in the practice of the instant method, the antibacterial compounds of the present invention inhibit FabI with an $IC_{50}$ of 30 μM or less, 10 μM or less, 100 nM or less, or even 10 nM or less. In treatment of humans or other animals, the subject method may employ FabI inhibitors which are selective for the bacterial enzyme relative to the host animals' enoyl CoA hydratase, e.g., the $IC_{50}$ for inhibition of the bacterial enzyme is at least one order, two orders, three orders, or even four orders of magnitude less than the $IC_{50}$ for inhibition of enoyl CoA hydratase from the human (or other animal). That is, in preferred embodiments, the practice of the subject method in vivo animals utilizes FabI inhibitors with therapeutic indexes of at least 10, 100 or 1000.

Alternatively, bacterial inhibition by an antibacterial compound of the present invention may also be characterized in terms of the minimum inhibitory concentration (MIC), which is the highest concentration of compound required to achieve complete inhibition of bacterial cell growth. Such values are well known to those in the art as representative of the effectiveness of a particular antibacterial agent against a particular organism or group of organisms. In the practice of the instant methods, the antibacterial compositions of the present invention inhibit bacterial growth with MIC values of about 32 μg/mL, less than about 16 μg/mL, less than about 8 μg/mL, less than about 4 μg/mL, less than about 2 μg/mL, less than about 1 μg/mL, less man about 0.5 μg/mL, less than about 0.25 μg/mL, or even less than about 0.125 μg/mL. The value of MIC90, defined as the concentration of a compound required to inhibit the growth of 90% of bacterial strains within a given bacterial strain population, can also be used. In certain embodiments, the compounds of the present invention are selected for use based, inter alia, on having MIC90 values of less than about 32 μg/mL, less than about 16 μg/mL, less than about 8 μg/mL, less than about 4 μg/mL, less than about 2 μg/mL, less than about 1 μg/mL, less than about 0.5 μg/mL, less than about 0.25 μg/mL, or even less than about 0.125 μg/mL.

In other embodiments, the subject compounds are selected for use in animals, or animal cell/tissue culture based at least in part on having $LD_{50}$'s at least one order, or two orders, or three orders, or even four orders or more of magnitude greater than the $ED_{50}$. That is, in certain embodiments where the subject compounds are to be administered to an animal, a suitable therapeutic index is preferably greater than 10, 100, 1000 or even 10,000.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means Include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

The examples which follow are intended in no way to limit the scope of this invention but are provided to illustrate how to prepare and use compounds of the present invention. Many other embodiments of this invention will be apparent to one skilled in the art.

Exemplification

General

Proton nuclear magnetic resonance ($^1$H NMR) spectra were recorded at either 300 or 500 MHz, and chemical shifts are reported in parts per million (δ) downfield from the internal standard tetramethylsilane (TMS) or from deuterated solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. $CDCl_3$ is deuteriochloroform, DMSO-$d_6$ is hexadeuteriodimethylsulfoxide, $CD_3OD$ is tetradeuteriomethanol and $D_2O$ is deuterated oxide. Mass spectra were obtained using electrospray (ESI) ionization techniques. Flash chromatography was carried out on E. Merck Kieselgel 60 (230-400 mesh) silica gel. Analytical HPLC was performed on Varian chromatography systems. Celite® is a filter aid composed of acid-washed diatomaceous silica, and is a registered trademark of Manville Corp., Denver, Colo. General abbreviations are as follows: EDC=1-(3-dimethylaminopropyl)-3-ethylcarbodiimide hydrochloride, HOBt=1-hydroxybenzotriazole hydrate, (i-Pr)$_2$EtN=N,N-diisopropylethylame, DMF=N,N-dimethylformamide, MeOH=methanol, EtOH=ethanol, THF=tetrahydrofuran, DMSO=dimethylsulfoxide, Et$_2$O=diethyl ether, Ar=argon, Pd(OAc)$_2$palladium(II)acetate, P(o-tol)$_3$=tri-ortho-tolyphosphine, EtOAc=ethyl acetate, ACE-Cl=1-chloroethyl chloroformate, satd=saturated, Et$_3$N=triethylamine, TFA=trifluoroacetic acid, NaBH(OAc)$_3$=sodium triacetoxyborohydride, HOAc=acetic acid, EtCN=proprionitrile, CBzCl=benzyl chloroformate, MeCN=acetonitrile.

Example 1

Preparation of (E)-3-(7,7-Dimethyl-8-oxo-6,7,8,9-tetrahydro-5-oxa-1,9-diazabenzocyclohepten-3-yl)-N-(3-methoxy-2-propoxy-benzyl)-N-methylacrylamide

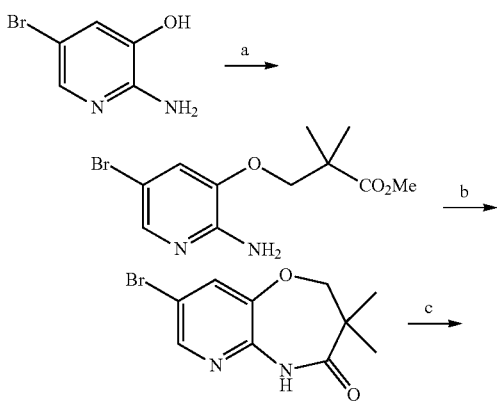

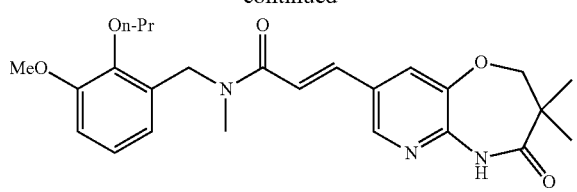

a) 2,2-dimethyl-3-hydroxypropionate, DEAD, PPh₃, THF, microwave; b) sodium hydride, DMSO; c) N-(3-methoxy-2-propoxy-benzyl)-N-methylacrylamide, Pd(OAc)₂, P(o-tol)₃, (i-Pr)₂EtN, EtCN, DMF.

a) 3-(2-Amimo-5-bromo-pyridin-3-yloxy)-2,2-dimethyl-propionic acid methyl ester

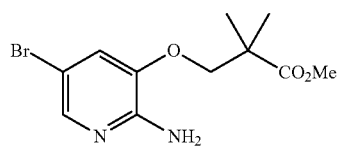

C₁₁H₁₅BrN₂O₃
Exact Mass: 302.03

To a suspension of 2-amino-5-bromopyridin-3-ol (1.42 g 7.51 mmol) in THF (40 mL) was added methyl 2,2-dimethyl-3-hydroxypropionate (1.2 mL, 9.0 mmol) and triphenyl phosphine (2.36 g, 9.00 mmol). The mixture was cooled to 0° C., then treated with diethyl diazodicarboxylate (1.70 g, 9.75 mmol). The mixture was heated in microwave at 120° C. for 20 min. The solvent was concentrated, and the residue was purified by chromatography (silica gel, hexanes/EtOAc, 75:25 to 60:40) to give the title compound (0.88 g, 39%) as a white solid: ¹H NMR (300 MHz, CDCl₃) δ7.73 (d, J=2.1 Hz, 1H), 7.02 (d, J=2.1 Hz, 1H), 4.65 (br s, 2H), 3.96 (s, 2H), 3.71 (s, 3H), 1.34 (s, 6H); ESI MS m/e 303 (M+H)⁺.

b) 3-Bromo-7,7-dimethy-6,7-dihydro-9H-5-oxa-1,9-diaza-benzocyclohepten-8-one

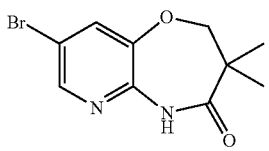

C₁₀H₁₁BrN₂O₂
Exact Mass: 270.00

To a solution of 3-(2-amino-5-bromo-pyridin-3-yloxy)-2,2-dimethylpropionic acid methyl ester (880 mg, 2.90 mmol) in DMSO (40 mL) was added NaH (60% in oil, 139-mg, 3.48 mmol), and the mixture was stirred overnight at room temperature. The mixture was diluted with water (100 mL), and further stirred for 15 min. The resulting precipitate was collected by filtration to give the title compound (600 mg, 76%) as a white solid: ¹H NMR (300 MHz, CDCl₃) δ8.34 (br s, 1H), 8.11 (d, J=1.8 Hz, 1H), 7.46 (d, J=1.8 Hz, 1H), 4.01 (s, 2H), 1.32 (s, 6H); ESI M Sm/e 271 (M+H)⁺.

c) (E)-3-(7,7-Dimethyl-8-oxo-6,7,8,9-tetrahydro-5-oxa-1,9-diaxa-benzocyclohepten-3-yl)-N-(3-methoxy-2-propoxy-benzyl)-N-methylacrylamide

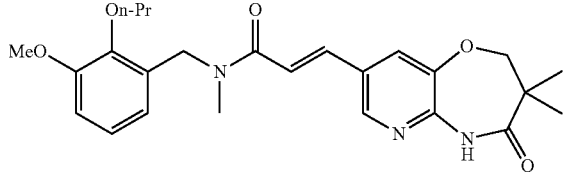

C₂₅H₃₁N₃O₅
Exact Mass: 453.23

To a solution of 3-bromo-7,7-dimethyl-6,7-dihydro-9H-5-oxa-1,9-diaza-benzocyclohepten-8-one (200 mg, 0.738 mmol) in propionitrile (24 mL) and DMF (6 mL) were added N-(3-methoxy-2-propoxy-benzyl)-N-methylacrylamide (253 mg, 0.959 mmol), (i-Pr)₂BtN (0.26 mL, 1.5 mmol), Pd(OAc)₂ (17 mg, 0.074 mmol) and P(o-tol)₃ (45 mg, 0.15 mmol), and the mixture was de-oxygenated with argon for 15 mm. The mixture was heated to reflux overnight, allowed to cool and then diluted with water (60 ml). The mixture was extracted with CH₂Cl₂ (3×50 mL). The combined extracts were washed with water and brine, dried (Na₂SO₄) and the solvent was removed in vacuo. Purification by column chromatography (silica gel, CH₂Cl₂/MeOH, 97:3) then by slow precipitation from CH₂Cl₂/hexanes gave the title compound (150 mg, 45%) as a pale-yellow solid and as a mixture of amide rotamers: ¹H NMR (300 MHz, DMSO-d₆) δ10.12-10.10 (m, 1H), 8.28-8.22 (m, 1H), 7.95-7.85 (m, 1H), 7.54-7.47 (m, 1H), 7.33-7.27 (m, 1H), 7.07-6.93 (m, 2H), 6.68-6.61 (m, 1H), 4.80-4.63 (m, 2H), 4.08-4.04 (m, 2H), 3.91-3.84 (m, 2H), 3.79 (s, 3H), 3.10-2.73 (m, 3H), 1.74-1.67 (m, 2H), 1.20-1.17 (m, 6H), 1.01-0.93 (m, 3H); MS (ESI) m/e 454 (M+H)⁺.

Example 2

Preparation of (E)-3-(7,7-Dimethyl-6,7,8,9-tetrahydro-5-oxa-1,9-diaza-benzocyclohepten-3-yl)-N-methyl-N-(3-methyl-benzofuran-2-ylmethyl)acrylamide

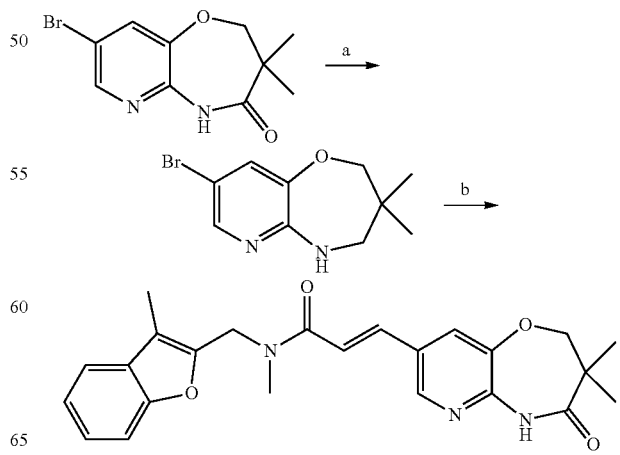

a) 1, BH3, THF; 2. NaOH, MeOH; b) N-methyl-N-(3-methyl-benzofuran-2-ylmethyl)acrylamide, Pd(OAc)2, P(o-tol)3. (i-Pr)2EtN, EtCN, DMF.

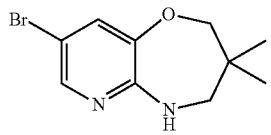

C₁₀H₁₃BrN₂O
Exact Mass: 256:02 a) 3-Bromoo-7,7-dimethyl-6,7,8,9-tetrahydro-5-oxa-1,9-diaza-benzocycloheptane

To a solution of 3-bromo-7,7-dimethyl-6,7-dihydro-9H-5-oxa-1,9-diaza-benzocyclohepten-8-one (620 mg, 2.28 mmol) in THF (15 mL) was added BH3 (9.1 mL of a 1 M solution in THF, 9.1 mmol), and the mixture was heated to reflux overnight. After cooling, the solvent was removed in vacuo. The residue was dissolved in MeOH (15 mL) and 2 N NaOH (5 mL), and the mixture was heated to reflux for 4 h. Methanol was then removed in vacuo and the resulting precipitate was collected, by filtration to give the title compound (260 mg, 44%) as a white solid: $^1$H NMR (300 MHz, CDCl$_3$) δ7.78 (d, J=1.8 Hz, 1H), 7.19-7.18 (m, 1H), 4.60 (br s, 1H), 3.83 (s, 2H), 3.10 (d, J=3.9 Hz, 2H), 1.03 (s, 6H); ESI MS m/e 257 (M+H)$^+$.

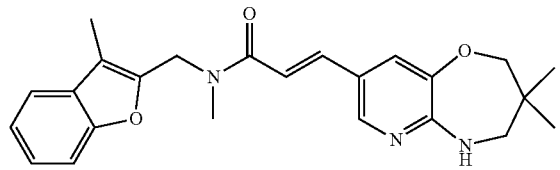

C₂₄H₂₇N₃O₃
Exact Mass: 405:21 b) (E)-3-(7,7-Dimethyl-6,7,8,9-tetrahydri-5-oxa-1,9-diaza-benzocyclohepten-3-yl)-n-methyl-N-(3-methyl-benzofuran-2-ylmethyl)acrylamide.

To a solution of 3-bromo-7,7-dimethyl-6,7,8,9-tetrahydro-5-oxa-1,9-diaza-benzocycloheptene (250 mg, 0.972 mmol) in propionitrile (24 mL) and DMF (6 mL) were added N-methyl-N-(3-methyl-benzofuran-2-ylmethyl)acrylamide (290 mg, 1.26 mmol), (i-Pr)2EtN (0.34 mL, 1.94 mmol), Pd(OAc)2 (22 mg, 0.097 mmol) and P(o-tol)3 (59 mg, 0.19 mmol), and the mixture was de-oxygenated with argon for 15 min. The mixture was heated to reflux overnight, allowed to cool and then diluted with water (60 mL). The mixture was extracted with CH2Cl2 (3×50 mL). The combined extracts were washed with water and brine, dried (Na2SO4) and the solvent was removed in vacuo. Purification by column chromatography (silica gel, CH2Cl2/MeOH, 97:4) and then by slow precipitation from CH2Cl2/hexanes gave the title compound (60 mg, 15%) as a pale yellow solid and as a mixture of amide rotamers: $^1$H NMR (300 MHz, DMSO-d$_6$) δ7.92 (s, 1H), 7.60-7.55 (m, 2H), 7.50-7.38 (m, 2H), 7.31-6.96 (m, 3H), 6.68-6.65 (m, 1H), 4.96-4.76 (m, 2H), 3.77 (s, 2H), 3.15-2.91 (m, 5H), 2.26 (s, 3H), 0.96 (s, 6H); MS (ESI) m/e 406 (M+H)+.

Example 3

Preparation of 3-(7,7-dimethyl-8-oxa-6,7,8,9-tetrahydro-5-oxa-1,9-diaza-benzocyclohepten-3-yl)-N-methyl-N-[1-(R)-(3-methyl-benzofuran-2-yl)-ethyl]acrylamide

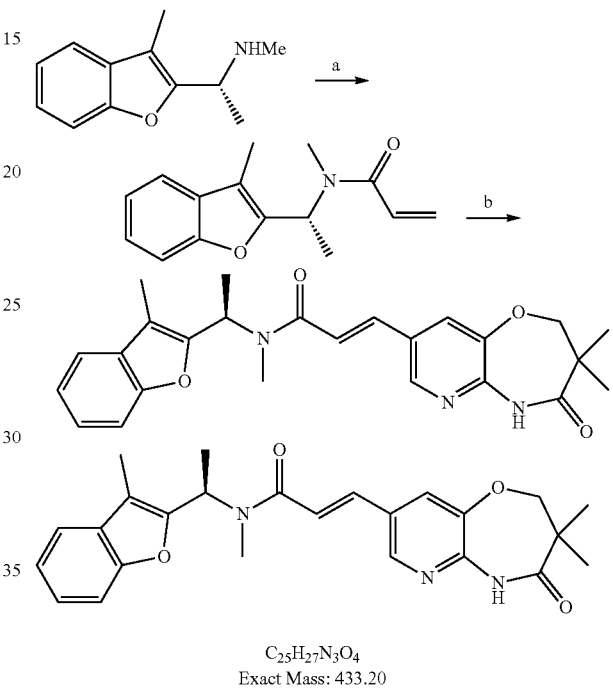

C₂₅H₂₇N₃O₄
Exact Mass: 433.20 a) acryloyl chloride, Et₃N, DMF; b) 3-bromo-7,7-dimethy-6,7-dihydro-9H-5-oxa-1,9-diaza-benzocyccohepten-8-one, Pd(OAc)2, P(o-tol)3, (i-Pr)2EtN, EtCN, DMF

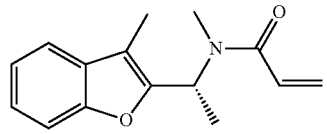

C₁₅H₁₇NO₂
Exact Mass: 243:13 a) (R)—N-methyl-N-[1-(3-methyl-benzofuran-2-yl)-ethyl]acrylamide

To an ice cold mixture of (R)-methyl-[1-(3-methyl-benzofuran-2-yl)-ethyl]amine (7.5 mL of a 0.46 M solution in DMF, 3.5 mmol) and Et3N (0.6 mL, 4.1 mmol) was added acryloyl chloride (0.3 mL, 3.8 mmol) drop-wise. The mixture was slowly warmed to room temperature and stirred overnight. The mixture was diluted with H₂O and extracted with Et2O (3×). The combined organics were washed with H2O and satd NaCl, dried (Na2SO4) and concentrated. Purification by column chromatography (silica, gel, 7:3 hexanes/EtOAc) gave the title compound (630 mg, 75%) as a yellow oil: 1H NMR (300 MHz, DMSO-d$_6$) δ7.50-7.47 (m, 1H), 7.44-7.41 (m, 1H), 7.30-7.20 (m, 2H), 6.81-6.52 (m, 1H), 6.40-6.25 (m, 2H), 5.74-5.70 (m, 1H), 2.99-2:90 (m, 3H), 2.23 (s, 3H), 1.69-1.58 (m, 3H).

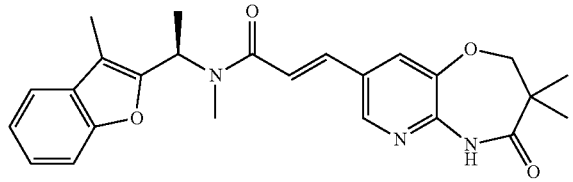

C$_{25}$H$_{27}$N$_3$O$_4$
Exact Mass: 433.20 b) 3-(7,7-dimethyl-8-oxo-6,7,8,9-tetrahydro-5-oxa-1,9-diaza-benzocyclohepten-3-yl)-N-methyl-N-[1-(R)-(3-methyl-benzofuran-2-yl)-ethyl]acrylamide A suspension of (R)—N-methyl-N-[1-(3-methyl-benzofuran-2-yl)-ethyl]acrylamide (328 mg, 1.35 mmol), 3-bromo-7,7-dimethyl-6,7-dihydro-9H-5-oxa-1,9-diaza-benzocyclohepten-8-one (400 mg, 1.48 mmol), (o-tol)3P (1.32 mg, 0.43 mmol) and DIEA (0.3 mL, 1.6 mmol) in EtCN (10 mL) and DMF (5 mL) was deoxygenated with argon for 30 min. Pd(OAc)2 (50 mg, 0.22 mmol) was added, the mixture was deoxygenated again with argon for 20 min and the mixture was heated to reflux overnight. The mixture was cooled to room temperature and partitinned between EtOAc and water. The residue was suspended in Et2O and then sonicated to give a solid. The solid was collected by filtration. Purification by column chromatography (silica gel, 1:1 hexanes/EtOAc) and sonication in Et2O gave the title compound (150 mg, 26%) as a white solid: $^1$H NMR (300 MHz, DMSO-d$_6$) δ10.13 (s, 1H), 8.27 (s, 1H), 8.0.1-7.89 (m, 1H), 7.58-7.50 (m, 3H), 7.32-7.18 (m, 3H), 6.19-5.99 (m, 1H), 4.07 (s, 2H), 3.04-2.79 (m, 3H), 248 (s, 3H), 1.64-1.54 (m, 3H), 1.19 (s, 6H); MS (ESI) m/e 434 (M+H)+.

Example 4

Preparation of (E)-3-(3,3-Dimethyl-2,3-dihydro-1H-pyrido[2,3-e][1,4]diazepin-7-yl)-N-methyl-N-(3-methylbenzofuran-2-ylmethyl)acrylamide

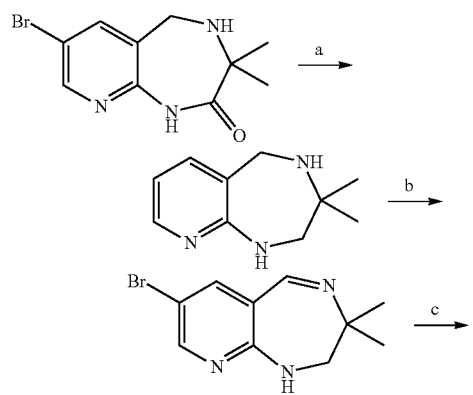

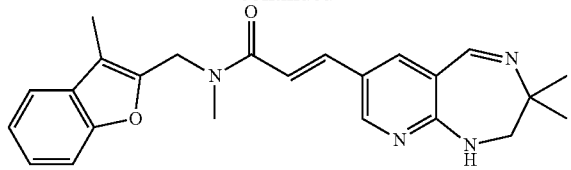

a) LiAlH$_4$, THF; b) Br$_2$, DMF; c) N-methyl-N-(3-methylbenzofuran-2-ylmethyl)acrylamide, Pd(OAc)$_2$, P(o-tol)$_3$, (i-Pr)$_2$EtN, EtCN, DMF

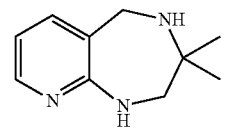

C$_{10}$H$_{15}$N$_3$
Exact Mass: 177.13
Mol. Wt.: 177:25 a) 3,3-Dimethyl-2,3,4,5-tetrahydro-1H-pyrido[2,3-e][1,4]diazepine

A suspension of 7-bromo-3,3-dimethyl-1,3,4,5-tetrahydropyrido[2,3-e][1,4]diazepin-2-one (0.50 g, 1.8 mmol) in THF (15 mL) was cooled in an ice bath and treated dropwise with LiAlH$_4$ (4.1 mL of a 1.0 M solution in THF, 4.1 mmol). After stirring for 30 mm, the ice bath was removed and the solution was allowed to warm to room temperature. After heating to reflux overnight, the mixture was cooled in an ice bath. The reaction was quenched sequentially with H$_2$O (0.15 mL), 15% NaOH (0.15 mL) and H$_2$O (0.45 ml). After 5 min, the ice bath was removed and the mixture was stirred at room temperature for 1.5 h. The mixture was filtered through Celite, and the filtrate was concentrated in vacuo to give the title compound (0.43 g; quantitative) as a white solid; $^1$H NMR (300 MHz, CDCl$_3$) δ7.90 (dd, J=4.9, 1.5 Hz, 1H), 7.17 (d, J=7.2 Hz, 1H), 6.61 (dd, J=7.2, 4.9 Hz, 1H), 4.85 (br s, 1H), 3.91 (s, 2H), 3.22 (d, J=4.5 Hz, 2H), 2.39 (br s, 1H), 1.20 (s, 6H); MS (ESI) m/e 178 (M+H)$^+$.

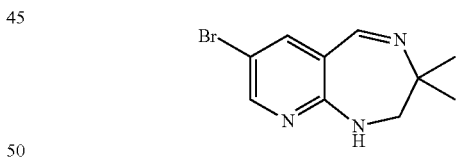

C$_{10}$H$_{12}$BrN$_3$
Exact Mass: 253.02
Mol. Wt.: 254.13 b) 7-Bromo-3,3-dimethyl-2,3-dihydro-1H-[2,3-e][1,4]diazepine

A solution of 3,3-dimethyl-2,3,4,5-tetrahydro-1H-pyrido[2,3-e][1,4]diazepine (0.43 g. 1.8 mmol) in DMF (20 mL) was cooled in an ice bath and treated drop-wise with Br$_2$ (0.19 mL, 3.7 mmol). After stirring in the ice bath for 2.5 h, the reaction was quenched with H$_2$O (25 mL) and NaHCO (50 mL) and extracted with EtOAc (3×100 mlL). The combined organic layers were washed with H$_2$O (2×50 mL) and brine (50 mL), dried over Na$_2$SO$_4$, filtered and concentrated to an orange oil. Purification by flash column chromatography (silica gel, CH$_2$Cl$_2$/MeOH, 98:2 to 96:4) gave the title compound (0.26 g, 54%) as a yellow solid: ¹H NMR (300 MHz, DMSO-d$_6$) δ8.15 (d, J=2.3 Hz, 1H), 8.03 (s, 1H), 7.73 (d, J=2.3 Hz, 1H), 5.93 (br s, 1H), 3.09 (d, J=4.9 Hz, 2H), 1.30 (s, 6H); MS (ESI) m/e 254 (M+H)⁺.

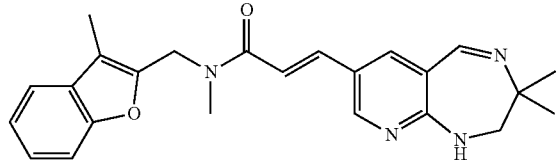

C$_{24}$H$_{26}$N$_4$O$_2$
Exact Mass: 402.21
Mol. Wt.: 402.49 c) (E)-3-(3,3-Dimethyl-2,3-dihydro-1H-pyrido[2,3-e][1,4]diazepin-7-yl)-N-methyl-N-(3-methylbenzofuran-2-ylmethyl)acrylamide A suspension of 7-bromo-3,3-dimethyl-2,3-dihydro-1H-pyrido[2,3-e][1,4]diazepine (255 mg, 1.00 mmol) and N-methyl-N-(3-methylbenzofuran-2-ylmethyl)acrylamide (0.28 g, 1.2 mmol) in propionitrile (5.0 mL) and DMF (1.3 mL) was de-oxygenated with Ar for 10 min. The mixture was treated with (i-Pr)$_2$EtN (0.38 mL, 2.2 mmol) and was de-oxygenated with Ar for 5 min. Pd(OAc)$_2$ (22 mg, 0.10 mmol) and P(o-tol)$_3$ (63 mg, 0.21 mmol) were added simultaneously, and the mixture was de-oxygenated a third time for 5 min. The mixture was heated to reflux overnight, then allowed to cool. The mixture was diluted with EtOAc (50 mL) and washed with H$_2$O (25 mL). The organic layer was dried over Na$_2$SO$_4$, filtered and concentrated to an orange oil. Purification by flash column chromatography (silica gel, CH$_2$Cl$_2$/MeOH, 96:4) followed by trituration with Et$_2$O gave the title compound (85 mg, 21%) as a yellow powder and as a mixture of amide rotamers: ¹H NMR (300 MHz, DMSO-d$_6$) δ8.44-8.43 (m, 1H), 8.25 (s, 1H), 8.19-8.15 (m, 1H), 8.06 (s, 1H), 7.58-7.08 (m, 6H), 4.99-4.79 (m, 2H), 3.18-2.92 (m, 5H), 2.27 (s, 3H), 1.16 (s, 6H); MS (ESI) m/e 403 (M+H)⁺.

Example 5

Preparation of (E)-3-(3,3-Dimethyl-2,3-dihydro-1H-pyrido[2,3-e][1,4]diazepin-7-yl)-N-methyl-N-(3-methylbenzofuran-2-ylmethyl)acrylamide hydrochloride

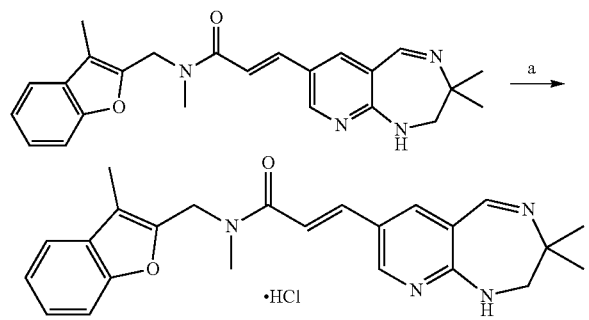

a) HCl in Et$_2$O, CH$_2$Cl$_2$

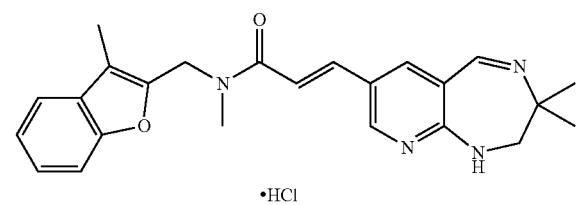

C$_{24}$H$_{27}$ClN$_4$O$_2$
Exact Mass: 438.18
Mol. Wt.: 438.95 a) (E)-3-(3,3-Dimethyl-2,3-dihydro-1H-pyrido[2,3-e][1,4]diazepin-7-yl)-N-methyl-N-(3-methylbenzofuran-2-ylmethyl)acrylamide hydrochloride A solution of (E)-3-(3,3-dimethyl-2,3-dihydro-1H-pyrido[2,3-e][1,4]diazepin-7-yl)-N-methyl-N-(3-methylbenzofuran-2-ylmethyl)acrylamide (0.11 g, 0.27 mmol) in CH$_2$Cl$_2$ (10 mL) was treated with anhydrous HCl (0.27 mL of a 1.0 M solution in Et$_2$O, 0.27 mmol). After stirring for 15 min, the mixture was diluted with Et$_2$O (50 mL) and allowed to stir for 3 h. The solid was isolated by filtration, washed with Et$_2$O, and dried under vacuum at 50° C. overnight to give the title compound (0.10 g, 86%) as a yellow powder and as a mixture of amide rotamers: ¹H NMR (300 MHz, DMSO-d$_6$) δ13.16-13.13 (m, 1H), 9.67-9.65 (m, 1H), 8.96-8.92 (m, 1H), 8.69 (s, 1H), 8.64-8.61 (m, 1H), 7.58-7.24 (m, 6H), 5.00-4.80 (m, 2H), 4.54 (br s, 2H), 3.19-2.92 (m, 3H), 2.27 (s, 3H), 1.36 (br s, 6H); MS (ESI) m/e 403 (M+H)⁺.

Example 6

Preparation of (E)-7-{2-[Methyl-(3-methylbenzofuran-2-ylmethyl)carbamoyl]vinyl}-1,2,3,5-tetrahydropyrido[2,3-e][1,4]diazepine-4-carboxylic acid tert-butyl ester

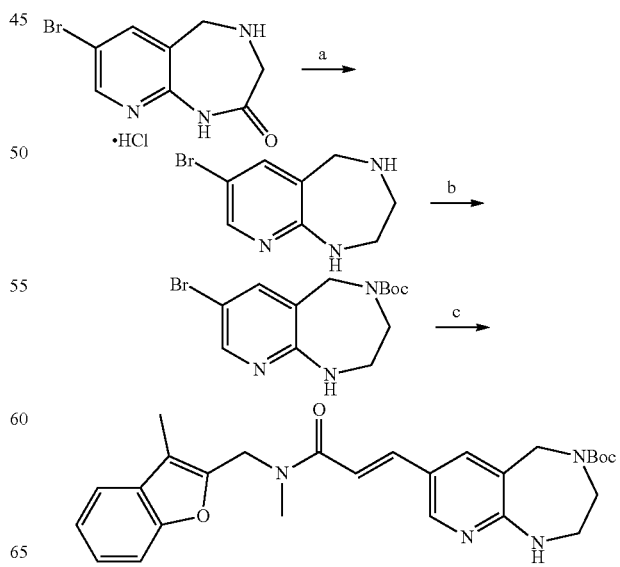

a) LiAlH₄, THF; b) (Boc)₂O, Et₃N, CH₂Cl₂; c) N-methyl-N-(3-methylbenzofuran-2-ylmethyl)acrylamide, Pd(OAc)₂, P(o-tol)₃, (i-Pr)₂EtN, EtCN, DMF

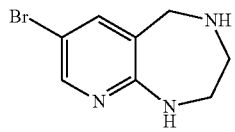

C₈H₁₀BrN₃
Exact Mass: 227.01
Mol. Wt.: 228.09 a) 7-Bromo-2,3,4,5-tetrahydro-1H-pyrido[2,3-e][1,4]diazepine

A suspension of 7-bromo-1,3,4,5-tetrahydro-pyrido[2,3-e][1,4]diazepin-2-one hydrochloride (1.16 g, 4.16 mmol) in THF (35 ml) was cooled in an ice bath and treated dropwise with LiAlH₄ (8.4 mL of a 1.0 M solution in THF, 8.4 mmol). After stirring for 30 min, the ice bath was removed and the solution was allowed to warm to room temperature. After heating to reflux overnight, the mixture was cooled in an ice bath. The reaction was quenched sequentially with H₂O (0.3 mL), 15% NaOH (0.3 mL) and H₂O (0.9 mL). After 5 min, the ice bath was removed and the mixture was stirred at room temperature for 2.5 h. The mixture was filtered through Celite, and the filtrate was concentrated in vacuo to give a yellow syrup. Purification by flash column chromatography (silica gel, CH₂Cl₂/MeOH, 95:5 to 90:10) gave the title compound (0.42 g, 44%) as a white solid: ¹NMR (300 MHz, CDCl₃) δ 8.03 (d, J=2.3 Hz, 1H), 7.44 (d, J=2.0 Hz, 1H), 4.96 (br s, 1H), 3.82 (s, 2H), 3.22-3.15 (m, 2H), 3.08-3.05 (m, 2H), 1.97 (br s, 1H); MS (ESI) m/e 228 (M+H)⁺.

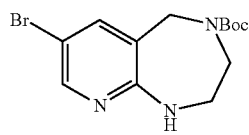

C₁₃H₁₈BrN₃O₂
Exact Mass: 327.06
Mol. Wt.: 328.20 b) 7-Bromo-1,2,3,5-tetrahydro-pyrido[2,3-e][1,4]diazepine-4-carboxylic acid tert-butyl ester A solution of 7-bromo-2,3,4,5-tetrahydro-1H-pyrido[2,3-e][1,4]diazepine (0.42 g, 1.8 mmol) in CH₂C₂ (20 mL) was treated with Et₃N (0.34 mL, 2.4 mmol) followed by di-tert-butyl-dicarbonate (0.44 g, 2.0 mmol). After stirring for 1 h, the reaction was concentrated to a white solid. Purification by flash column chromatography (silica gel, CH₂Cl₂/MeOH, 99:1) gave the title compound (0.55 g, 91%) as a white solid and as a mixture of rotamers: ¹NMR (300 MHz, CDCl₃) δ 8.06 (s, 1H), 8.59-8.45 (m, 1H), 4.90 (s, 1H), 4.35-4.27 (m, 2H), 3.66-3.65 (m, 2H), 3.29-3.24 (m, 2H), 1.42 (s, 9H); MS (ESI) m/e 328 (M+H)⁺.

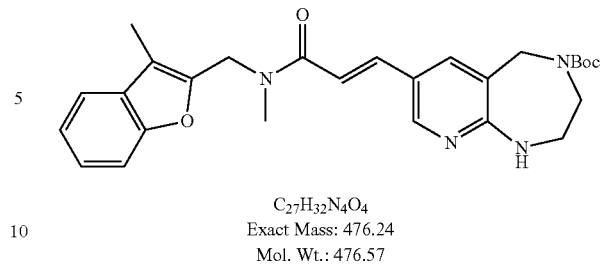

C₂₇H₃₂N₄O₄
Exact Mass: 476.24
Mol. Wt.: 476.57 c) (E)-7-{2-[Methyl-(3-methylbenzofuran-2-ylmethyl)carbamoyl]vinyl}-1,2,3,5-tetrahydro-pyrido[2,3-e][1,4]diazepine-4-carboxylic acid tert-butyl ester A solution of 7-bromo-1,2,3,5-tetrahydro-pyrido[2,3-e][1,4]diazepine-4-carboxylic acid tert-butyl ester (0.53 g, 1.6 mmol) and N-methyl-N-(3-methylbenzofuran-2-ylmethyl)acrylamide (0.41 g, 1.8 mmol) in propionitrile (8.0 mL) and DMF (2.0 mL) was de-oxygenated with Ar for 10 min. The mixture was treated with (i-Pr)₂EtN (0.62 mL, 3.5 mmol) and was de-oxygenated with Ar for 5 min. Pd(OAc)₂ (36 mg, 0.16 mmol) and P(o-tol)₃ (100 mg, 0.33 mmol) were added simultaneously, and the mixture was de-oxygenated a third time for 10 min. The mixture was heated to reflux tor 6 h, then allowed to cool. The mixture was diluted with EtOAc (100 mL) and washed with H₂O (50 mL). The organic layer was dried over Na₂SO₄, filtered and concentrated to an orange oil. Purification by flash column chromatography (silica gel, CH₂Cl₂/MeOH, 98:2) gave the title compound (0.48 g, 62%) as a white powder and as a mixture of amide rotamers: ¹H NMR (300 MHz, DMSO-d₆) δ 8.15-8.10 (m, 1H), 7.87-7.74 (m, 1H), 7.57-7.42 (m, 3H), 7.32-0.77 (m, 4H), 4.97-4.78 (m, 2H), 4.51-4.42 (m, 2H), 3.59-3.57 (m, 2H), 3.43-3.41 (m, 2H), 3.1-2.92 (m, 3H), 2.26 (s, 3H), 1.38-1.24 (m, 9H); MS (ESI) m/e 477 (M+H)⁺.

Example 6

Preparation of (E)-N-Methyl-N-(3-methylbenzofuran-2-ylmethyl)-3-(2,3,4,5-tetrahydro-1H-pyrido[2,3-e][1,4]diazepin-7-yl)acrylamide hydrochloride

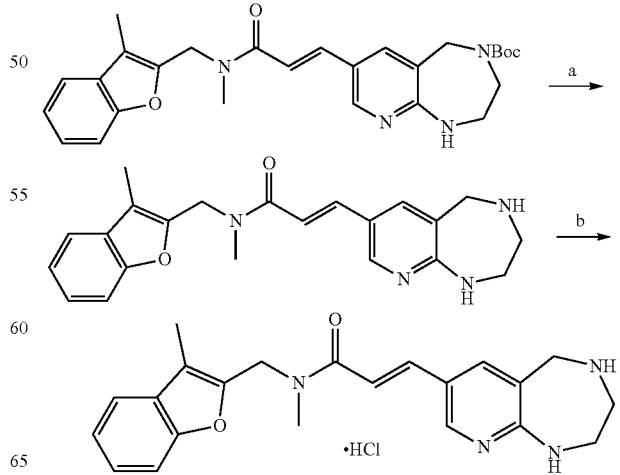

a) TFA, CH$_2$Cl$_2$; b) HCl in Et$_2$O, CH$_2$Cl$_2$

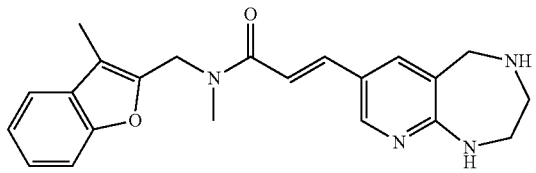

C$_{22}$H$_{24}$N$_4$O$_2$
Exact Mass: 376.19
Mol. Wt.: 376.45 a) (E)-N-Methyl-N-(3-methylbenzofuran-2-ylmethyl)-3-(2,3,4,5-tetrahydro-1H-pyrido[2,3-e][1,4]diazepin-7-yl)acrylamide A solution of (E)-7-{2-[methyl-(3-methylbenzofuran-2-ylmethyl)carbamoyl]vinyl}-1,2,3,5-tetrahydro-pyrido[2,3-e][1,4]diazepine-4-carboxylic acid tert-butyl ester (0.38 g, 0.80 mmol) in CH$_2$Cl$_2$ (4 mL) was cooled in an ice bath and then treated with TFA (4 mL). After stirring for 2 h, the mixture was concentrated under vacuum. The residue was treated with saturated NaHCO$_3$ (25 mL) and extracted with CH$_2$Cl$_2$/MeOH (4×=mL of a 98:2 mixture). The combined organic layers were dried over Na$_2$SO$_4$, filtered and concentrated to a light yellow solid. Purification by flash column chromatography (silica gel, CH$_2$Cl$_2$/MeOH, 92:8) gave the title compound (0.21 g, 70%) as a white powder and as a mixture of amide rotamers: $^1$H NMR (300 MHz, DMSO-d$_6$) δ8.14 (br s, 1H), 7.68-7.63 (m, 1H), 7.50-7.40 (m, 3H), 7.26-7.20 (m, 2H), 7.04-6.72 (m, 1H), 5.10 (s, 1H), 4.83-4.72 (m, 2H), 3.89 (s, 2H), 3.30-3.26 (m, 2H), 3.22-3.04 (m, 5H), 2.31 (s, 3H), 1.70 (br s, 1H); MS (ESI) m/e 377 (M+H)$^+$.

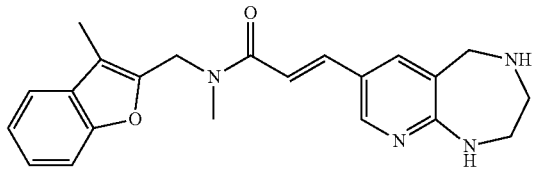

C$_{22}$H$_{25}$ClN$_4$O$_2$
Exact Mass: 412.17
Mol. Wt.: 412.91 b) (E)-N-Methyl-N-(3-methylbenzofuran-2-ylmethyl)-3-(2,3,4,5-tetrahydro-1H-pyrido[2,3-e][1,4]diazepin-7-yl)acrylamide hydrochloride A solution of (E)-N-methyl-N-(3-methylbenzofuran-2-ylmethyl)-3-(2,3,4,5-tetrahydro-1H-pyrido[2,3-e][1,4]diazepin-7-yl)acrylamdie (0.21, 0.56 mmol) in CH$_2$Cl$_2$ (5 mL) was treated with anhydrous HCl (0.56 mL of a 1.0 M solution in Et$_2$O, 0.56 mmol). After stirring for 5 min, the mixture was diluted with Et$_2$O (50 mL), allowed to stir for 30 min and sonicated for 5 min. The solid was isolated by filtration, washed with Et$_2$O, and dried under vacuum at 50° C. for 4 days to give the title compound (0.22 g, 97%) as an off-white powder and as a mixture of amide rotamers: $^1$H NMR (300 MHz, DMSO-d$_6$) δ9.66 (br s, 2H), 8.36-8.33 (m, 1H), 8.14 (s, 1H), 7.58-7.07 (m, 7H), 4.98-4.79 (m, 2H), 4.20 (s, 2H), 3.51 (s, 2H), 3.33 (s, 2H), 3.17-2.91 (m, 3H), 2.27 (s, 3H); MS (ESI) m/e 377 (M+H)$^+$.

Example 7

Preparation of (E)-3-(4-Acetyl-2,3,4,5-tetrahydro-1H-pyrido[2,3-e][1,4]diazepin-7-yl)-N-methyl-N-(3-methylbenzofuran-2-ylmethyl)acrylamide hydrochloride

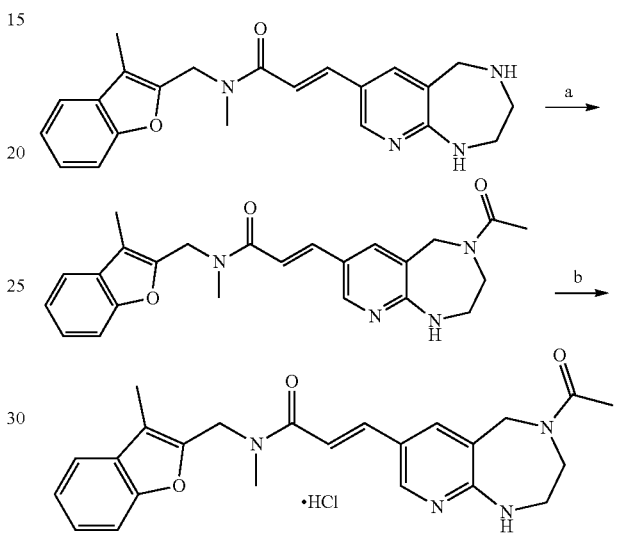

a) Ac$_2$O, Et$_3$N, CH$_2$Cl$_2$; b) HCl in Et$_2$O, CH$_2$Cl$_2$

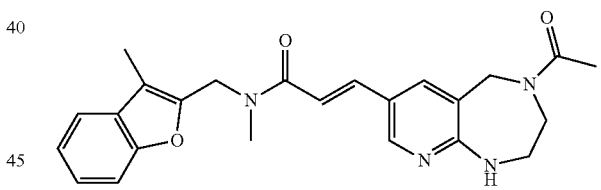

C$_{24}$H$_{26}$N$_4$O$_3$
Exact Mass: 418.20
Mol. Wt.: 418.49 a) (E)-3-(4-Acetyl-2,3,4,5-tetrahydro-1H-pyrido[2,3-e][1,4]diazepine-7-yl)-N-methyl-N-(3-methylbenzofuran-2-ylmethyl)acrylamide A solution of (E)-N-methyl-N-(3-methylbenzofuran-2-ylmethyl)-3-(2,3,4,5-tetrahydro-1H-pyrido[2,3-e][1,4]diazepin-7-yl)acrylamide (105 mg, 0.280 mmol) in CH$_2$Cl$_2$ (6 mL) was treated with Et$_3$N (0.05 mL, 0.36 mmol) followed by acetic anhydride (27 μL, 0.29 mmol). After stirring for 1.5 h, the mixture was diluted with CH$_2$Cl$_2$ (100 mL) and washed with H$_2$O (25 mL). The organic layer was dried over Na$_2$SO$_4$, filtered and concentrated to a tan residue. Purification by flash column chromatography (silica gel, CH$_2$Cl$_2$/MeOH, 96:4) gave the title compound (89 mg, 76%) as a colorless residue and as a mixture of amide rotamers: MS (ESI) m/e 419 (M+H)$^+$.

67

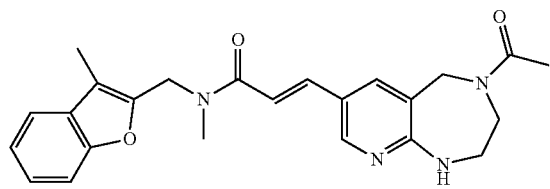

•HCl

C₂₄H₂₇ClN₄O₃
Exact Mass: 454.18
Mol. Wt.: 454.95 b) (E)-3-(4-Acetyl-2,3,4,5-tetrahydro-1H-pyrido[2,3-e][1,4]diazepin-7-yl)-N-methyl-N-(3-methylbenzofuran-2-yl-methyl)acrylamide hydrochloride A solution of (E)-3-(4-acetyl-2,3,4,5-tetrahydro-1H-pyrido[2,3-e][1,4]diazepin-7-yl)-N-methyl-N-(3-methylbenzofuran-2-ylmethyl)acrylamide (89 mg, 0.21 mmol) in CH₂Cl₂ (4 mL) was treated with anhydrous HCl (0.21 mL of a 1.0 M solution in Et₂O, 0.21 mmol). After stirring for 15 min, the mixture was diluted with Et₂O (25 mL) and allowed to stir for 2 h. The solid was isolated by filtration, washed with Et₂O and dried under vacuum at 50° C. for 3 days to give the title compound (83 mg, 88%) as a white powder and as a mixture of amide rotamers; ¹H NMR (300 MHz, DMSO-d₆) δ8.46-8.23 (m, 3H), 7.58-7.22 (m, 6H), 5.02-4.80 (m, 4H), 3.87-3.74 (m, 4H), 3.19-2.90 (m, 3H), 2.26 (s, 3H), 2.03-1.99 (m, 3H); MS (ESI) m/e 419 (M+H)⁺.

Example 8

Preparation of N-Methyl-N-(3-methyl-benzofuran-2-ylmethyl)-3-(5,7,8,9)-tetrahydro-6-oxa-1,9-diaza-benzocyclohepten-3-yl)-acrylamide

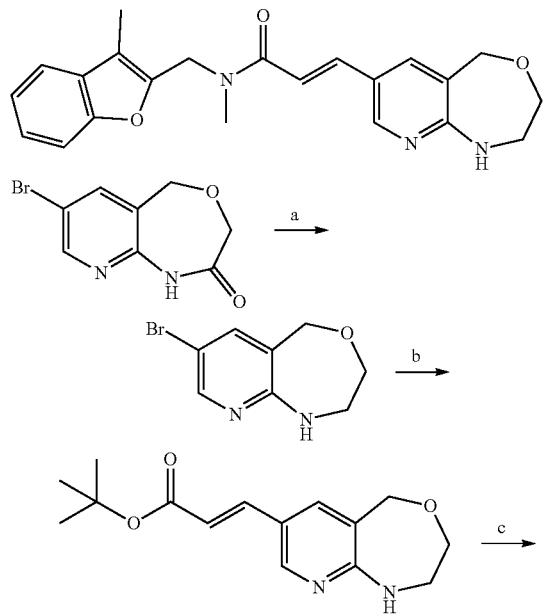

68

-continued

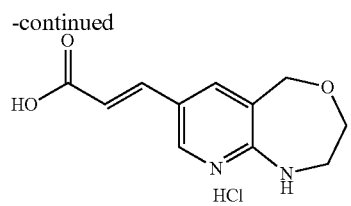

(a)) BH₃.THF complex, THF, reflux; (b) tert-butyl acrylate, Pd(OAc)₂, P(o-tol)₃, (i-Pr)₂EtN, DMF; (c) i TFA, CH₂Cl₂; ii. 4 M HCl/dioxane a) 3-Bromo-5,7,8,9-tetrahydro-6-oxa-1,9-diaza-benzocycloheptene To a solution of 3-Bromo-5,9-dihydro-6-oxa-1,9-diazabenzocyclohepten-8-one (1.0 g, 4.13 mmol) in THF (40 mL) at 0° C. was added BH₃ (30 mL of a 1.0 M solution in THF, 30.0 mmol). The solution was heated to reflux. After 18 h, the solution was cooled to 0° C. and the reaction quenched with H₂O (2.5 mL). The mixture was concentrated and the resulting off-white solid was dissolved in MeOH (30 mL) and NaOH (15 mL of a 2 N solution). The mixture was heated at reflux for 4 h. The MeOH was removed under reduced pressure. The resulting precipitate was collected by filtration and washed with H₂O (20 mL). The wJiite solid was dried to give the title compound (0.360 g, 38%). ¹H NMR (300 MHz, DMSO-d₆) δ8.06 (d, J=23 Hz, 1H), 7.71 (d, J=2.3 Hz, 1H), 6.55 (br s, 1H), 4.47 (s, 2H), 3.74-3.70 (m, 2H), 3.16-3.12 (m, 2H); ESI MS m/z 229 (100%); 231 (100%) [C₈H₉BrN₂O+ H]⁺.

b) 3-(5,7,8,9-Tetrahydro-6-oxa-1,9-diaza-benzocyclohepten-3-yl)-acrylic acide tert-butyl ester A solution of 3-Bromo-5,7,8,9-tetrahydro-6-oxa-1,9-diaza-benzocycloheptene (0.5 g, 2.2 mmol), tert-butyl acrylate (1.6 mL, 10.9 mmol) and (i-Pr)₂EtN (1.1 mL, 6.5 mmol) in proprionitrile/DMF (20 mL/5 ml) was de-oxygenated with Ar for 30 min. The mixture was treated with Pd(OAc)₂ (49 mg, 0.22 mmol) and P(o-tol)₃ (133 mg, 0.44 mmol) then heated to 100° C. for 16 h. The hot mixture was filtered through a pad of celite. The filtrate was diluted with H₂O (100 ml) then extracted with dichloromethane (1×75 mL). The combined organic fractions were treated with brine (100 mL), dried Over Na₂SO₄ and concentrated to give a yellow residue. This was subjected to flash chromatography on silica gel using 1.3% methanol:dichloromethane. The appropriate fractions were collected and concentrated, to give a cream solid. Yield: 0.4 g (67%); ¹H NMR (400 MHz, DMSO-d₆) δ8.19 (d, J=2.1 Hz, 1H), 7.87 (d, J=2.1 Hz, 1H), 7.44 (d, J=16.0 Hz, 1H), 6.87 (br s, 1H), 6.33 (d, J=16.0 Hz, 1H), 4.50 (s, 2H), 3.75-3.72 (m, 2H), 3.22-3.20 (m, 2H), 1.47 (s, 9H); ESI MS m/z 277 [C₁₅H₂₀N₂O₃+H]⁺ c) 3-(5,7,8,9-Tetrahydro-6-oxa-1,9-diaza-benzocyclohepten-3-yl)-acrylic acid hydrochloride A suspension of 3-(5,7,8,9-Tetrahydro-6-oxa-1,9-diaza-benzocyclohepten-3-yl)-acrylic acid tert-butyl ester (0.14 g, 0.49 mmol) in CH₂Cl₂ (5 mL) was treated with TFA (5 ml). After stirring at room temperature for 30 min, the clear tan solution was concentrated in vacuo. The resulting oil was triturated with hexanes (20 mL) until the oil was converted to a fine off-white solid. The solid was then suspended in anhydrous HCl in dioxane (2 mL, 4.0 M), sonicated and concentrated to about 1 mL. The suspension was treated with Et₂O (20 mL), sonicated, isolated by filtration and dried under vacuum. Yield: 0.11 g (87%); ¹H NMR (300 MHz, DMSO-d₆) δ8.40 (br s, 3H), 8.31-8.29 (m, 2H), 7.53 (d, J=16.0 Hz, 1H), 6.51 (d, J=16.0 Hz, 1H), 4.76 (s, 2H), 3.96-3.92 (m, 2H), 3.71-3.67 (m, 2H); ESI MS m/z 221 [C$_{11}$H$_{12}$N$_2$O$_3$+H]$^+$ d) N-Methyl-N-(3-methyl-benzofuran-2-ylmethyl)3-(5,7,8,9-tetrahydro-6-oxa-1,9-diaza-benzocyclohepten-3-yl)-acrylamide EDC (0.10 g, 0.52 mmol) was added to a solution of 3-(5,7,8,9-Tetrahydro-6-oxa-1,9-diaza-benzocyclohepten-3-yl-acrylic acid hydrochloride (0.11 g, 0.43 mmol), HOBt (64 mg, 0.47 mmol), Methyl-(3-methyl-benzofuran-2-ylmethyl)-amine (91 mg, 0.52 mmol) and (i-Pr)$_2$EtN (0.44 mL, 2.58 mmol) in DMF (6 mL). The mixture was allowed to stir overnight at 35° C. lire mixture was cooled to 0° C. and diluted with H$_2$O (15 mL) with rapid stirring. The resulting precipitate was filtered, washed with H$_2$O (30 mL) then dried under high vacuum. The solid was triturated with Et$_2$O (3.0 mL), stirred for 20 mm then filtered to give a beige solid as a mixture of amide rotaruers. Yield: 0.10 g (62%); $^1$H NMR (300 MHz, DMSO-d$_6$) δ8.25 (s, 1H), 7.94 (s, 1H), 7.59-7.03 (m, 6H), 6.79 (hr s, 1H), 4.98 and 4.79 (2×s, 2H), 4.53 (s, 2H), 3.77-3.73 (m, 2H), 3.25-3.19 (m, 2H), 3.17 and 2.93 (2×s, 3H), 2.28 (s, 3H); ESI MS m/z 378 [C$_{22}$H$_{23}$N$_3$O$_3$+H]$^+$ Example 9

Preparation of N-Methyl-N-(1-methyl-1H-indol-2-ylmethyl)-3-(5,7,8,9-tetrahydro-6-oxa-1,9-diaza-benzocyclohepten-3-yl)-acrylamide

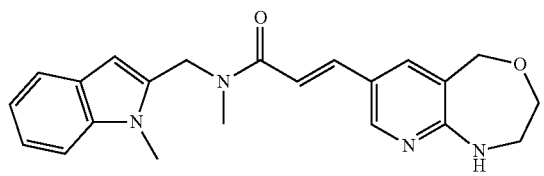 [SMILES: CN(Cc1cc2ccccc2n1C)C(=O)/C=C/c1cnc2c(c1)COCCN2]

EDC (0.10 g, 0.52 mmol) was added to a solution of 3-(5,7,8,9-Tetrahydro-6-oxa-1,9-diaza-benzocloheptren-3-yl)-acrylic hydrochloride (0.11 g, 0.43 mmol), HOBt (64 mg, 0.47 mmol), Methyl-(1-methyl-1H-indol-2-ylmethyl)-amine (128 mg, 0.47 mmol) and (i-Pr)$_2$EtN (0.36 mL, 2.15 mmol) in DMF (6 mL). The mixture was allowed to stir overnight at 35° C. The mixture was cooled to 0° C. and diluted with H$_2$O (15 mL) with rapid stirring. The resulting gummy precipitate was filtered, washed with H$_2$O (30 mL) then with Et$_2$O (20 mL). The solid was dissolved in dichloromethane (100 mL), washed with H$_2$O (50 mL), brine (50 mL), dried over MgSO$_2$, and treated with charcoal. The mixture was filtered and the filtrate was passed through a plug of silica gel. The silica gel was washed with ethyl acetate (50 mL) then with 5% methanol: dichloromethane (50 mL). The combined organic fractions were concentrated to give an oil. The resulting oil was triturated with ether:hexanes (20 mL) until the oil was converted to a beige solid. Yield: 40 mg (25%) as a mixture of amide rotamers; $^1$H NMR (400 MHz, DMSO-d$_6$) δ8.24 (br s, 1H), 7.92 and 7.85 (2×s, 1H), 7.50-7.39 (m, 3H), 7.18-6.92 (m, 3H), 6.78 (br s, 1H), 6.41 and 6.20 (2×s, 1H), 5.07 and 4.83 (2×s, 2H), 4.52 and 4.45 (2×s, 2H), 3.71-3.61 (m, 5H), 3.50-3.40 (m, 2H), 3.10 and 2.95 (2×s, 3H); ESI MS m/z 377 [C$_{22}$H$_{24}$N$_4$O$_2$+H]$^+$ Example 9

Preparation of N-Methyl-N-(3-methyl-benzofuran-2-methyl)-3-(6,7,8,9-tetrahydro-5oxa-1,9-diaza-benzocyclohepten-3-yl)-acrylamid hydrochloride

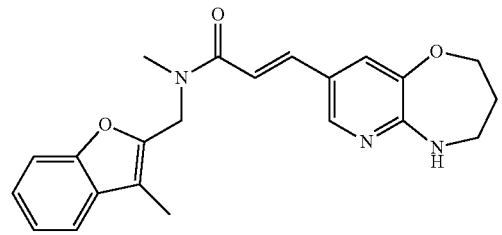 [SMILES: Cc1c(CN(C)C(=O)/C=C/c2cnc3c(c2)OCCCN3)oc2ccccc12]

a) Preparation of 3-(2-bromo-pyridin-3-yloxy)-propylamine

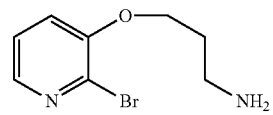 [SMILES: NCCCOc1cccnc1Br]

Diisopropyl azodicarboxylate (4.65 mL, 24 mmol) was added slowly to a dioxane (200 mL) solution of 2-bromo-pyridin-3-ol (3.50 g, 20 mmol), 3-aminopropanol (1.67 mL, 22 mmol) and triphenylphosphine (6.30 g, 24 mmol) at 10° C. After stirring the mixture for 30 mm at this temperature, it was refluxed for 18 h Upon cooling, the volatiles were evaporated and the residue was purified fey chromatography (silica, 3% MeOH in CH$_2$Cl$_2$ then 5% (2M NH$_3$, m MeOH) in CH$_2$Cl$_2$ to afford the title compound (3.19 g, 69%). $^1$H NMR (300 MHz, CDCl$_3$, δ): 7.98 (dd, J=4.5, 1.8 Hz, 1H), 7.23 (dd, J=4.5, 8.2 Hz, 1H), 7.15 (dd, J=1.8, 8.2 Hz, 1H), 4.15 (t, J=6.0 Hz, 2H), 2.98 (t, J=6.6 Hz, 2H), 2.00 (m, 2H). MS (ESI); m/e 231 and 233(M+H)$^+$.

b) Preparation of 6,7,8,9-tetrahydro-5-oxa-1,9-diaza-benzcycloheptene

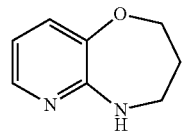 [SMILES: c1cnc2c(c1)OCCCN2]

Potssium tert-butoxide (18 nL, 18 mmol) was added to a THF (120 mL) solution of 3-(2-bromo-pyridin-3-yloxy)-propylamine (2.75 g, 11.9 mmol). The solution was purged with an Ar stream for 10 min, bis(dibenzylideneacetone)palladium (342 mg, 0.6 mmol) and tri-tert-butylphosphine (2.1 mL, 0.7 mmol, 10% in hexane) were added and the mixture was stirred at 60° C. for 5 h. The solvent was evaporated, the residue was dissolved in CH$_2$Cl$_2$. This solution was washed with water, dried and evaporated. Chromatographic purification (silica, 0-2% MeOH in CH$_2$Cl$_2$) afforded 0.75 g (42%) of the title compound. $^1$H NMR (300 MHz, DMSO-d$_6$, δ): 7.70

(dd, J=4.8, 1.4 Hz, 1H), 7.09 (dd, J=7.7, 1.4 Hz, 1H), 6.60 (dd, J=4.8, 7.7 Hz, 1H), 6.02 (s, br, 1H), 4.06 (t, J=5.5 Hz, 2H), 3.21 (m, 2H), 1.90 (m, 2H).

c) Preparation of 3-bromo-6,7,8,9-tetrahydro-5-oxa-1,9-diaza-benzocycloheptene

A solution of bromine (960 mg, 6 mmol) in CH$_2$Cl$_2$ (50 mL) was added drop wise at 0° C. to a CH$_2$Cl$_2$ (30 mL) suspension of 6,7,8,9-tetrahydro-5-oxa-1,9-diaza-benzocycloheptene (750 mg, 5 mmol) and solid K$_2$CO$_3$ (1 g). The mixture was stirred for 30 min at 20° C., then the excess bromine was quenched with a saturated solution of aqueous NaHSO$_3$. The basic aqueous phase was separated, extracted with CH$_2$Cl$_2$, the combined organic layers were dried and evaporated to afford the title-compound (1.10 g, 96%). $^1$H NMR (300 Hz, DMSO-d$_6$, δ): 7.78 (d, J=1.8 Hz, 1H), 7.30 (d, J=1.9 Hz, 1H), 6.35 (s, br, 1H), 4.10 (t, J=5.7 Hz, 2H), 3.24 (m, 2H), 1.92 (m, 2H), MS (ESI): m/e 229 and 231 (M+H)$^+$.

d) Preparation of (6,7,8,9-tetrahydro-5-oxa-1,9-diaza-benzocyclohepten-3-yl)-acrylic acid ethyl ester

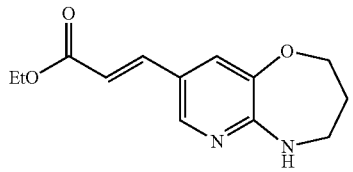 [SMILES: CCOC(=O)/C=C/c1cnc2c(c1)OCCCN2]

A solution of 3-bromo-6,7,8,9-tetrahydro-5-oxa-1,9-diaza-benzocycloheptene (1.1 g, 4.80 mmol), ethyl acrylate (1.5 mL, 14.4 mmol) and diisopropylethylamine (2.5 mL, 14.4 mmol) in propionitrile (100 mL) was purged with an Argon stream for 10 min. Pd(OAc)$_2$ (108 mg, 048 mmol) and P(o-tol)$_3$ (292 g, 0.96 mmol) were added and the Argon purge was repeated. The mixture was stirred at 100° C. for 8 h under Argon. Upon cooling, the resultant mixture was filtered through celite; the filtrate was evaporated. The crude product was purified by chromatography (silica, 0-2% MeOH CH$_2$Cl$_2$) to afford the title compound (0.753 g, 63%). $^1$H NMR (300 MHz, DMSO-d$_6$, δ): 7.98 (d, J=1.9 Hz, 1H), 7.52 (d, J=1.9 Hz, 1H), 7.51 (d, J=16 Hz, 1H), 6.83 (s, br, 1H), 6.42 (d, J=16 Hz, 1H), 4.15 (m, 4H), 3.34 (m, 2H), 1.98 (m, 2H), 1.25 (t, J=2 Hz, 3H).

e) Preparation of 3-(6,7,8,9-tetrahydro-5-oxa-1,9-diaza-benzocyclohepten-3-yl)-acrylic acid

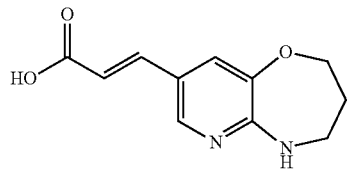 [SMILES: O=C(O)/C=C/c1cnc2c(c1)OCCCN2]

A solution of (6,7,8,9-tetrahydro-5-oxa-1,9-diaza-benzocyclohepten-3-yl)-acrylic acid ethyl ester (0.75 g, 3 mmol) in MeOH (30 mL) and aqueous NaOH (2 mL, 8 mmol, 4N) was refluxed for 23 hours. Upon cooling and addition of water (10 mL), the volatiles were evaporated: the aqueous solution was washed with CH$_2$Cl$_2$ and neutralized (1N HCl). The precipitate was filtered and dried to afford title product (55 mg, 8%). An additional 46 mg (7%) was obtained by extracting the aqueous filtrate with EtOAc. $^1$H NMR (300 MHz, DMSO-d$_6$, δ): 12.10 (s, br 1H), 7.93 (d, J=1.9 Hz, 1H), 7.46 (d, J=1.9 Hz, 1H), 7.43 (d, J=16 Hz, 1H), 6.75 (t br, J=3.4 Hz, 1H), 6.29 (d, J=16 Hz, 1H), 4.13 (t, J=1H), 3.35 (m, 2H), 1.96 (m, 2H).

f) Preparation of N-Methyl-N-(3-methyl-benzofuran-2-yl-methyl)-3-(6,7,8,9-tetrahydro-5-oxa-1,9-diaza-benzocylohepten-3-yl)-acrylamid hydrochloride EDC (108 mg, 0.56 mmol) was added to a solution of 3-(6,7,8,9-tetrahydro-5-oxa-1,9-diaza-benzocyclohepten-3-yl)-acryic acid (95 mg, 0.43 mmol), methyl-(3-methyl-benzofuran-2-ylmethyl)-amine (100 μL, 0.52 mmol), HOBt.H$_2$O (64 mg, 0.47 mmol) and DIPEA (225 μL, 1.29 mmol) in dry DMF (4 mL). After stirring for 23 hr, the mixture was cooled (10° C.) and treated with water (50 mL). The precipitated crude product was separated by decantation and purified by chromatography (silica, EtOAc). The clean fractions of the free base were collected, concentrated to 10 mL and treated with HCl (0.7 mL, 1.4 mmol, 2M in Et$_2$O). The resulting precipitate was collected by filtration, washed with EtOAc and hexanes to afford the title compound (123 mg, 57%). $^1$H NMR (300 MHz, DMSO-d$_6$, δ): 8.07 (m, 2H), 7.58-7.41 (m, 3H), 7.36-7.15 (m, 3H), 4.99 and 4.77 (rotamers, 2s, 2H), 4.28 (m, 2H), 3.57 (m, 2H), 3.16 and 2.90 (rotamers, 2s, 3H), 2.25 (s, 3H), 2.11 (m, 2H). MS (ESI); m/e 378 (M+H)$^+$.

Example 10

Preparation of N-Methyl-N-(3-methyl-benzofuran-2-ylmethyl)-3-(4-methyl-2,3,4,5-tetrahydro-1H-pyrido[2,3-e][1,4]diazepin-7-yl)-acrylamide dihydrochloride a) 7-Bromo-4-methyl-2,3,4,5-tetrahydro-1H-pyrido[2,3-e][1,4]diazepine hydrobromide

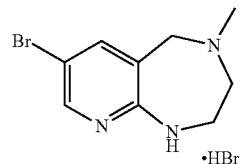

7-bromo-4-methyl-1,3,4,5-tetrahydro-pyrido[e][1,4]diazepin-2-one (1.67 g, 6.55 mmol) was reduced to give a 1:1 mixture of the title compound and 4-methyl-2,3,4,5-tetrahydro-1H-benzo[e][1,4]diazepine. The mixture was dissolved in acetic acid (12 mL), treated with bromine (1.04 g, 6.5 mmol) and stirred at room temperature overnight. Ether (100 mL) was added and the precipitate was isolated by filtration to yield the title compound as an orange solid (2.04 g, 95%). $^1$H NMR (300 MHz, DMSO-d$_6$) δ10.23 (s, 1H) 8.16 (d, J=2.3 Hz, 1H), 7.84 (d, J=2.0 Hz, 1H), 6.89 (s, 1H), 4.25-4.48 (m, 2H), 3.54-3.58 (m, 2H), 3.28-3.35 (m, 2H), 2.86-2.87 (m, 3H); MS (ESI) m/e 242 (C$_9$H$_{12}$BrN$_3$+H)$^+$.

b) 3-(4-Methyl-2,3,4,5-tetrahydro-1H-pyrido[2,3-e][1,4]diazepin-7-yl)-acrylic acid tert-butyl ester

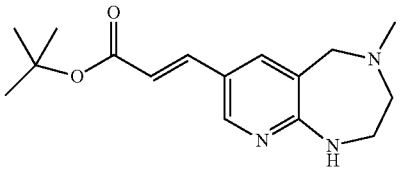 [SMILES: CN1CCNc2ncc(/C=C/C(=O)OC(C)(C)C)cc2C1]

7-bromo-4-methyl-2,3,4,5-tetrahydro-1H-pyrido[2,3-e][1,4]diazepine hydrobromide (2.0 g, 6.2 mmol) was subjected to Heck coupling with tert-butyl acrylate to give crude product. Purification by silica gel chromatography (CH$_2$Cl$_2$:MeOH:NH$_4$OH/95:4.95:0.05) gave the title compound as a brown oil (970 mg, 55%), $^1$H NMR (300 MHz, CDCl$_3$) 8.11 (d, J=2.1 Hz, 1H), 7.52 (d, J=2.2 Mz, 1H), 7.47 (d, J=16.0 Hz, 1H) 6.22 (d, J=16.0 Hz, 1H), 3.64 (s, 2H), 3.27-3.31 (m, 2H), 2.83-2.88 (m, 2H), 2.44 (s, 3H), 1.52 (s, 9H); MS (ESI) m/e 290 (C$_{16}$H$_{23}$N$_3$O$_2$+H)$^+$.

c) 3-(4-Methyl-2,3,4,5-tetrahydro-1H-pyrido[2,3-e][1,4]diazepin-7-yl)-acrylic acid hydrochloride

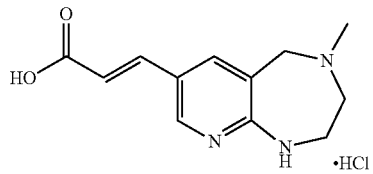 [SMILES: CN1CCNc2ncc(/C=C/C(=O)O)cc2C1 ; Cl]

3-(4-methyl-2,3,4,5-tetrahydro-1H-pyrido[2,3-e][1,4]diazepin-7-y)-acrylic acid tert-butyl ester (576 mg, 2.1 mmol) was converted to the title compound which was obtained as a yellow solid (542 mg, 96%). $^1$H NMR (300 MHz, DMSO-d$_6$) 8.35 (s, 1H), 8.17-8.22 (m, 1H), 7.51 (d, J=16.1 Hz, 1H), 6.40 (d, J=16.1, Hz, 1H), 4.25-4.48 (m, 2H), 3.60-3.75 (m, 2H), 3.30-3.45 (m, 2H), 2.68 (s, 3H).

d) N-Methyl-N-(3-methyl-benzofuran-2-ylmethyl)-3-(4-methyl-2,3,4,5-tetrahydro-1H-pyrido[2,3-e][1,4]diazepin-7-yl)-acrylamide hydrochloride

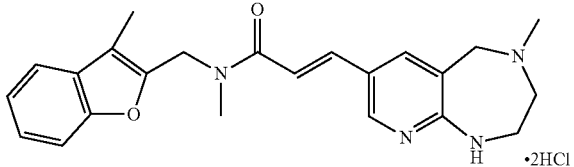 [SMILES: Cc1c(CN(C)C(=O)/C=C/c2cnc3c(c2)CN(C)CCN3)oc2ccccc12 ; "·2HCl"]

EDC (0.21 g, 1.1 mmol) was added to a suspension of methyl-(2-methyl-benzofuran-3-ylmethyl)-amine (158 mg, 0.9 mmol) and 3-(4-Methyl-2,3,4,5-tetrahrydo-1H-pyrido[2,3-e][1,4]diazepin-7-yl)-acrylic acid hydrochloride (201 mg, 0.75 mmol). The mixture was allowed to stir overnight at 40° C. The mixture was cooled to 0° C. and diluted with H2O (60 mL) with rapid stirring. The resulting precipitate was filtered, washed with H$_2$O (20 ml) then dried under high vacuum. The solid was then subjected to flash chromatography on silicia gel using 5% methonal:dichloromethane. The fractions were collected and treated with 5 mL of 2.0M HCL in Et$_2$O. The suspension was concentrated, triturated with Et$_2$O (50 Ml then filtered to give a coupled solid. The resulting solid was dissolved in methylene chloride (5 ml) and treated with 2M HCl in ether (0.75 mL, 1.5 mmol). The resultant yellow precipitate was filtered, triturated with diethyl ether and dried under high vacuum to afford the title compound as a white solid (186 mg, 53%) and a mixture of amide rotomers. $^1$H NMR (300 MHz, DMSO-d$_6$) 11.80 (bs, 1H) 8.45-8.17 (m, 2H), 7.56-7.46 (m, 3H), 7.29-7.14 (m, 3H), 4.82-4.97 (m, 2H), 4.60-4.70 (m, 1H), 4.30-4.40 (m, 1H), 3.65-3.75 (m, 3H), 3.33-3.45 (m, 1H), 2.89-2.78 (m, 2H) 2.82 (s, 3H), 2.25 (s, 3H); MS (ESI) m/e 391 (C$_{23}$H$_{26}$N$_4$O$_2$+H)$^+$.

Example 11

N-Methyl-N-(1-methyl-1H-indol-2-ylmethyl)-3-(4-methyl-2,3,4,5-tetrahydro-1H-pyrido[2,3-e][1,4]diazepin-7-yl)-acrylamide dihydrochloride

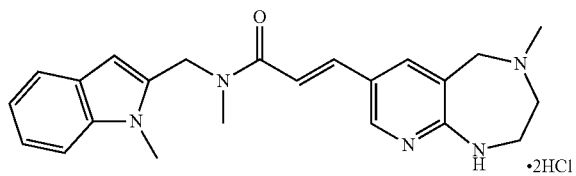 [SMILES: CN1CCNc2ncc(/C=C/C(=O)N(C)Cc3cc4ccccc4n3C)cc2C1 ; "·2HCl"]

EDC (0.21 g, 1.1 mmol) was added to a suspension of methyl-(2-methyl-benzofuran-3-ylmethyl)-amine (158 mg, 0.9 mmol) and 3-(4-Methyl-2,3,4,5-tetrahydro-1H-pyrido[2,3-e][1,4]diazepin-7-yl)acrylic acid hydrochloride (201 mg, 0.75 mmol). The mixture was allowed to stir overnight at 40° C. The mixture was cooled to 0° C. and diluted with H$_2$O (60 mL) with rapid stirring. The resulting precipitate was filtered, washed with H$_2$O (20 mL) then dried under high vacuum. The solid was then subjected to flash chromatography on sillcia gel using 5% methonal:dichloromethane. The fractions were collected and treated with 5 mL of 2.0M HCL in Et$_2$O. The suspension was concentrated, triturated with Et$_2$O (50 Ml then filtered to give a coupled solid, were coupled. The resulting solid was dissolved in methylene chloride (5 ml) and treated with 2M HCl in ether (0.75 mL, 1.5 mmol). The yellow precipitate was filtered, triturated with diethyl ether and dried under high vacuum to afford the title compound as a white solid (138 mg, 42%). $^1$H NMR (300 MHz, DMSO-d$_6$) 11.92 (bs, 1H) 8.43-8.17 (m, 2H), 7.53-7.38 (m, 3H), 7.29-6.98 (m, 3H), 6.40 (s, 1H), 5.05-4.84 (m, 2H), 4.55-4.63 (m, 1H), 4.31-4.38 (1H), 3.64-3.80 (m, 6H), 3.33-3.45 (m, 1H), 2.97-2.93 (m,2H) 2.82-2.79 (m, 3H); MS (ESI) m/e 390 (C$_{23}$H$_{27}$N$_5$O+H)$^+$.

Example 12

Preparation of (E)-N-methyl-N-(3-methylbenzofuran-2-yl)methyl)-3-(6,7,8,9-tetrahydro-5H-pyrido[2,3-b]azepin-3-yl)acrylamide hydrochloride

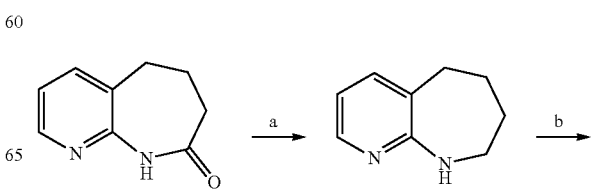

-continued

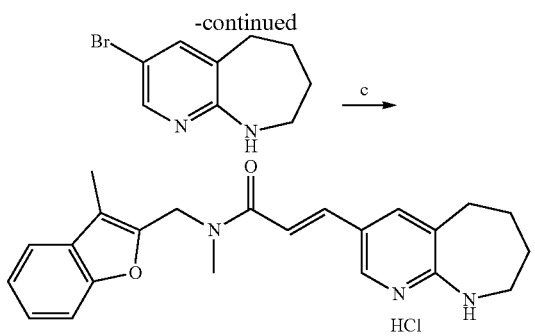

(a) LiAlH₄, THF; (b) Br₂, Acetic Acid; (c) N-methyl-N-((3-methylbenzofuran-2-yl)methylacrylamide, DIPEA, Pd(OAc)₂, P(OCa)₂, P(o-tol)₃, DMF.
(6,7,8,9)-tetrahydro-5H-pyrido[2,3-b]azepine)

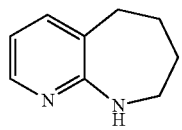 [SMILES: c1cnc2c(c1)CCCCN2]

Prepared according to the standard procedure. The title compound (6,7,8,9-tetrahydro-5H-pyrido[2,3-b]azeplne) (400 mg, 87%) was obtained as a brown oil: $^1$H NMR (400 MHz, DMSO-d₆) δ7.85 (s, 1H), 7.34-7.33 (m, 1H), 6.63-6.62 (m, 1H), 5.75 (s, 1H), 3.04 (bs, 2H), 2.62 (bs, 2H), 1.69-1.64 (m, 4H).
(3-bromo-6,7,8,9-tetrahydro-5H-pyrido[2,3-b]azepine

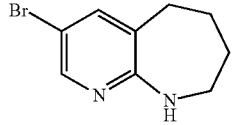

Prepared according to a standard procedure. The title compound (3-bromo-6,7,8,9-tetrahydro-5H-pyrido[2,3-b]azepine) (493 mg, 80%) was obtained as a brown oil: $^1$H mm (400 MHz, DMSO-d₆) δ7.91 (s, 1H), 7.55 (s, 1H), 3.07-3.06 (m, 2H), 2.65-2.64 (m, 2H), 1.71-1.64 (m, 4H).
E)-N-methyl-N-((3-methylbenzofuran-2-yl)methyl)-3-(6,7,8,9-tetrahydro-5H-pyrido[2,3-b]azepin-3-yl)acrylamide hydrochloride

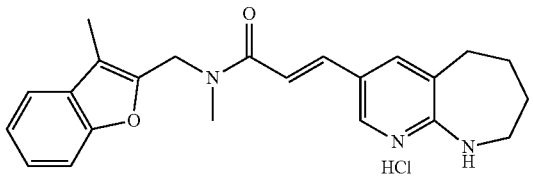 [SMILES: Cc1c(CN(C)C(=O)/C=C/c2cnc3c(c2)CCCCN3)oc2ccccc12 ; Cl]

A solution of 3-bromo-6,7,8,9-tetrahydro-5H-pyrido[2,3-b]azepine (150 mg, 0.661 mmol), N-methyl-N-((3-methylbenzofuran-2-yl)methylacrylamide (227 mg, 0.991 mmol) and DIPEA (0.98 mL, 5.63 mmol) in anhydrous DME (4.0 mL) was prepared. Argon was bubbled into the mixture with stirring for 30 min. Next P(o-tol)₃ (40.2 mg, 0.132 mmol) and Pd(OAc)₂ (14.8 mg, 0.0661 mmol) were added to the mixture and argon was bubbled into the reaction for an additional 5 min. The reaction was sealed and treated under microwave irradiation for 5 min at 160° C. The reaction was cooled to room temperature and diluted, with water (20 mL) and the aqueous layer was extracted with CH₂Cl₂ (4×10 mL). The combined organic layers were washed with brine (20 mL), dried over Na₂SO₄, filtered and concentrated to give a brown oil. Purification by preparative HPLC (water/acetonitrile/ 0.05% TFA mixture) gave the desired product as a white solid which was dissolved in CH₂Cl₂ (5.0 mL). To the mixture was added HCl (540 µl of 1M solution in ether, 0.540 mmol) and the mixture was stirred for 5 min at room temperature. After concentrating under high vacuum, the title compound ((E)-N-methyl-N-((3-methylbenzofuran-2-yl)methyl)-3-(6,7,8,9-tetrahydro-5H-pyrido[2,3-b]azepin-3-yl)acrylamide hydrochloride) (200 mg, 80%) was obtained as a yellow solid and a mixture of amide rotomers: $^1$H NMR (400 MHz, DMSO-d₆) δ8.29-8.26 (m, 2H), 8.20-8.18 (m, 1H), 7.57-7.55 (m, 1H), 7.49-7.43 (m, 2H), 7.30-7.17 (m, 3H), 4.99-4.78 (m, 2H), 3.58 (bs, 2H), 3.17-2.90 (m, 5H), 2.26 (s, 3H), 1.92 (bs, 4H); ESI MS m/z 376 [C₂₃H₂₅N₃O₂+H]⁺.

Example 13

Preparation of (E)-N-methyl-N-((3-methylbenzol[b]thiophen-2-yl)methyl)-3-(6,7,8,9-tetrahydro-5H-pyrido[2,3-b]azepin-3-yl)acrylamide hydrochloride

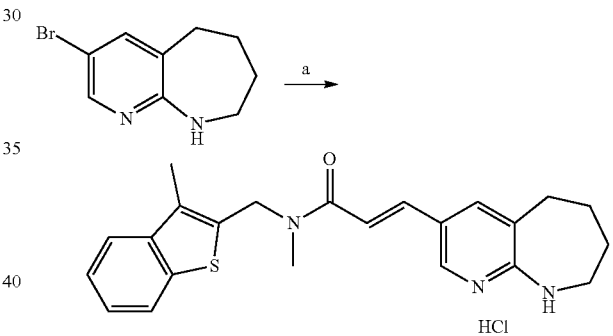

(a) N-methyl-N-((3-methylbenzo[b]thiophen-2-yl)methyl)acrylamide, DIPEA, Pd(OAc)₂, P(o-tol)₃, DMF.

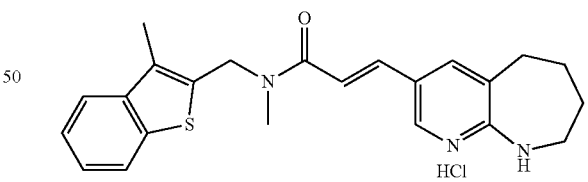

Prepared according to a standard procedure. After purification by preparative HPLC (water/acetonitrile/0.05% TFA mixture) the desired product was dissolved in CH₂Cl₂ (2.0 mL). To the mixture was added HCl (172 µl of 1M solution in ether, 0.172 mmol) and the mixture was stirred for 5 min at room temperature. After concentrating under high vacuum the title compound ((E)-N-methyl-N-((3-methylbenzo[b]thiophen-2-yl)methyl)-3-(6,7,8,9-tetrahydro-5H-pyrido[2,3-b]azepin-3-yl)acrylamide hydrochloride) (70.0 mg, 60%) was obtained as a brown solid and a mixture of amide rotomers: $^1$H NMR (400 MHze, DMSO-d₆) δ8.27-8.19 (m, 3H), 7.87-7.72 (m, 2H), 7.50-7.18 (m, 4H), 5.11-4.88 (m, 2H), 3.58 (bs, 2H), 3.14-2.91 (m, 5H), 2.41 (s, 3H), 1.91 (bs, 4H); ESI MS m/z 392 $[C_{23}H_{25}N_3OS+H]^+$.

Example 14

Preparation of (E)-tert-butyl 7-(3-(((1,2-dihydroacenaphthylen-5-yl)methyl(methyl)amino)-3-oxoprop-1-enyl)-2,3-dihydro-1H-pyrido[2,3-e][1,4]diazepine-4(5H)-carboxylate

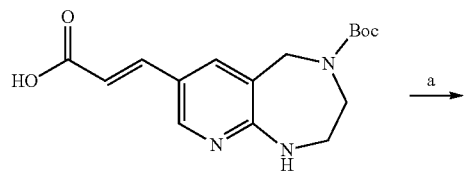

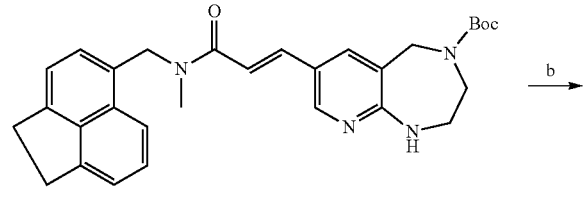

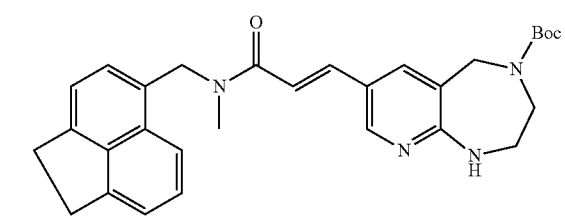 [SMILES: CN(Cc1ccc2c3c(cccc13)CC2)C(=O)/C=C/c1cnc2c(c1)CN(C(=O)OC(C)(C)C)CCN2]

(a) 1,2-dihydroacenaphthylen-5-yl)-N-methylmethanamine, EDC, HOBt, DIPEA, DMF (b) i) TFA, CH$_2$Cl$_2$ ii) HCl, ether (E)-tert-butyl 7-(3-(((1,2-dihydrocenaphthylen-5-yl)methyl)(methyl)amino)-3-oxoprop-1-enyl)-2,3-dihydro-1H-pyrido[2,3-e][1,4]diazepine-4(5H)-carboxylate Prepared according to a standard procedure. The compound was purified by silica gel chromatography (4% MeOH in CH$_2$Cl$_2$) to give a white solid (142 mg, 92%). ESI MS m/z 499 $[C_{30}H_{34}N_4O_3+H]^+$.

(E)-tert-butyl-(3-(((1,2-dihydroacenaphthylen-5-yl)methyl)(methyl)amino)-3-oxoprop-1-enyl)-2,3-dihydro-1H-pyrido[2,3-e][1,4]diazepine-4(5H)-carboxylate

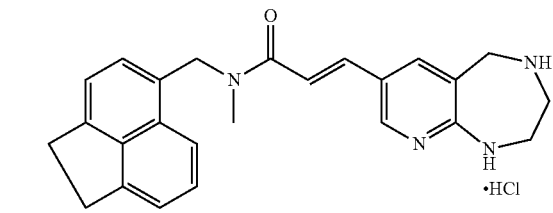 [SMILES: CN(Cc1ccc2c3c(cccc13)CC2)C(=O)/C=C/c1cnc2c(c1)CNCCN2 ; Cl]

To a solution of (E)-tert-butyl 7-(3-(((1,2-dihydroacenaphythylen-5-yl)methyl)(methyl)amino)-3-oxoprop-1-enyl)-2,3-dihydro-1H-pyrido[2,3-e][1,4]diazepine-4(5H)-carboxylate (142 mg, 0.28 mmol) in CH$_2$Cl$_2$ (4 mL) was added TFA (1 mL). The mixture was stirred at room temperature for 1 h. The solvents were removed in vacuo and dissolved in to CH$_2$Cl$_2$ (100 mL) and washed with sat. Na$_2$CO$_3$ (2 mL) dried over MgSO$_4$ and concentrated. The residue was dissolved in CH$_2$Cl$_2$ (2 mL) and HCl in ether (0.28 mL of a 1M solution) was added. The solvents were removed in vacuo and the residue was dissolved into H$_2$O (10 ml) and lyophilized to give the title compound as a yellow solid (84 mg, 60%): $^1$H NMR (300 MHz, DMSO-d$_6$) δ9.79-9.65 (m, 1H), 8.39-8.26 (m, 1H), 8.25-8.05 (m, 1H), 7.87-7.67 (m, 1H), 7.87-7.05 (m, 7H), 5.21-5.00 (2s, rotomers, 2H), 4.38-4.21 (m, 2H), 3.68-3.51 (m, 2H), 3.44-3.23 (m, 7H), 3.01-2.92 (2s, rotomers, 3H); ESI MS m/z 399 $[C_{25}H_{26}N_4O+H]^+$.

Example 15

(S,E)-3-(3-benzyl-2,3,4,5-tetrahydro-1H-pyrido[2,3-e][1,4]diazepin-7-yl)-N-methyl-N-((3-methylbenzofuran-2-yl)methyl)acrylamide trifluoroacetate

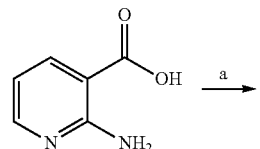

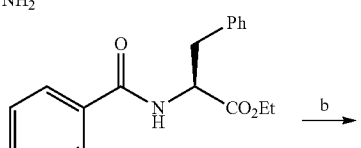

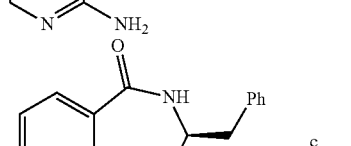

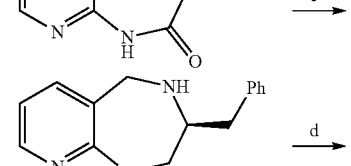

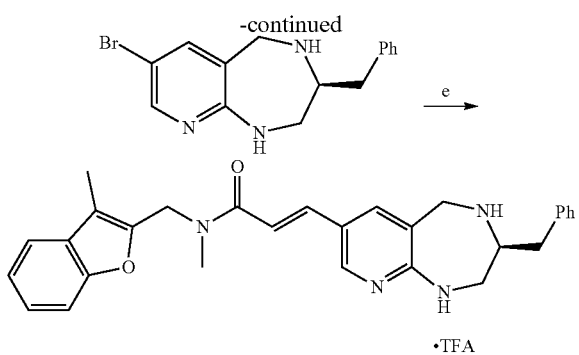

a) L-phenylalanine ethyl ester, EDC, HOBt, TEA, DMF b) NaH, THF, e) LAH, dioxane, THP, d) Br$_2$, acetic acid e) N-methyl-N-((3-methylbenzofuran-2-yl)methyl)acrylamide, DIPEA, Pd(OAc)$_2$, P(o-tol)$_3$, DMF, propionitrile.

(S)-ethyl 2-(2-aminonicotinamido)-3-phenylpropanoate

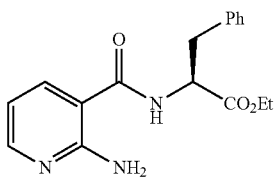 [SMILES: CCOC(=O)[C@H](Cc1ccccc1)NC(=O)c1cccnc1N]

To a solution of aminonicotinic acid (2.74 g, 20 mmol) in anhydrous DMF (100 mL) was added EDC (4.2 g, 22 mmol), HOBt (2.97 g, 22 mmol) and triethylamine (8.2 mL, 60 mmol). L-phenylalanine ethyl ester (4.97 g, 22 mmol) was added and the reaction was stirred overnight. Water (100 mL) was added and the mixture was extracted with methylene chloride (4×100 mL), dried over MgSO$_4$ and concentrate. The compound was purified by silica gel chromatography (gradient CH$_2$Cl$_2$ to 10% MeOH/CH$_2$Cl$_2$) to afford the title compound as a yellow oil (6.2 g, 98%): $^1$H NMR (300 MHz, CDCl$_3$) δ 8.78 (d, J=7.6 Hz, 1H), 8.09 (d, J=5.0 Hz, 1H), 7.89 (d, J=7.9 Hz, 1H), 7.31-7.18 (m, 5H), 6.96 (s, 2H), 6.60 (dd, J=7.7 Hz, 4.7 Hz, 1H), 4.63-4.56 (m, 1H), 4.10 (q, J=7.0 Hz, 2H), 3.15-3.09 (m, 2H), 1.05 (t, J=7.0 Hz, 3H); ESI MS m/z 314 [C$_{17}$H$_{19}$N$_3$O$_3$+H]$^+$ (S)-3-benzyl-3,4-dihydro-1H-pyrido[2,3-e][1,4]diazepine-2,5-dione

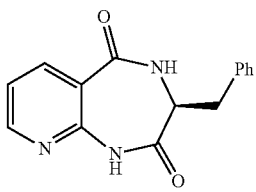 [SMILES: O=C1N[C@@H](Cc2ccccc2)C(=O)Nc2ncccc21]

(S)-Ethyl 2-(2-ammonicotinamido)-3-phenypropanoate (5.7 g, 18.1 mmol) was dissolved into THF (125 mL) under argon. Sodium hydride (1.07 g, 60% dispersion in oil 26.8 mmol) was added and the reaction was stirred overnight. Water (5 mL) was carefully added and the resulting white precipitate was collected. The precipitate was dissolved into ethyl acetate (200 mL), washed with water (50 mL) and brine (50 mL), dried over MgSO$_4$ and concentrated to a yellow solid (2.1 g, 44%); ESI MS m/z 268 [C$_{15}$H$_{13}$N$_3$O$_2$+H]$^+$.

(S)-3-benzyl-2,3,4,5-tetrahydro-1H-pyrido[2,3-e][1,4]diazepine

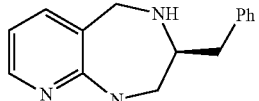

(S)-3-Benzyl-3,4-dihydro-1H-pyrido[2,3-e][1,4]diazepine-2,5-dione (1.6 g, 6 mmol) was dissolved into anhydrous THF (80 mL) under argon. Lithium aluminum hydride (30 mL of 1M in THF) was added and the reaction was heated to reflux for 16 h. The mixture was cooled to room temperature. Water (0.25 mL), 4 M NaOH (0.25 mL) and water (0.75 mL) were carefully added sequentially. The resulting sludge was filtered through celite and the filter cake was washed with ethyl acetate. The filtrate was concentrated to give the monoreduced product (880 mg), which was dissolved into dioxane (50 mL) under argon. Lithium aluminum hydride (17.3 mL of a 1 M solution in THF) was added and the reaction was heated to 95° C. for 36 h. The reaction was cooled to room temperature and carefully quenched with water (0.14 mL), 4N NaOH (0.14 mL) and water (0.42 mL) and filtered through celite. The residue was preabsorbed onto silica gel and eluted with 95:5 CH$_2$Cl$_2$/(1% NH$_4$OH in MeOH) to give the title compound as a yellow solid (60 mg, 7%); ESI MS m/z 240 [C$_{15}$H$_{17}$N$_3$+H]$^+$.

(S)-3-benzyl-7-bromo-2,3,4,5-tetrahydro-1H-pyrido[2,3-e][1,4]diazepine

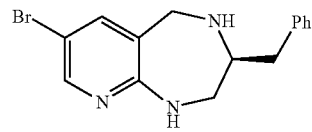 [SMILES: Brc1cnc2c(c1)CN[C@@H](Cc1ccccc1)CN2]

(S)-3-Benzyl-2,3,4,5-trahydro-1H-pyrido[2,3-e][1,4]diazepine (60 mg, 0.25 mmol) was dissolved into acetic acid (1 mL). Bromine (15 µL, 0.3 mmol) was added and the reaction was stirred overnight. Methylene chloride (10 mL) was added and the solution was washed with 1 N NaOH (1 mL) and brine (1 mL), dried over MgSO$_4$ and concentrated. The residue was dissolved in CH$_2$Cl$_2$ (3 mL) and precipitated with diethyl ether. The title compound was collected as an orange solid (80 mg, 100%): $^1$H NMR (300 MHz, CDCl$_3$) δ 7.96 (s, 1H), 7.42 (s, 1H), 7.37-7.17 (m, 5H), 5.42-5.00 (bs, 2H), 3.96-3.75 (m, 2H), 3.45-3.40 (m, 1H), 3.30-3.20 (m, 1H), 2.98-2.91 (m, 1H), 2.87-2.73 (m, 2H).

(S,E)-3-(3-benzyl-2,3,4,5-tetrahydro-1H-pyrido[2,3-e][1,4]diazepin-7-yl)-N-methyl-N-((3-methylbenzofuran-2-yl)methyl)acrylamide trifluoroacetate

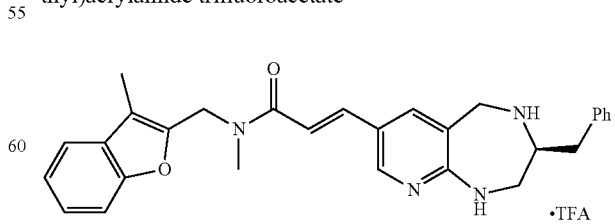

The title compound was prepared according to the standard method and isolated by preparatory HPLC as the trifluoroaceiate salt (25 mg, 15%): $^1$H NMR (400 MHz, CD$_3$OD)

δ10.35 (s, 1H), 9.95 (s, 1H), 9.15 (s, 1H), 8.86 (s, 1H), 8.40-8.07 (m, 11H), 7.88 (s, 1H), 5.79-5.61 (2s, rotomers, 2H), 5.22-5.15 (m, 2H), 4.61 (s, 1H) 4.40-4.36 (m, 1H), 4.00 (s, 2H), 3.87-3.74 (m, 4H), 3.03-2.52 (2s, rotomers, 2H); ESI MS m/z 467 $[C_{29}H_{30}N_4O_2+H]^+$.

Example 16

(E)-N-methyl-N-((3-methylbenzo[b]thiophen-2-yl)methyl)-3-(2,3,4,5-tetrahydro-1H-pyrido[2,3-e][1,4]diazepin-7-yl)acrylamide hydrochloride

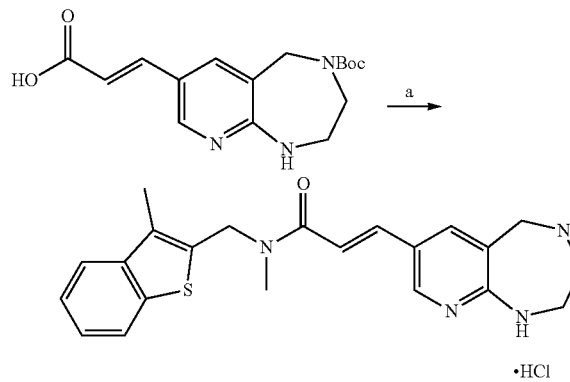

a) N-methyl(3-methylbenzo[b]thiophen-2-yl)methanamine, EDC, HOBt, DIPEA, DMF, b) TFA, $CH_2Cl_2$ (E)-tert-butyl 7-(3-(methyl((3-methylbenzo[b]thiophen-2-yl)methyl)amino)-3-oxoprop-1-enyl)-2,3-dihydro-1H-pyrido[2,3-e][1,4]diazepine-4(5H)-carboxylate

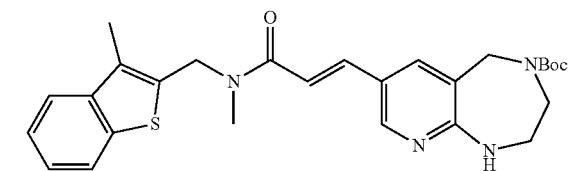 [SMILES: Cc1c(CN(C)C(=O)/C=C/c2cnc3c(c2)CN(C(=O)OC(C)(C)C)CCN3)sc2ccccc12]

The title compound was prepared using the standard method. The product was obtained as a yellow powder (240 mg, 81%): ESI MS m/z 493 $[C_{27}H_{32}N_4O_3S+H]^+$.

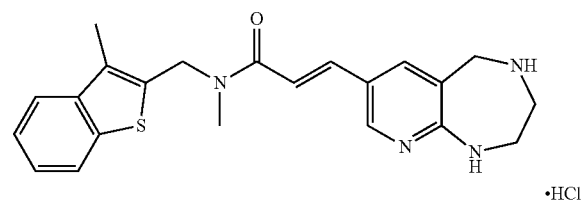 [SMILES: Cc1c(CN(C)C(=O)/C=C/c2cnc3c(c2)CNCCN3)sc2ccccc12 ; Cl]

(E)-tert-butyl-7-(3-(methyl((3-methylbenzo[b]thiphen-2-yl)amino)-3-oxoprop-1-enyl)-2,3-dihydro-1H-pyrido[2,3-e][1,4]diazepine-4(5H)-carboxylate (240 mg, 0.48 mmol) was dissolved into methylene chloride (10 mL) and treated with TFA (1 mL). The solvents were removed and the residue was dissolved into methylene chloride (150 mL), washed with 1 N NaOH (3 mL), brine (10 mL), dried over $MgSO_4$ and concentrated to a yellow oil. The oil was dissolved into methylene chloride (10 mL) and treated with 1M HCl in ether (0.4 mL). The precipitate was collected and triturated with ether to give the title compound as a yellow solid (125 mg, 50%): $^1$H NMR (400 MHz, DMSO-$d_6$) δ9.70 (bs, 2H), 8.36-8.33 (m, 1H), 8.22 (bs, 1H), 7.88-7.82 (m, 1H), 7.75-7.72 (m, 1H), 7.68-7.32 (m, 4H), 7.15-7.10 (m, 1H) 5.10-4.88 (2s, rotomers, 2H), 4.31 (bs, 2H), 3.60 (bs, 2H), 3.38 (bs, 2H), 3.14-2.92 (2s, rotomers, 3H), 2.46 (s, 3H); ESI MS m/z 393 $[C_{23}H_{24}N_4OS+H]^+$.

Example 17

Preparation of (E)-N-(3-methoxy-2-propoxybenzyl)-N-methyl-3-(2,3,4,5-tetrahydro-1H-pyrido[2,3-e][1,4]diazepin-7-yl)acrylamide hydrochloride (a) N-(3-methoxy-2-prooxybenzyl)-N-methylacrylamide, DIPEA, $Pd(OAc)_2$, $P(o\text{-tol})_3$, DMF, propionitrlle.

A solution of tert-butyl 7-bromo-2-oxo-2,3-dihydro-1H-pyrido[2,3-e][1,4]diazepine-4(5H)-carboxylate (310 mg, 0.943 mmol), N-(3-methoxy-2-propoxybenzyl)-N-methylacrylamide (393 mg, 1.49 mmol) and DIPEA (0.33 mL, 1.89 mmol) in anhydrous DMF (2.0 mL) and propionitrile (6.0 mL) was prepared in a pressure flask. Argon was bubbled onto the mixture with stirring for 30 min. Next P(o-tol)$_3$ (57.4 mg, 0.189 mmol) and Pd(OAc)$_2$ (21.2 mg, 0.0944 mmol) were added to the mixture and argon was bubbled into the reaction for an additional 5 min. The reaction was then sealed and was left to stir for 12 h at 110° C. The reaction was then allowed to cool to room temperature and was filtered through celite. The filter cake was washed with EtOAc (80 mL) and the filtrate was washed with water (50 mL) and brine (500 mL), dried over $Na_2SO_4$ and concentrated to give a brown oil. The crude product was dissolved in $CH_2Cl_2$ (0.5 mL) and TFA (6.5 mL) and was left to stir at room temperature for 1 h. The mixture was concentrated and the resulting brown oil was dissolved in EtOAc (20 mL) and washed with sat. NaHCO$_3$ (20 mL) and brine (20 mL), dried over Na$_2$SO$_4$, filtered and concentration. Purification by column chromatography (silica, gradient elution of CH$_2$Cl$_2$ to 15% MeOH/CH$_2$Cl$_2$) gave the desired product as a brown solid which was dissolved in CH$_2$Cl$_2$ (20 mL) and EtOAc (5 mL). To the mixture was added HCl (413 µl of 1M solution in ether, 0.413 mmol) and the mixture was stirred for 5 minutes and then concentrated. The resulting solid was triturated with ether and left under high vacuum overnight to give the title compound ((E)-N-(3-methoxy-2-propoxybenzyl)-N-methyl-3-(2,3,4,5-tetrahydro-1H-pyrido[2,3-e][1,4]diazepin-7-yl)acrylamide hydrochloride) (134 mg, 32%) as a brown solid and a mixture of amide rotomers: $^1$H NMR (300 MHz, DMSO-d$_6$), δ8.35-8.23 (m, 2H), 7.51-7.42 (m, 1H), 7.21-716 (m, 1H), 7.06-6.93 (m, 2H), 6.66-6.53 (m, 1H), 4.77-4.62 (m, 2H), 4.37-4.30 (m, 2H), 3.90-3.83 (m, 2H), 3.78 (s, 3H), 3.68-3.62 (m, 2H), 3.38-3.36 (m, 2H), 3.08-2.83 (m, 3H), 1.73-1.64 (m, 2H), 0.99-0.94 (m, 3H); ESI MS m/z 411 [C$_{23}$H$_{30}$N$_4$O$_3$+H]$^+$.

Example 18

(E)-3-(3,4-dimethyl-2,3,4,5-tetrahydro-1H-pyrido[2,3-e][1,4]dizepin-7-yl)-N-methyl-N-((3-methylbenzo[b]thiophen-2-yl)methyl)acrylamide hydrochloride

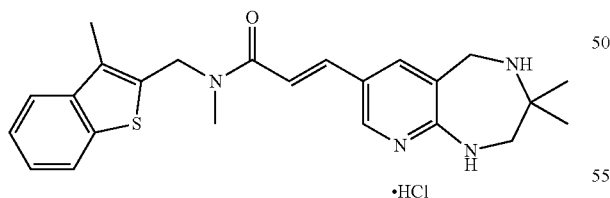

N-methyl-N-((3-methylbenzothiophene-2-yl)methyl)acrylamide, DIPEA, Pd(OAc)$_2$, P(o-tol)$_3$, DMF, propionitrile.

N-methyl-N-((3-methylbenzofuran-2-yl)methyl)acrylamide (147 mg, 0.6 mmol) and 7-bromo-3,3-dimethyl-2,3,4,5-tetrahydro-1H-pyrido[2,3-e][1,4]diazepine hydrobromide (166 mg, 0.5 mmol) were dissolved into DMF (3 mL). Diisopropylethylamine (0.26 mL, 1.5 mmol) was added and the solution was degassed with argon. Palladium acetate (11 mg, 0.05 mmol) and tri-o-tolylphosphine (30 mg) were added and the mixture was heated under microwave irradiation at 200° C. for 5 min. The reaction mixture was cooled to room temperature and filtered through celite. The filter cake was washed with ethyl acetate. The organic phase was washed with water (2×50 mL), sat. sodium bicarbonate (25 mL) and brine (50 mL), dried over MgSO$_4$ and concentrated to a brown oil. The compound was purified using a biotage silica cartridge (gradient, 95:5 CH$_2$Cl$_2$/(1% NH$_4$OH in MeOH) to 90:10). The compound was isolated as a yellow solid. The residue was dissolved in CH$_2$Cl$_2$ (3 mL) and HCl in ether was added. The precipitate was collected and triturated with ether. The title compound was isolated as a yellow solid (57 mg, 25%): $^1$H NMR (300 MHz, DMSO-d$_6$) δ9.77 (bs, 2H) 8.33 (s, 2H), 7.84-7.71 (m, 3H), 7.52-7.48 (m, 1H), 7.40-7.13 (m, 3H), 5.09-4.87 (2s, rotomers, 2H), 4.37-4.30 (m, 2H), 3.48 (bs, 2H), 3.14-2.91 (2s, rotomers, 3H), 2.41 (s, 3H), 1.39 (s, 6H); ESI MS m/z 421 [C$_{24}$H$_{28}$N$_4$OS+H]$^+$.

Example 19

Preparation of (E)-N-methyl-N-((3-methylbenzofuran-2-yl)-3-(4-(methylsulfonyl)-2,3,4,5-tetrahydro-1H-pyrido[2,3-e][1,4]diazepin-7-yl)acrylamide hydrochloride

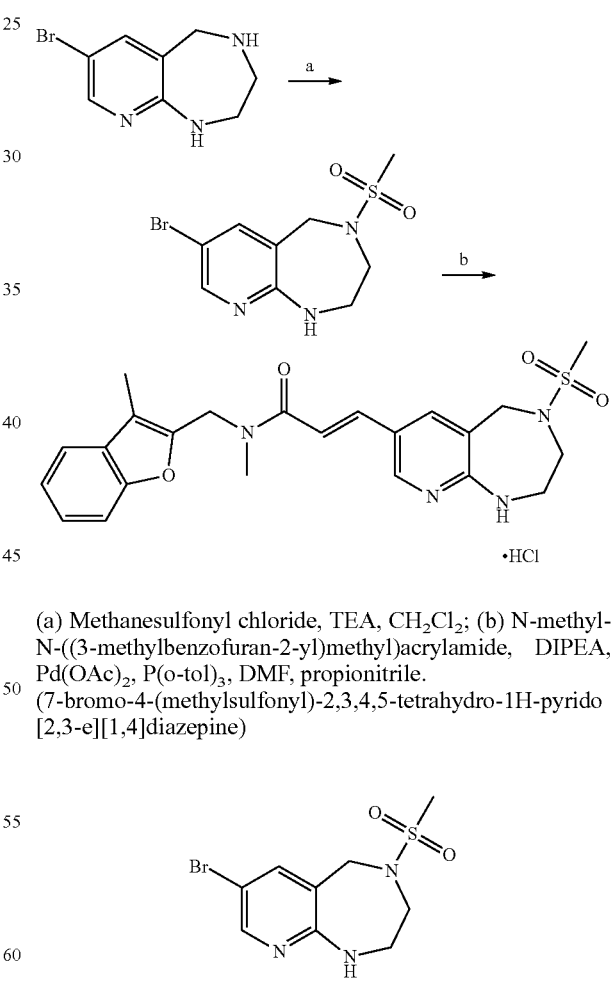

(a) Methanesulfonyl chloride, TEA, CH$_2$Cl$_2$; (b) N-methyl-N-((3-methylbenzofuran-2-yl)methyl)acrylamide, DIPEA, Pd(OAc)$_2$, P(o-tol)$_3$, DMF, propionitrile.
(7-bromo-4-(methylsulfonyl)-2,3,4,5-tetrahydro-1H-pyrido[2,3-e][1,4]diazepine)

To a solution of 7-bromo-2,3,4,5-tetrahydro-1H-pyrido[2,3-e][1,4]diazepine (432 mg, 1.89 mmol) and TEA (0.28 mL, 2.02 mmol) in anhydrous CH$_2$Cl$_2$ (20 mL) under argon was added methanesolfonyl chloride (0.16 mL, 2.06 mmol). The mixture was stirred for 12 h at room temperature. Mixture was then concentrated to a brown solid and redissolved in a 2:1 MeOH:DMSO mixture. Purification by preparative HPLC (water/acetonitrile/0.05% TFA mixture) gave the title compound (7-bromo-4-(methylsulfonyl)-2,3,4,5-tetrahydro-1H-pyrido[2,3-e][1,4]diazepine) (28.1 mg, 48%) as a yellow solid: $^1$H NMR (200 MHz, DMSO-$d_6$) δ8.02 (s, 1H), 7.08 (s, 1H), 4.39 (s, 2H), 3.48 (s, 2H), 3.39 (s, 2H), 2.79 (s, 3H).

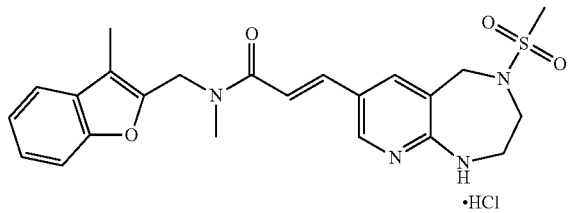 [SMILES: Cc1c(CN(C)C(=O)/C=C/c2cnc3c(c2)CN(S(C)(=O)=O)CCN3)oc2ccccc12 ; Cl]

A solution of 7-bromo-4-(methylsulfonyl)-2,3,4,5-tetrahydro-1H-pyrido[2,3-e][1,4]diazepine (2.81 mg, 0.917 mmol), N-methyl-N-((3-methylbenzofuran-2-yl)methyl)acrylamide (327 mg, 1.42 mmol) and DIPEA (0.32 mL, 1.84 mmol) in anhydrous DMF (2.1 mL) and proplonitrile (6.3 mL) was prepared in a pressure flask. Argon was bubbled into the mixture with stirring for 30 mm. Next P(o-tol)$_3$ (55.8 mg, 0.183 mmol) and Pd(OAc)$_2$ (20.6 mg, 0.0917 mmol) were added to the mixture and argon was bubbled into the reaction for an additional 5 min. The reaction was then sealed and was left to stir for 12 h at 110° C. The reaction was then allowed to cool to room temperature and was filtered through celite. The filter cake was washed with EtOAc (80 mL) and the filtrate was washed with water (50 ml) and brine (50 mL), dried over Na$_2$SO$_4$ and concentrated to give a brown oil. Purification by preparative HPLC (water/acetonitrile/0.05% TFA mixture) gave the desired product as a yellow solid which was dissolved in CH$_2$Cl$_2$ (2.0 ml). To the mixture was added HCl (440 µl of 1M solution in ether, 0.142 mmol) and the mixture was stirred for 5 min and then concentrated under high vacuum to give the title compound ((E)-N-methyl-N-(3-methylbenzofuran-2-yl)methyl)-3-(4-(methylsulfonyl)-2,3,4,5-tetrahydro-1H-pyrido[2,3-e][1,4]diazepin-7-yl)acrylamide hydrochloride) (188 mg, 42%) as a yellow solid and a mixture of amide rotomers: $^1$H NMR (400 MHz, DMSO-$d_6$) δ8.40-8.28 (m, 2H), 7.56-7.44 (m, 4H), 7.29-7.20 (m, 2H), 4.99-4.69 (m, 4H), 3.81 (m, 2H), 3.64-3.63 (m, 2H), 3.17-2.88 (m, 6H), 2.25 (s, 3H); ESI MS m/z 455 [$C_{23}H_{26}N_4O_4S$+H]$^+$.

Example 20

(E)-3-(3-spirocyclopentyl-2,3,4,5-tetrahydro-1H-pyrido[2,3-e][1,4]diazepin-7-yl)-N-methyl-N-((3-methylbenzofuran-2-yl)methyl)acrylamide trifluoroacetic acid

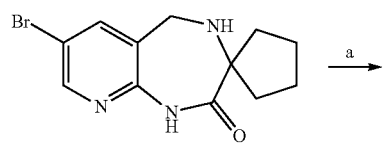

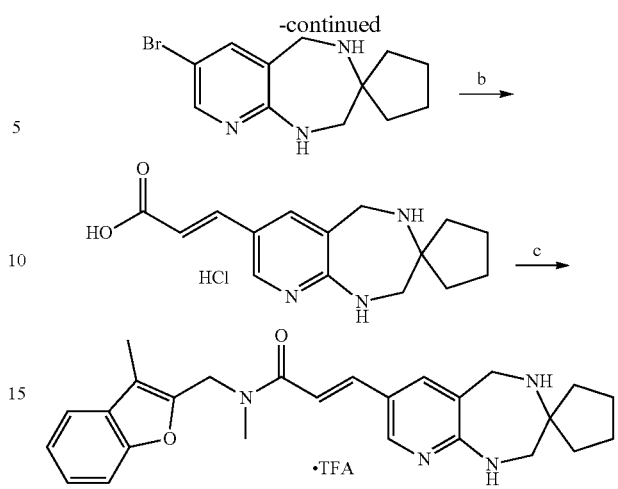

a) LAH, THF b) i) tert-butyl acrylate, Pd(OAc)$_2$, (o-Tol)$_3$P, DIPEA, EtCN, DMF ii) TFA, CH$_2$Cl$_2$ iii) HCL dioxane
Spiro-[7-bromo-2,3,4,5-tetrahydro-1H-pyrido[2,3-e][1,4]diazepin-3,1'-cyclopentane]

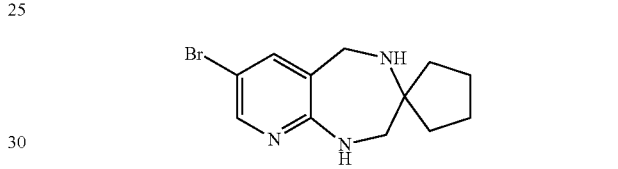

To a cooled solution of spiro[7-bromo-2-oxo-2,3,4,5-tetrahydro-1H-pyrido[2,3-e][3,4]diazepin-3,1'-cyclopentane] (850 mg, 2.87 mmol) in THF (10 mL) was added LAH (1M in THF, 316 mL, 3.16 mmol) drop wise over 20 min. The solution was stirred for 5 h at room temperature. The solution is cooled in an ice bath and carefully quenched with sat. NaHCO$_3$ (15 mL) and extracted with ethyl acetate (3×15 mL), the organic layers combined, dried over sodium sulfate and concentrated to yield the title compound as a colorless oil (736 mg, 91%): $^1$H NMR (400 MHz, DMSO-$d_6$) δ7.87 (d, J=4.0 Hz, 1H), 7.38 (d, J=4.0 Hz, 1H), 3.73 (s, 2H), 3.17 (s, 2H), 1.41-1.75 (m, 8H).
(E)-tert-butyl 3-(3-spirocyclopentyl-2,3,4,5-tetrahydro-1H-pyrido[2,3-e][1,4]diazepin-7-yl)acrylic acid hydrochloride

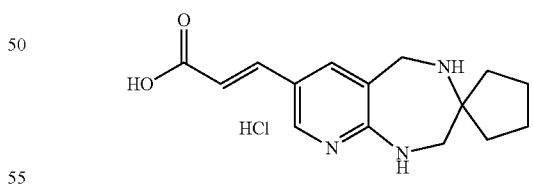

To a solution of spiro[7-bromo-2,3,4,5-tetrahydro-1H-pyrido[2,3-e][1,4]diazepin-3,1'-cyclopentane] (736 mg, 2.61 mmol), tri(o-toyl)phosphine (159 mg, 0.52 mmol), diisopropylethylamine (1.4 mL, 7.8 mmol), text-butyl acrylate (1.9 mL, 13 mmol) in DMF (5 mL) was added palladium acetate (64 mg, 0.26 mmol) and the reaction heated to 90° C. Overnight. The reaction was cooled to room temperature and passed through a pad of celite. The filter cake was washed with ethyl acetate (20 mL). The reaction was washed with water (20 mL) and extracted with ethyl acetate (2×25 mL), dried over sodium sulfate and concentrated. This solution was then re-solvated in dichloromethane (5 mL) to which trifluoroacetic acid (2 mL) was added and the reaction was stirred at room temperature overnight. The reaction was concentrated and re-solvated in dichloromethane (2 mL) to which 4M HCl in dioxane (1 mL) was added, the product precipitated out with the addition of ether (5 mL) and was further washed with ether (10 mL) and dried to yield title compound (as the HCl salt) as a white solid (560 mg, 62%): $^1$H NMR (400 MHz, CD$_3$OD) δ8.47 (s, 1H), 8.30 (s, 1H), 7.60 (d, 1H, J=16.0 Hz), 6.59 (d, 1H, J=16.0 Hz), 4.69 (s, 2H), 3.88 (s, 2H), 2.08-1.83 (m, 8H).

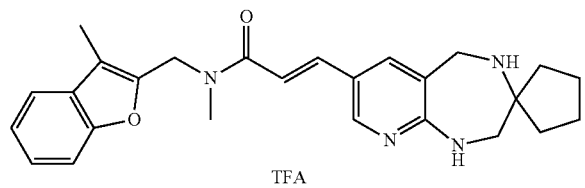 [SMILES: Cc1c(CN(C)C(=O)/C=C/c2cnc3c(c2)CNC2(CCCC2)CN3)oc2ccccc12]

TFA

To a solution of methy-(2-methyl-benzofuran-3-ylmethyl) amine (68 mg, 0.39 mmol) in DMF (3 mL) were added in sequential order (E)-tert-butyl 3-(3-spirocyclopentyl-2,3,4,5-tetrahydro-1H-pyrido[2,3-e][1,4]diazepin-7-yl)acrylic acid Hydrochloride (110 mg, 0.35 mmol), 1-hydroxybenzotriazole (54 mg, 0.39 mmol), diisopropylethylamine (240 uL, 1.4 mmol), and N-(3-dimethylaminopropyl)-N'-ethylcarbodiimide (78 mg, 0.39 mmol). The mixture was stirred at room temperature overnight, cooled in an ice bath and water added with rapid stirring. The product was extracted with ethyl acetate (3×10 mL), dried with sodium sulfate, filtered and concentrated. The product was purified using a reverse phase preparative HPLC to give the TFA salt of the title compound as a white solid (72 mg, 40%); $^1$H NMR (400 MHz, DMSO-d$_6$) δ9.26 (1s, 1H), 8.31 (s, 1H), 8.04 (s, 1H), 7.60 (d, J=8.0 Hz, 1H), 7.50-7.45 (m, 2H), 7.31-7.26 (m, 2H), 7.15 (s, 1H), 4.94-4.79 (rotamers, 2s, 2H), 4.31 (s, 3H), 3.40 (d, J=4.4 Hz, 2H), 3.17 (s, 3H), 2.26 (s, 3H), 1.88-1.64 (m, 8H); MS (ESI) m/e 431 (C$_{26}$H$_{30}$N$_4$O$_2$+H)$^+$.

Example 21

E)-N-methyl-3-((S)-3-methyl-2,3,4,5-tetrahydro-1H-pyrido[2,3-e][1,4]diazepin-7-yl)-N-((3-methyl-3a,7a-dihydrobenzofuran-2-yl)methyl)acrylamide trifluoracetic acid

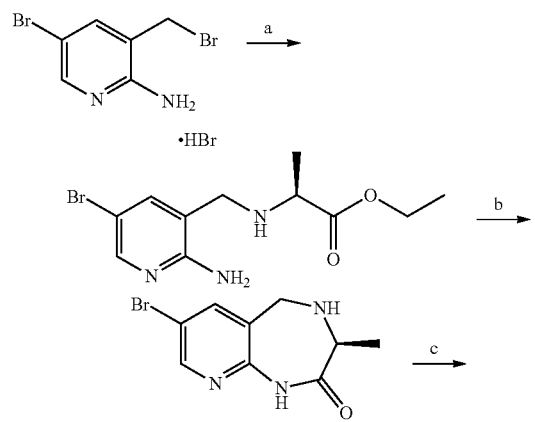

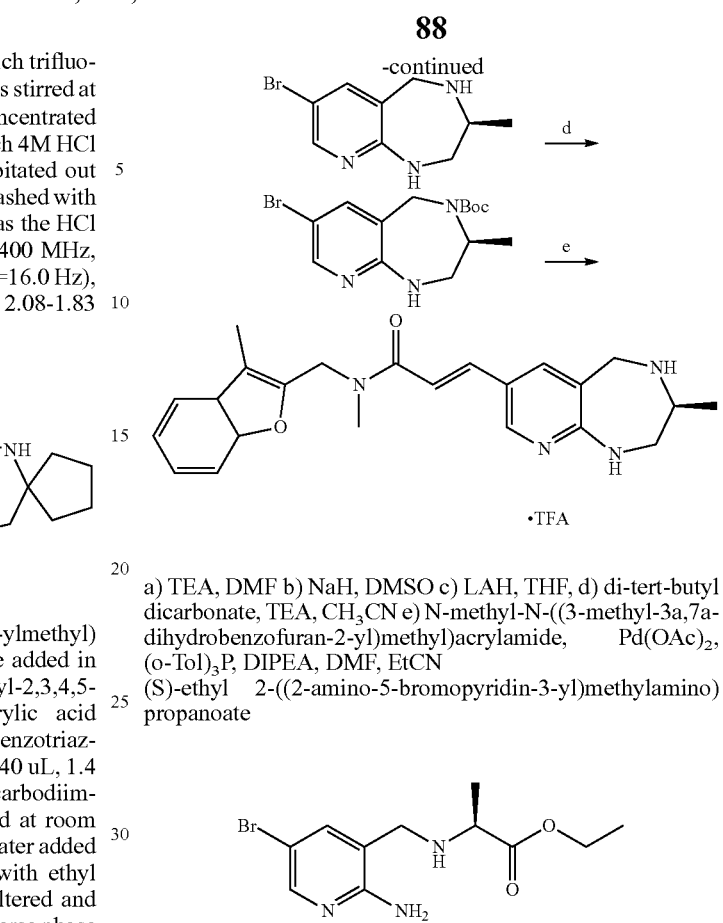

a) TEA, DMF b) NaH, DMSO c) LAH, THF, d) di-tert-butyl dicarbonate, TEA, CH$_3$CN e) N-methyl-N-((3-methyl-3a,7a-dihydrobenzofuran-2-yl)methyl)acrylamide, Pd(OAc)$_2$, (o-Tol)$_3$P, DIPEA, DMF, EtCN (S)-ethyl 2-((2-amino-5-bromopyridin-3-yl)methylamino) propanoate

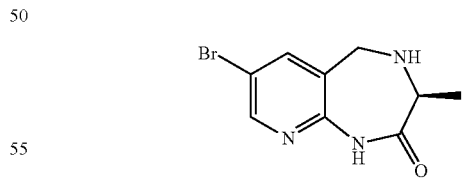

To a solution of 5-bromo-3-(bromomethyl)pyridin-2-amine hydrobromide (2.5 g, 7.3 mmol) in DMF (10 mL) is added L-alanine ethyl ester hydrochloride (1.67 g, 10.9 mmol) and triethylamine (5 mL, 36 mmol) and the reaction was stirred at room temperature overnight. The reaction was quenched with water (20 ml) and the product extracted with ethyl acetate (4×20 mL), the combined organic layers are dried over sodium sulfate and concentrated. The crude reaction mixture is purified using preparative HPLC to give the final product as a white solid (530 mg, 25%): $^1$H NMR (300 MHz, DMSO-d$_6$) δ7.91 (s, 1H), 7.47 (s, 1H), 6.20 (b, 1H), 4.15-4.07 (m, 2H), 3.49 (b, 2H), 3.27 (m, 1H), 3.34 (s, 2H), 1.17-1.24 (m, 6H).

(S)-7-bromo-3-methyl-4,5-dihydro-1H-pyrido[2,3-e][1,4]diazepin-2(3H)-one

To a solution of (S)-ethyl 2-((2-amino-5-bromopyridin-3-yl)methylamino) propanoate (530 mg, 1.75 mmol) in DMSO (10 mL) is added NaH (42 mg, 1.75 mmol) and the reaction was stirred at room temperature overnight under argon. The mixture was diluted with water (5 mL) and the product extracted with ethyl acetate (4×10 mL), dried over sodium sulfate and concentrated to yield the title compound as light brown solid (375 mg, 84%): $^1$H NMR (400 MHz, CDCl$_3$) δ8.54 (s, 1H), 8.44 (s, 1H), 3.76-3.69 (m, 2H), 3.66 (m, 1H), 1.36 (d, 3H, J=6.4 Hz).

(S)-7-bromo-3-methyl-2,3,4,5-tetrahydro-1H-pyrido[2,3-e][1,4]diazepine

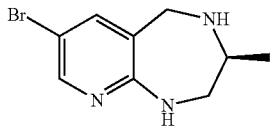

To a solution of LAH (2.5 mL, 2.52 mmol) was added a solution of (S)-7-bromo-3-methyl-4,5-dihydro-1H-pyrido[2,3-e][1,4]diazepin-2(3H)-one (375 mg, 1.26 mmol) in THF (10 mL) at 0° C. The reaction was warmed to room temperature and stirred over night. Once the reaction was complete, it was cooled to 0° C. and carefully quenched with water (10 mL), and extracted with ethyl acetate (4×15 mL), dried over sodium sulfate and concentrated. Preparative HPLC was used to purify the title compound as a white solid (166 mg, 55%): $^1$H NMR (400 MHz, CDCl$_3$) δ8.10 (d, J=2.4 Hz, 1H), 7.75 (d, J=2.4 Hz, 1H), 4.36 (2s, 2H), 4.21 (d, J=14.3 Hz, 1H), 6.33-3.61 (m, 2H), 3.26-3.13 (m, 1H), 1.36 (d, J=6.4 Hz, 3H).

(S)-tert-butyl 7-bromo-3-methyl-2,3-dihydro-1H-pyrido[2,3-e][1,4]diazepine-4(5H)-carboxylate

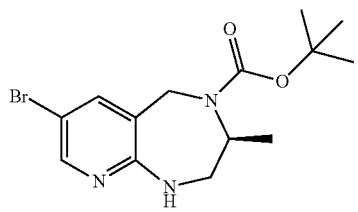 [SMILES: C[C@H]1CNc2ncc(Br)cc2CN1C(=O)OC(C)(C)C]

To a solution of (S)-7-bromo-3-methyl-2,3,4,5-tetrahydro-1H-pyrido[2,3-e][1,4]diazepine (166 mg, 0.69 mmol) in MeCN (10 mL) and triethylamine (144 uL, 1.03 mmol) was added di-tert-butyl dicarbonate (151 mg, 0.69 mmol) and the reaction was stirred at room temperature for 1 h. The reaction mixture was concentrated and re-solvated in dichloromethane (20 mL), washed with water (15 mL), dried over sodium sulfate and concentrated to give the title compound as a white solid (1.80 mg, 77%): $^1$H NMR (400 MHz, CDCl$_3$) δ7.98 (s, 1H), 7.45 (s, 1H), 4.38-4.34 (2s, 2H), 4.23 (s, 1H), 6.33-3.61 (m, 2H), 3.26-3.13 (m, 1H), 1.35 (s, 9H), 1.36 (d, J=6.4 Hz, 3H).

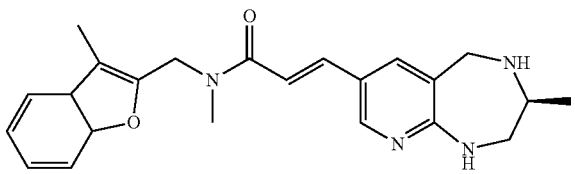 [SMILES: CC1=C(CN(C)C(=O)/C=C/c2cnc3c(c2)CN[C@@H](C)CN3)OC2C=CC=CC12]

To a solution of (S)-tert-butyl 7-bromo-3-methyl-2,3-dihydro-1H-pyrido[2,3-e][1,4]diazepine-4(5H)-carboxylate (180 mg, 0.53 mmol), tri(o-toly)phosphine (32 mg, 0.106 mmol), diisopropylethylamine (200 uL, 1.06 mmol), N-methyl-N-((3-methyl-3a,7a-dihydrobenzofuran-2-yl)methyl)acrylamide (243 mg, 1.06 mmol) in DMF (5 mL) is added palladium acetate (13 mg, 0.053 mmol) and the reaction was heated to 90° C. overnight. The reaction was cooled to room temperature and passed through a pad of celite. The filter cake was washed with ethyl acetate (10 mL). The filtrate was washed with water (10 mL) and extracted with ethyl acetate (2×15 mL), dried over sodium sulfate and concentrated. The resultant solution was then re-dissolved in methylene chloride (5 mL) and cooled to 0° C. Trifluoroacetic acid (1 mL) was added and reaction stirred at room temperature for 1 h. The solution was concentrated and purified using preparative HPLC to yield the title compound as a yellow solid (49 mg, 24%): $^1$H NMR (400 MHz, DMSO-d$_6$) δ9.43 (bs, 1H), 8.90 (bs, 1H), 8.33, (s, 1H), 8.05 (s, 1H), 7.57-7.46 (m, 3H), 7.30-7.22 (m, 2H), 7.06 (s, 1H), 4.96-4.79 (2s, 2H, rotamers), 4.35-4.21 (m, 2H), 3.62-3.58 (m, 3H), 3.17 (s, 3H), 2.26 (s, 3H), 1.28 (d, J=6.4 Hz, 3H). MS (ESI) m/e 391 $(C_{23}H_{26}N_4O_2+H)^+$.

Example 22

(R,E)-N-methyl-3-(3-methyl-2,3,4,5-tetrahydro-1H-pyrido[2,3-e][1,4]diazepin-7-yl)-N-((3-methylbenzofuran-2-yl)methyl)acrylamide trifluoroacetic acid salt

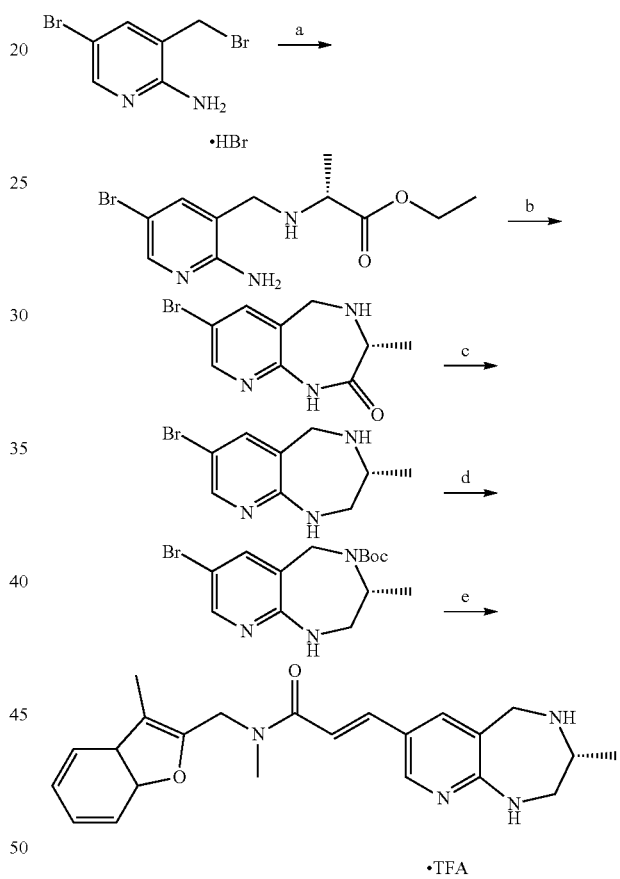

a) TEA, DMF b) NaH, DMSO c) LAH, THF, d) di-tert-buytyl dicarbonate, TEA, CH$_3$CN e) N-methyl-N-((3-methyl-3a,7a-dihydrobenzofuran-2-yl)methyl)acrylamide, Pd(OAc)$_2$, (o-Tol)$_3$, DIPEA, DMF, EtCN (R)-methyl 2-((2-amino-5-bromopyridin-3-yl)methylamino)propanoate

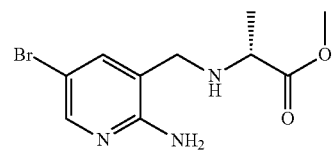

To a solution of 5-bromo-3-(bromomethyl)pyridin-2-amine hydrobromide (2.5 g, 7.3 mmol) in DMF (10 mL) was added D-alanine methyl ester hydrochloride (1.67 g, 10.9 mmol) and triethylamine (5 mL, 36 mmol) and the reaction was stirred at room temperature overnight. The reaction is quenched with water (20 mL) and the product was extracted with ethyl acetate (4×20 mL), the combined organic layers dried over sodium sulfate and concentrated. The crude reaction mixture was purified using a silica gel column eluting with ethyl acetate to give the final product as a white solid (1 g, 50%): $^1$H NMR (400 MHz, CDCl$_3$) δ8.03 (s, 1H), 7.35 (s, 1H), 5.54 (bs, 2H), 3.73 (d, 1H, J=13.2 MHz), 3.54 (d, 1H, J=13.2 Hz), 3.36-3.34 (m, 1H), 2.96 (s, 3H), 1.35 (d, 3H, J=6.8 Hz).

(R)-7-bromo-3-methyl-4,5-dihydro-1H-pyrido[2,3-e][1,4]diazepin-2(3H)-one

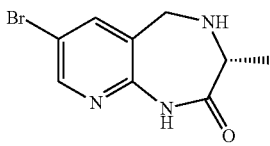

To a solution of (R)-methyl 2-((2-amino-5-bromopyridin-3-yl)methylamino) propanoate (1 g, 3.5 mmol) in DMSO (10 mL) was added NaH (174 mg, 3.9 mmol) portion wise and the reaction is stirred at room temperature overnight under argon. The mixture was diluted with water (5 mL) and the product extracted with ethyl acetate (4×10 mL), dried over sodium sulfate and concentrated to yield title compound as light brown solid (750 mg, 84%): $^1$H NMR (400 MHz, CDCl$_3$) δ8.48 (bs, 1H), 8.31 (d, 1H, J=2.4 Hz), 7.59 (d, 1H, J=2.4 Hz), 4.07-3.96 (m, 2H), 3.72-3.70 (m, 1H), 1.43 (d, 3H, J=7.2 Hz).

(R)-7-bromo-3-methyl-2,3,4,5-tetrahydro-1H-pyrido[2,3-e][1,4]diazepine

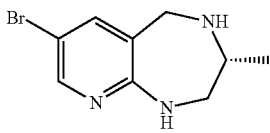

To a cooled solution (0° C.) of LAH (1M in THF, 4.4 mL, 4.4 mmol) was added a solution, of (R)-7-bromo-3-methyl-4,5-dihydro-1H-pyrido[2,3-e][1,4]diazepin-2(3H)-one (750 mg, 2.9 mmol) in THF (20 mL). The reaction was warmed to room temperature and stirred over night. Once the reaction was complete, it was cooled to 0° C. and carefully quenched with water (10 mL), extracted with ethyl acetate (4×15 mL), dried over sodium sulfate and concentrated. The product was isolated by column chromatography (10% MeOH in CH$_2$Cl$_2$) to give the title compound as a light yellow solid (161 mg, 23%): $^1$H NMR (400 MHz, CD$_3$OD) δ7.96 (s, 1H), 7.55 (s, 1H), 3.93-3.89 (d, J=15.6 Hz, 1H), 3.74-3.70 (d, J=15.2 Hz, 1H), 3.43-3.39 (d, J=13.6 Hz, 1H), 3.02 (m, 1H), 2.81-2.76 (m, 1H), 1.14-1.12 (d, J=6.8 Hz, 3H).

(R)-tert-butyl 7-bromo-3-methyl-2,3-dihydro-1H-pyrido[2,3-e][1,4]diazepine-4(5H)-carboxylate

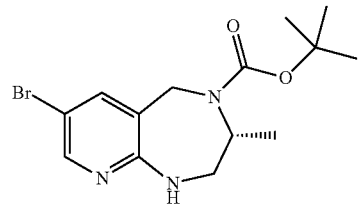 [SMILES: C[C@@H]1CNc2ncc(Br)cc2CN1C(=O)OC(C)(C)C]

To a solution of (R)-7-bromo-3-methyl-2,3,4,5-tetrahydro-1H-pyrido[2,3-e][1,4]diazepine (161 mg, 0.66 mmol) in MeCN (10 mL) and triethylamine (140 uL, 0.99 mmol) was added di-tert-butyl dicarbonate (144 mg. 0.66 mmol) and the reaction stirred at room temperature for 1 h. The reaction mixture was concentrated and re-solvated in dichloromethane (20 mL), washed with water (15 mL), dried over sodium sulfate and concentrated to give the title compound as a white solid (218 mg, 96%); $^1$H NMR (400 MHz, CDCl$_3$) δ7.96 (s, 1H), 7.46 (s, 1H), 4.36 (d, 2H, J=14.3 Hz), 4.21 (d, 1H, J=14.3 Hz), 6.33-3.61 (m, 2H), 3.26-3.13 (m, 1H), 1.35-1.34 (s, 9H), 1.37-1.35 (d, 3H, J=6.4 Hz).

(R,E)-N-methyl-3-(3-methyl-2,3,4,5-tetrahydro-1H-pyrido[2,3-e][1,4]diazepin-7-yl)-N-((3-methylbenzofuran-2-yl)methyl)acrylamide trifluoroacetic acid salt

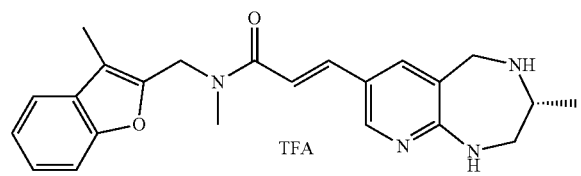 [SMILES: Cc1c(CN(C)C(=O)/C=C/c2cnc3c(c2)CN[C@H](C)CN3)oc2ccccc12]

To a solution of (R)-tert-butyl 7-bromo-3-methyl-2,3-dihydro-1H-pyrido[2,3-e][1,4]diazepine-4(5H)-carboxylate (218 mg, 0.64 mmol), tri(o-tolyl)phosphine (39 mg, 0.128 mmol), diisopropylethylamine (360 uL, 1.92 mmol), N-methyl-N-((3-mnethyl-3a,7a-dihydrobenzofuran-2-yl)methyl)acrylamide (293 mg, 1.28 mmol) in DMF (5 mL) is added palladium acetate (16 mg, 0.064 mmol) and the reaction was heated to 90° C. overnight. The reaction was cooled to room temperature and passed through a pad of celite, washing the filter cake with ethyl acetate (10 mL). The reaction was washed with water (10 mL) and extracted with ethyl acetate (2×15 mL), dried over sodium sulfate and concentrated. The residue was then re-dissolved in methylene chloride (5 mL) and cooled to 0° C. Trifluoroacetic acid (1 mL) was added and reaction stirred at room temperature for 1 h. The solution was concentrated and purified using preparative HPLC to yield a yellow solid (8 mg, 4%) as the TFA salt: $^1$H NMR (400 MHz, CD$_3$OD) δ8.35-8.32 (m, 1H), 8.00 (s, 1H), 7.58-7.53 (m, 2H), 7.40-7.21 (m, 4H), 4.92-4.77 (2s, 2H, rotamers), 4.56-4.44 (m, 2H), 3.76 (m, 1H), 3.22-3.18 (m, 2H), 2.88 (s, 3H), 2.08 (s, 3H), 1.58-1.57 (m, 3H), MS (ESI) m/e 391 (C$_{23}$H$_{26}$N$_4$O$_2$+H)$^+$.

Example 23

Preparation of (E)-N-methyl-N-((3-methylbenzofuran-2-yl)methyl)-3-(4-phenyl-2,3,4,5-tetrahydro-1H-pyrido[2,3-e][1,4]diazepin-7-yl)acrylamide

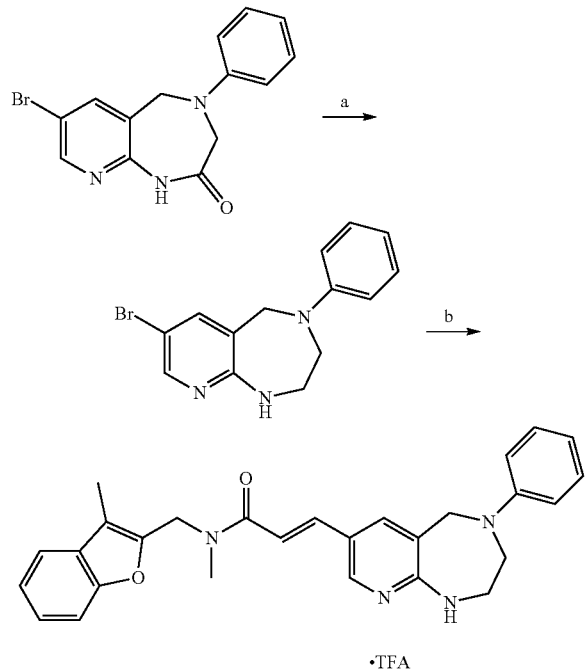

(a) LiAlH₄, TBF; (b) N-methyl-N-((3-methylbenzofuran-2-yl)methyl)acrylamide, DIPEA, Pd(OAc)₂, P(o-tol)₃, DMF, propionitrile.
(7-bromo-4-phenyl-2,3,4,5-tetrahydro-1H-pyrido[2,3-e][1,4]diazepine)

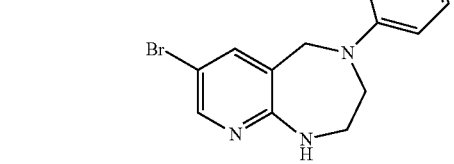

Prepared according to a standard procedure. The title compound (7-bromo-4-phenyl-2,3,4,5-tetrahydro-1H-pyrido[2,3-e][1,4]diazepine) (65.6 mg, 14%) was obtained as a yellow oil: ¹H NMR (400 MHz, DMSO-d₆) δ 7.92-7.89 (m, 2H), 7.15-7.11 (m, 2H), 6.80-6.78 (m, 2H), 6.60-6.56 (m, 1H), 6.45 (bs, 1H), 4.55 (s, 2H), 3.66-3.63 (m, 2H), 3.40-3.29 (m, 2H).
(E)-N-methyl-N-((3-methylbenzofuran-2-yl)methyl)-3-(4-phenyl-2,3,4,5-tetrahydro-1H-pyrido[2,3-e][1,4]diazepin-7-yl)acrylamide Prepared according to a standard procedure. Purification by preparative HPLC (water/acetonitrile/0.05% TFA mixture) gave the title compound ((E)-N-methyl-N-((3-methylbenzofuran-2-yl)methyl)-3-(4-phenyl-2,3,4,5-tetrahydro-1H-pyrido[2,3-e][1,4]diazepin-7-yl)acrylamide) (trifluoroacetic acid salt) (42.1 mg, 37%) as an orange solid and a mixture of amide rotamers: ¹H NMR (400 MHz, DMSO-d₆) δ 8.40-8.14 (m, 2H), 7.58-7.45 (m, 4H), 7.31-7.23 (m, 2H), 7.16-7.12 (m, 3H), 6.79-6.77 (m, 2H), 6.63-6.61 (m, 1H), 5.00-4.71 (m, 4H), 3.73-3.68 (m, 4H), 3.21-2.95 (m, 3H), 2.27 (s, 3H); ESI MS m/z 453 [C₂₈H₂₈N₄O₂+H]⁺.

Example 24

Preparation of (E)-N-((3,4-dimethylthieno[2,3-b]thiphen-2-yl)methyl)-N-methyl-3-(8-oxa-6,7,8,9-tetrahydro-5H-pyrido[2,3-b]azepin-3-yl)acrylamide

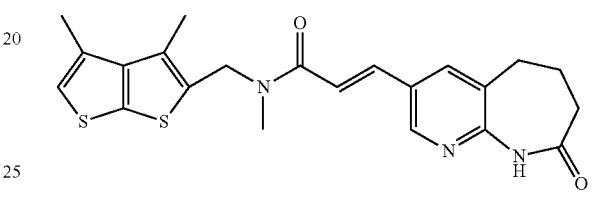

The title compound is prepared according to one of two standard procedures:

In the amide coupling reaction (E)-3-(8-oxo-6,7,8,9-tetrahydro-5H-pyrido[2,3-b]azepin-3-yl)acrylic acid hydrochloride (1 equivalent) is treated with EDC (1.2 equivalents), HOBt (1.1 equivalents), and (i-Pr)₂EtN-(5 equivalents) and the appropriate N-methyl-N-(arylmethyl)-amine (1 equivalent) in DMF. The mixture is stirred overnight at 40° C., cooled to ambient temperature and worked up in the standard fashion.

In the Heck coupling reaction, to a solution of 3-bromo-6,7-dihydro-5H-pyrido[2,3-b]azepin-8(9H)-one (2 equivalents) in proptonitrile and DMF (2:1) is added the appropriate N-arylmethyl-N-methylacrylamide (2.60 equivalent), (i-Pr)₂EtN (4.0 equivalents), Pd(OAc)₂ (0.20 equivalents) and P(o-tol)₃ (0.40 equivalents), and the mixture is de-oxygenated with argon for 15 min. The mixture os heated to reflux overnight, cooled and then filtered through a pad of diatomaceous earth. The filtrate is concentrated and the residue is worked up in the standard fashion.

Purification by preparative HPLC (water/acetonitrile/0.05% TFA mixture) gave the title compound (94 mg, >95% by HPLC) as a white solid and a mixture of amide rotamers: ESI MS m/z 426 [C₂₂H₂₃N₃O₂S₂+H]⁺.

Example 25

Preparation of (E)-3-(2,2-dimethyl-3-oxa-3,4-dihydro-2H-pyrido[3,2-b][1,4]oxazin-7-yl)-N-methyl-N-((3-methyl-1H-indol-2-yl)methyl)acrylamide

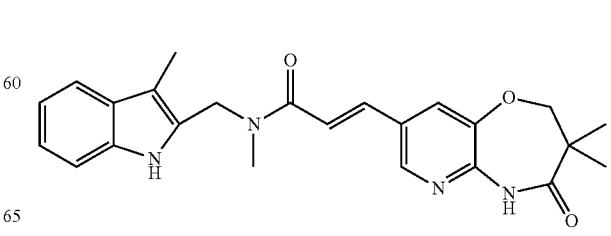

Preparation of (E)-3,3-dimethyl-4-oxo-2,3,4,3-tetrahydropyrido[3,2-b][1,4]oxazin-8-yl) acrylic acid

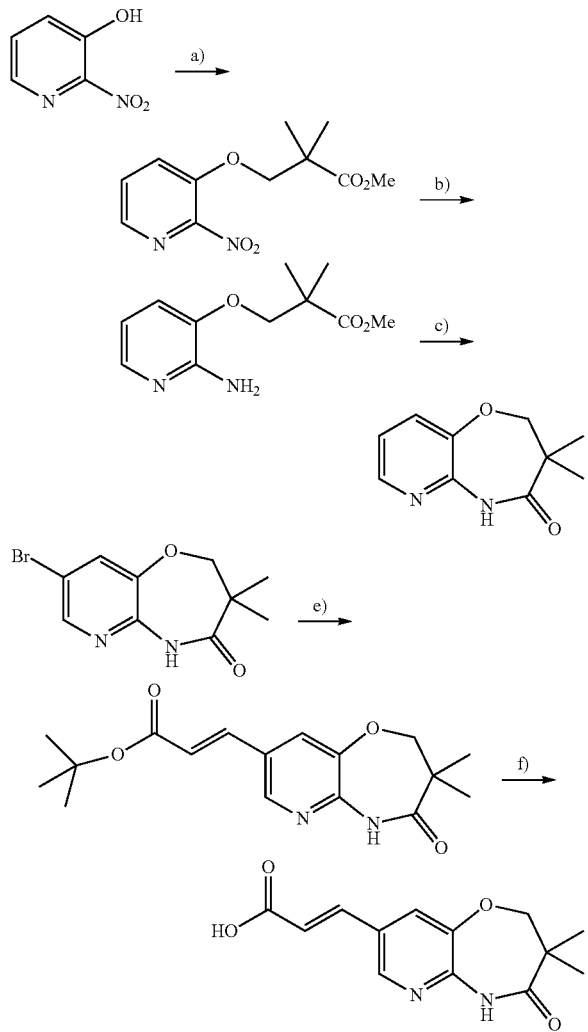

Reagents and conditions: a) methyl2,3-dimethyl-3-hydroxypropionate, DIAD, PPh$_3$, dioxane, b) Zn, AcOH, c) NaH, DMSO. d) Br$_2$, CH$_2$Cl$_2$. e) t-butylacrylate, Pd(OAc)$_2$, P(o-tol)$_3$, DMF, propionitrile. f) TFA, CH$_2$Cl$_2$, HCL/dioxane (4M)

a) methyl 2,2-dimethyl-3-(2-nitropyridin-3-ylloxy)propanoate: 3-Hydroxynitropyridine (10.0 g, 64 mmol), methyl 2,2-dimethyl-3-hydroxypropionate (9.29 & 70.4.0 mmol) and PPH$_3$ (15.15 g, 76.8 mmol) were dissolved in dioxane (500 mL), DIAD (14.5 mL, 76.8 mmol) was added at 0° C. over 5 min and the mixture was stirred at rt for 4 h then refluxed overnight. The mixture was evaporated, dissolved in ethyl acetate, washed with water, dried over magnesium sulfate and evaporated in vacuo to afford the title compound (9.1 g, 61%). $^1$H NMR (300 MHz, DMSO-d$_6$) δ8.22 (d, J=1.4 Hz, 1H), 7.98 (d, J=2.0 Hz, 1H), 7.70 (m, 1H), 4.43 (s, 2H), 3.59 (s, 3H), 1.17 (s, 6H)

b) methyl 2,2-dimethyl-3-(2-aminopyridin-3-yloxy)propanoate: A suspension of methyl 2,2-dimethyl-3-(2-nitropyridin-3-yloxy)propanoate (9.1 g, 6 mmol) and Pd/C (800 mg) in methanol (500 mL) was stirred at rt overnight under hydrogen. The cooled mixture was filtered through celite, washed with methanol and evaporated in vacuo to afford the title compound (8.23 g, 100%). $^1$H NMR (300 MHz, DMSO-d$_6$) δ7.51 (d, J=1.3 Hz, 1H), 7.03 (d, J=1.3 Hz, 1H), 6.47 (m, 1H), 5.47 (s, 2H), 3.94 (s, 2H), 3.62 (s, 3H), 1.17 (s, 6H)

c) 3,3-dimethyl-2,3-dihydropyrido[3,2-b][1,4]oxazepin-4(5H)-one: NaH (60% in oil 533 mg) was added to a solution of methyl 2,2-dimethyl-3-(2-aminopyridin-3-yloxy)propanoate (8.04, 37 mmol) in DMSO (400 mL) and the mixture stirred overnight at rt. The mixture was diluted with water and separated. The aqueous layer was washed with ethyl acetate and the combined organic phases were dried over magnesium sulfate and evaporated in vacuo to afford the title compound (6.5 g, 94%). $^1$H NMR (300 MHz, DMSO-d$_6$) δ9.83 (s, 1H), 7.96 (d, J=4.0 Hz, 1H), 7.37 (d, J=8.0 Hz, 1H), 63% (m, 1H), 4.02 (s, 2H), 1.47 (s, 6H)

d) 8-bromo-3,3-dimethyl-2,3-dihydropyrido[3,2-b][1,4]oxazepin-4(5H)-one: Bromine (13.3 mL, 83.2 mmol) was added slowly to a cooled solution of 3-dimethyl-2,3-dihydropyrido[3,2-b][1,4]oxazepin-4(5H)-one (4 g, 20.8 mmol) in CH$_2$Cl$_2$ (400 mL) with Na$_2$CO$_3$ (1 g). The mixture was stirred at rt overnight and poured into saturated NaHSO$_3$ (200 mL). The mixture was separated and the aqueous layer washed with CH$_2$Cl$_2$. The combined organic phases were dried and evaporated in vacuo to afford the title compound (4.21 g, 78%). $^1$H NMR (300 MHz, DMSO-d$_6$) δ10.13 (s, 1H), 8.10 (s, 1H), 7.77 (s, 1H), 4.05 (s, 2H), 1.47 (s, 6H)

e) (E)-tert-butyl 3,3-dimethyl-4-oxa-2,3,4,5-tetrahydropyrido[3,2-b][1,4]oxazepin-8-yl)acrylate:
A solution of 8-bromo-3,3-dimethyl-2,3-dihydropyrido[3,2-b][1,4]oxazepin-4(5H)-one (1 g, 3.6 mmol), t-butyl acrylate (1.38 g, 10.8 mmol) and DIPEA (1.86 mL, 10.1 mmol) in DMF (10 mL) was purged with Ar for 10 min. Pd(OAc)$_2$ (81 mg, 0.36 mmol) and P(o-tol)$_3$ (218 mg, 0.72 mmol) were added and the mixture purged again then refluxed overnight. The crude mixture was evaporated in vacuo and chromatographed over silica elating with methanol/dichloromethane to afford the title compound (1.0 g, 87%), $^1$H NMR (300 MHz, DMSO-d$_6$) δ10.13 (s, 1H), 8.26 (s, 1H), 7.77 (s, 1H), 7.47 (d, J=16.1 Hz, 1H), 6.53 (d, J=16.1 Hz, 1H), 4.05 (s, 2H), 1.53 (s, 9H), 1.47 (s, 6H)

f) (E)-3-(3,3-dimethyl-4-oxo-2,3,4,5-tetrahydropyrido[3,2-b][1,4]oxaxepin-8-yl)acrylic acid:
TFA (3 mL) was added to a cooled solution of (E)-tert-butul 3-(3,3-dimethyl-4-oxo-2,3,4,5-tetrahydropyrido[3,2-b][1,4]oxazepin-8-yl)acrylate (1 g, 3 mmol) in CH$_2$Cl$_2$ (5 mL) and stirred for 30 min at rt. The mixture was evaporated and HCl/dioxane (4M, 5 mL) was added. The precipitate thai formed was washed with ether and dried to afford the title compound (530 mg, 66%). $^1$H NMR (300 MHz, DMSO-d$_6$) δ8.45 (s, 1H), 8.28 (s, 1H), 7.82 (d, J=15.5 Hz, 1H), 6.84 (d, J=20 Hz, 1H), 4.05 (s, 2H), 1.47 (s, 6H).

Preparation of (E)-3-(2,2-dimethyl-3-oxo-3,4-dihydro-2H-pyrido[3,2-b][1,4]oxazn-7-yl)-N-methyl-N-((3-methyl-1H-indol-2-yl)methyl)acrylamide

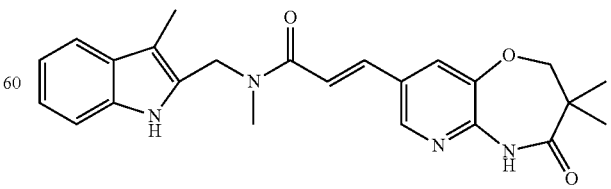

EDC (402 mg, 1.0 mmol) was added to a solution of N-methyl (3-methyl-1H-indol-2-yl)methanamine (135 mg, 0.7 mmol), (E)-3-(3,3-dimethyl-4-oxo-2,3,4,5-tetrahydropyrido[1,4]oxazepin-8-yl)acrylic acid hydrochloride (240 mg, 0.8 mmol), HOBT.H₂O (101 mg, 0.7 mmol) and DIPEA (0.58 mL, 2.7 mmol) in dry DMF (5 mL), After stirring overnight, water was added. The precipitate that formed was washed with ethyl acetate and dried to afford the title compound (234 mg, 79%). ¹H NMR (300 MHz, DMSO-d₆) δ10.62-10.58 (rotamers, s, 1H), 10.09 (s, 1H), 8.26 (s, 1H), 7.89 (s, 1H); 7.51-7.49 (m, 2H), 7.28 (t, J=8.0 Hz, 1H), 7.03-6.90 (m, 3H), 4.90-4.73 (rotamers, s, 2H), 4.05 (s, 3H), 2.23 (s, 3H), 1.17 (s, 6H); MS (ESI): m/e 419.4 (C₂₄H₂₆N₄O₃+H)⁺

Example 26

Preparation of (R,E)-(3,3-dimethyl-4-oxo-2,3,4,5-tetrahydropyrido[3,2-b][1,4]oxazepin-8-yl)-N-(1(3-ethylbenzofuran-2-yl)ethyl)-N-methylacrylamide

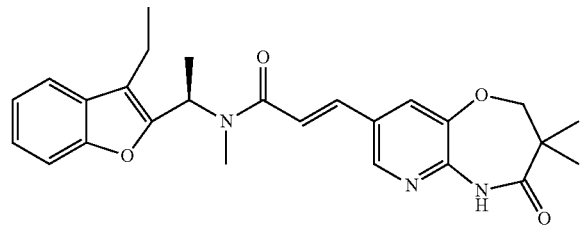 [SMILES: CCc1c([C@@H](C)N(C)C(=O)/C=C/c2cnc3c(c2)OCC(C)(C)C(=O)N3)oc2ccccc12]

EDC (557 mg, 1.4 mmol) was added to a solution of (R)-1-(3-ethylbenzofuran-2-yl)-N-methylethananamine (225 mg, 1.1 mmol), (E)-(3,3-dimethyl-4-oxo-2,3,4,5-tetrahydropyrido[3,2-o][1,4]oxazepin-8-yl)acrylic acid hydrochloride (318 mg, 1.2 mmol), HOBT.H₂O (148 mg, 1.1 mmol) and DIPEA (1.1 mL, 4.4 mmol) in dry DMF (5 mL). After stirring overnight, water was added. The precipitate that formed was washed with ethyl acetate and dried to afford the title compound (231 mg, 46%). ¹H NMR (300 MHz, DMSO-d₆) δ10.17 (s, 1H), 8.33 (s, 1H), 8.00 (s, 1H), 7.84 (d, J=7.4 Hz, 1H), 7.65 (d, J=7.1 Hz, 1H), 7.41-7.34 (m, 2H), 7.10-6.98 (m, 2H), 6.29 (m, 1H), 4.14-3.99 (m, 2H), 3.09 (s, 2H), 1.73 (m, 3H), 1.43 (s, 6H); MS (ESI): m/e 448.3 (C₂₆H₂₉N₃O₄+H)⁺.

Example 27

Preparation of (E)-N-methyl-N-((3-methylbenzo[b]thiophen-2-yl)methyl)-3-(4-oxo-1,2,3,4,5,6-hexahydropyrido[2,3-b][1,5]diazocin-8-yl)acrylamide, di-methane sulfonic salt

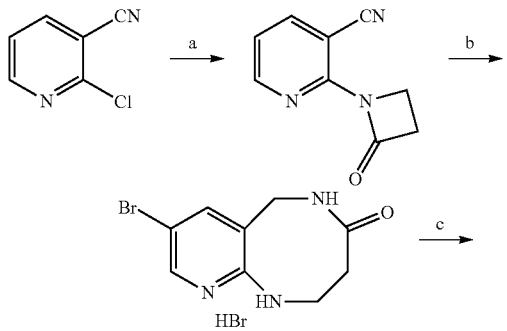

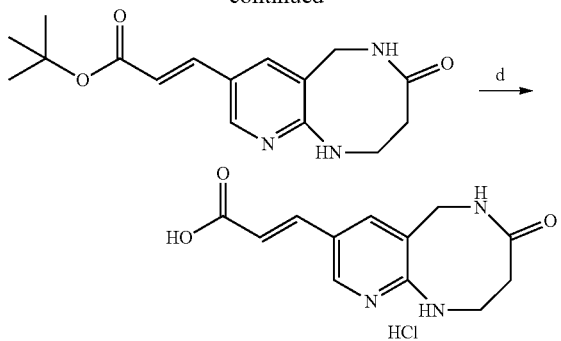

(a) Azetidin-2-one, Pd(dba), Xantphos, Cs₂(CO₃), Toluene, 90° C.; (b) (i) Pd/C, HOAc; (ii) Br₂ (c) tert-butyl acrylate, Pd(OAc)₂, P(o-tol)₃, (i-Pr)₂EtN, DMF, 100° C.; (d) i. TFA, CH₂Cl₂; ii. 4 M HCl/dioxane.

Preparation of 2-(2-oxoazetidin-1-yl)nicotinonitrile

Step A. An oven dried roundbottom flask was purged with argon then charged with 2-chloronicotinonitrile (277 mg, 2.0 mmol), azetidin-2-one (142 mg, 2.0 mmol), Palladium dibenzylideneacetone (115 mg, 0.1 mmol), Xantphos (174 mg, 0.3 mmol) and cesium carbonate (1.3 g, 4.0 mmol) followed by toluene (10 mL). The suspension was heated at 90° C. for 16 hours (overnight). After cooling, the yellow suspension was filtered through a pad of celite and the filter cake was rinsed with CH₂Cl₂. The filtrate was concentrated and subjected to flash chromatography on silica gel using 5% MeOH:95% CH₂Cl₂ to give a yellow solid. Yield: 100 mg (28.9%) ¹H-NMR (400 MHz, DMSO-d₆) δ8.65 (dd, 1H, J=1.6 Hz, 3.2 Hz), 8.30 (dd, 1H, J=6.0 Hz, 2.0 Hz), 7.35 (m, 1H), 3.88 (t, 2H, J=5.2 Hz), 3.18 (t, 2H, J=5.2 Hz).

Preparation of 8-bromo-2,3,5,6-tetrahydropyrido[2,3-b][1,5]diazocin-4(1H)-one hydrobromide Step B. A sound bottom Bask was purged with argon and charged with 2-(2-oxoazetidin-1-yl)nicotinonitrile (600 mg, 3.46 mmol) and palladium (10%) on activated carbon (250 mg, 0.23 mmol) followed by acetic acid (15 mL). The flask was stirred under a hydrogen balloon overnight. A TLC analysis indicated that the starting material has been consumed. The mixture was filtered through a pad of celite and the filtrate was treated with bromine (0.27 mL, 5.19 mmol) dropwise over 20 minutes. The yellow-orange suspension was stirred for 3.5 hours at room temperature. The suspension was then treated with 150 mL Et2O and stirred rapidly then sonicated. The solvent was decanted and the solid was filtered and washed with 200 mL Et₂O. The solid was collected and dried under reduced pressure. Yield: 600 mg (51.3%), ¹H-NMR (400 MHz, DMSO-d₆) δ8.06 (d, J=2.4 Hz), 7.75 (d, 1H, J=2.4 Hz), 7.43 (t, 1H, J=7.6 Hz), 4.48 (d, 2H, J=7.6 Hz), 3.65 (t, 2H, J=8.0 Hz), 2.74 (t, 2H, J=8.0 Hz)

Preparation of (E)-tert-butyl 3-(4-oxo-1,2,3,4,5,6-hexahydropyrido[2,3-b][1,5]diazocin-8-yl)acrylate Step C. A round bottom flask was charged with 8-bromo-2,3,5,6-tetrahydropyrido[2,3-b][1,5]diazocin-4(1H)-one hydrobromide (0.5 g, 1.48 mmol), tert-butyl acrylate (1.1 mL, 7.42 mmol), and (i-Pr)₂EtN (1.5 mL, 8.88 mmol) followed by 15 mL DMF. The solution was de-oxygenated with argon for 20 minutes. The mixture was treated with Pd(OAc)₂ (17 mg, 0.07 mmol) and P(o-tol)₃ (45 mg, 0.15 mmol) then heated to 100° C. for 18 hours (overnight). After cooling, the dark mixture was treated with activated charcoal (100 mg) and filtered through celite. The filitrate was partitioned between 150 mL CH₂Cl₂ and 50 mL H₂O in a separatory funnel. The organic layer was separated and treated with 3×50 mL saturated sodium chloride solution then dried over MgSO$_4$ and concentrated to give a brown residue. This residue was triturated with 20% Et$_2$O:hexanes to give a solid. The solid was collected and subjected to flash chromatography on silica gel using 5% MeOH:95% CH$_2$Cl$_2$. Yield: 200 mg (44.5%); $^1$H-NMR (400 MHz, DMSO-d$_6$) δ8.12 (d, 1H, J=2.4 Hz), 7.74 (d, 1H, J=2.4 Hz), 7.44 (m, 1H), 7.41 (d, 1H, J=16.0 Hz), 6.94 (t, 1H, J=6.4 Hz), 6.29 (d, 1H, J=15.6 Hz), 4.46 (d, 2H, J=7.6H z), 3.61 (m, 2H), 2.73 (t, 2H, J=7.2 Hz), 1.46 (s, 9H): ESI MS m/z 304 [C$_{16}$H$_{21}$N$_3$O$_3$+H]$^+$ Preparation of (E)-3-(4-oxo-1,2,3,4,5,6-hexahydropyrido[2,3-b][1,5]diazocin-8-yl)acrylic acid hydrochloride Step D. A suspension of (E)-tert-butyl 3-(4-oxo-1,2,3,4,5,6-hexahydropyrido[2,3-b][1,5]diazocin-8-yl)acrylate (175 mg, 0.58 mmol) in 3 mL CH$_2$O$_2$ was treated with 3 mL of trifluoroacetic acid. The mixture became homogeneous and it was stirred at room temperature for 20 minutes. The solution was concentrated to dryness and treated with 1 mL 4M HCl in dioxane to give a creamish solid. The suspension was diluted with 10 mL Et$_2$O and sonicated. The solid was filtered and dried under reduced pressure overnight. Yield: 165 mg (100%) $^1$H-NMR (400 MHz, DMSO-d$_6$) δ8.28-8.27 (2×s, 2H), 8.26 (br s, 1H), 7.60 (t, 1H, J=7.6 Hz), 7.51 (d, 1H, J=16.0 Hz), 6.50 (d, 1H, J=16.0 Hz), 4.62 (br s, 2H), 3.85 (br s, 2H), 2.79 (t, 2H, J=7.2 Hz)

Preparation of (E)-N-methyl-N-((3-methylbenzofuran-2-yl)-3-(4-oxo-1,2,3,4,5,6-hexahydropyrido[2,3-b][1,5]diazocin-8-yl)acrylamide di-methane sulfonic acid salt

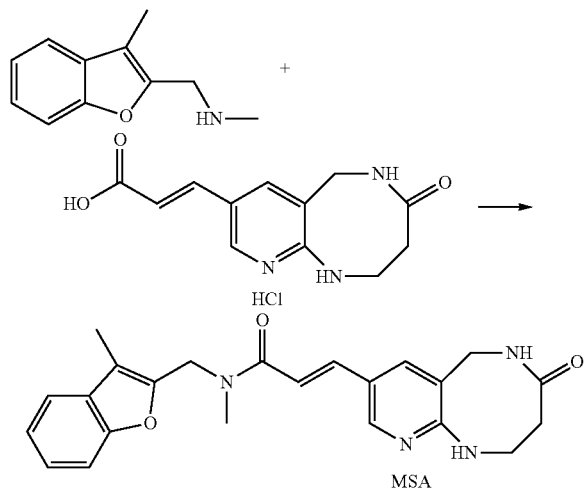

Conditions: (i) EDC, HOBt, (i-Pr)$_2$EtN, DMF, 40° C.; (ii) Mentanesulfonic acid, CH$_2$Cl$_2$, iPrOH.

The amide was prepared according to the general coupling procedure in a yield of 63%. To a cooled solution of (E)-N-methyl-N-((3-methylbenzofuran-2-yl)methyl)-3-(4-oxo-1,2,3,4,5,6-hexahydropyrido[2,3-b][1,5]diazocin-8-yl)acrylamide (70 mg, 0.17 mmol) in 10 mL CH$_2$Cl$_2$/2 mL isonropanol mixture was added methanesulfonic acid (45 μL, 0.69 mmol). The solution was stirred for 1 hour at 0° C. then treated with 20 mL Et$_2$O with rapid stirring. A precipitate formed and it was filtered, washed with Et$_2$O (20 ml), collected and dried under reduced pressure to give a beige solid. Yield: 100 mg (99%). $^1$H NMR (400 MHz, DMSO-d$_6$) δ8.49-8.28 (m, 2H), 7.70-7.22 (m, 6H), 4.79 and 4.66 (2×s, 2H), 4.55 (br s, 2H), 3.88 (br s, 2H), 3.19 and 2.93 (2×s, 3H), 2.81 (br s, 2H), 2.37 (s, 6H), 2.20 (s, 3H): ESI MS m/z 405 [C$_{23}$H$_{24}$N$_4$O$_3$+H]$^+$ Example 28

Preparation of (E)-N-methyl-N-((3-methylbenzo[b]thiophen-2-yl)-3-(4-oxo-1,2,3,4,5,6-hexahydropyrido[2,3-b][1,5]diazocin-8-yl)acrylamide, di-methane sulfonic salt

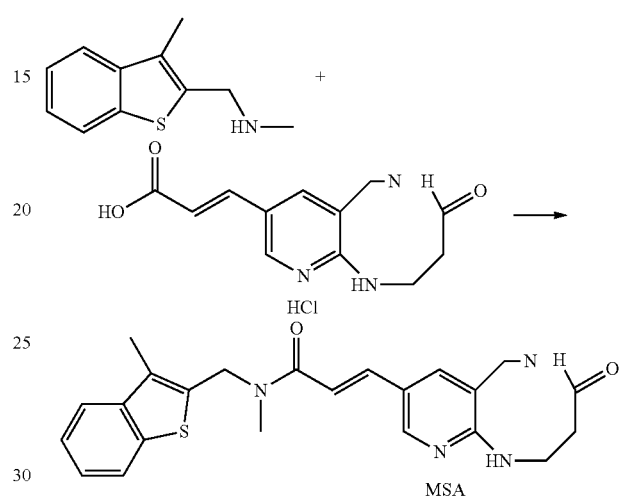

Conditions: (i) EDC, HOBt, (i-Pr)$_2$EtN, DMF, 40° C.; (ii) Methanesulfonic acid, CH$_2$Cl$_2$, iPrOH Prepared according to the procedure for the preparation of Example 27. $^1$H NMR (400 MHz, DMSO-d$_6$) δ8.41-7.21 (m, 8H), 5.11 and 4.89 (2×s, 2H), 4.62 (br s, 2H), 3.85 (br s, 2H), 3.15 and 2.92 (2×s, 3H), 2.80 (br s, 2H), 2.44 (s, 3H), 2.34 (s, 6H); ESI MS m/z 421 [C$_{23}$H$_{24}$N$_4$O$_2$S+H]$^+$ Example 29

Preparation of (R,E)-3-(3,3-dimethyl-2-oxo-1,2,3,5-tetrahydropyrido[2,3-e][1,4]oxazepin-7-yl)-N-(1-(3-methoxy-2-propoxyphenyl)-N-methylacrylamide

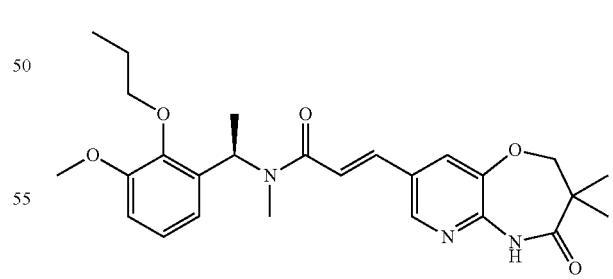

EDC (0.14 g, 0.73 mmol) was added to a suspension of (E)-3-(3,3-dimethyl-2-oxo-1,2,3,5-tetrahydropyrido[2,3-e][1,4]oxazepin-7-yl)acrylic acid hydrochloride (0.16 g, 0.61 mmol), HOBt (0.091 g, 0.67 mmol), (R-1-(3-methoxy-2-propoxyphenyl)-N-methylethanamine (0.15 g, 0.67 mmol) and (i-Pr)$_2$EtN (0.62 mL, 3.7 mmol) in DMF (5 mL). The mixture was allowed to stir overnight at 35° C. The mixture was cooled to 0° C. and diluted with H$_2$O (30 mL) with rapid stirring. The resulting precipitate was filtered, washed with H$_2$O (20 mL) then dried under high vacuum. The solid was then triturated with Et$_2$O, and the resultant solid was collected, to yield 125 mg (44%); $^1$H-NMR (300 MHz, DMSO-d$_6$) δ10.08 (s, 1H), 8.25 (s, 1H), 7.92 and 7.86 (2×s, 1H), 7.47-6.97 (m, 5H), 6.01 and 5.77 (2×s, 1H), 4.07 (s, 2H), 3.83 and 3.73 (2×m, 2H), 3.78 (s, 3H), 2.81 and 2.58 (2×s, 3H), 1.65-1.38 (m, 5H), 1.19 (s, 6H), 0.86 and 0.77 (2×m, 3H); ESI MS m/z 468 [C$_{26}$H$_{33}$N$_3$O$_5$+H]$^+$ Example 30

(E)-N-methyl-N-((3-methylbenoz[b]thiophen-2-yl)methyl)-3-(2,3,4,5-tetrahydro-1H-pyrido[2,3-b][1,4]diazepin-8-yl)acrylamide

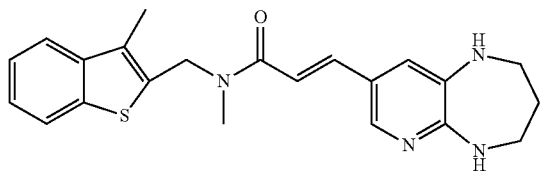 [SMILES: Cc1c(CN(C)C(=O)/C=C/c2cnc3c(c2)NCCCN3)sc2ccccc12]

A solution of 8-bromo-2,3,4,5-tetrahydro-1H-pyrido[2,3-b][1,4]diazepine (0.075 g, 0.31 mmol), N-methyl-N-((3-mthylbenzo[b]thiophen-2-yl)methyl)acrylamide (0.15 g, 0.62 mmol, (i-Pr)$_2$EtN (0.16 mL, 0.93 mmol) in DMF (1.5 mL) and EtCN (1.5 mL) was de-oxygenated with Ar for 30 min. Pd(OAc)$_2$ (7 mg, 0.031 mmol) and P(o-tol)$_3$ (19 mg, 0.062 mmol) was added and the solution was de-oxygenated for an additional 15 min. The reaction was heated to 100° C. for 18 hrs at which time the reaction was cooled to room temperature and then filtered through a short column of silica washing with EtOAc (20 mL). The filtrate was washed with brine (2×30 mL), dried (MgSO$_4$) and the solvent removed in vacuo. Purification by column chromatography (silica gel, CH$_2$Cl$_2$/MeOH, 98:2) gave the title compound (27 mg, 22%) as a yellow powder; $^1$H NMR (400 MHz, DMSO-d$_6$) δ7.87 (d, J=7.5, 1H), 7.75-7.72 (m, 2H), 7.47-7.23 (m, 4H), 6.94 and 6.82 (2×d, J=14 Hz, 1H), 6.22 (s, 1H), 5.24 (s, 1H), 5.03 and 4.85 (2×m, 2H), 3.18-2.90 (m, 7H), 2.45 (s, 3H), 1.68 (s, 2H); ESI MS m/s 393 [C$_{22}$H$_{24}$N$_4$OS+H]$^+$ Example 31

Preparation of (E)-N-methyl-3-(5-methyl-4-oxo-1,2,3,4,5,6-hexahydropyrido[2,3-b][1,5]diazocin-8-yl)-N-((3-methylbenzofuran-2-yl)methyl)acrylamide hydrochloride

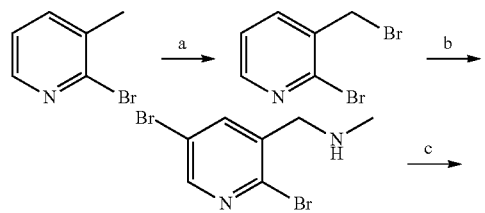

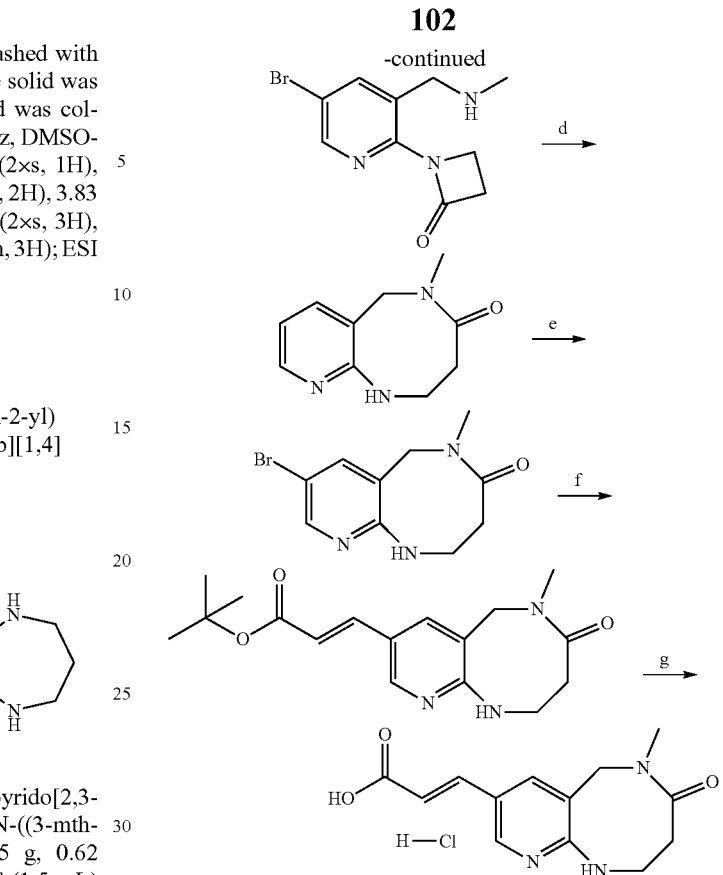

(a) NBS, BPO, CHCl$_3$; (b) MeNH$_2$, MeOH/H$_2$O; (c) CuI, N,N$^1$-dimethyldiamine, K$_2$CO$_3$, tol; (d) Ti(o-iPr)$_4$, tol; (e) Br$_2$, acetic acid; (f) tert-butyl acrylate, Pd(OAc)$_2$, P(o-tol)$_3$, (i-Pr)$_2$EtN, DMF; (g) (i). TFA, CH$_2$Cl$_2$; (ii). 4 M HCl/dioxane.

Preparation of 2-bromo-3-(bromomethyl)pyridine

Step. A: A solution of 2-bromoo-3-methylpyridine (1.0 mL, 8.98 mmol), benzoyl peroxide (217 mg, 0.90 mmol), and N-bromosuccinimide (1.76 g, 9.88 mmol) in 40 ml of chloroform was heated at reflux for 18 h. At which point the solution was cooled to room temperature and the solution was diluted with 100 mL of water. The separated organic layer was then washed with NaCO$_3$(aq) and brine, dried over MgSO$_4$, and concentrated in vacuo. The orange oil crude product is used directly in the next step without further purification.

Preparation of (2,5-dibromopyridin-3-yl)-N-methylmethanamine

Step B: A solution of previously made-2-bromo-2-3(bromomethyl)pyridine (8.98 mmol) in 5 mL of methanol was added dropwise to a solution of methyl amine (excess) in 5 mL methanol:water, 1:1 ratio. The resulting solution was let stir for 19 h at room temperature. The solution was concentrated down in vacuo to ~5 ml, and diluted with dichloromethane (25 mL) and water (25 ml). The organic layer was dried over MgSO$_4$, and concentrated in vacuo to yield the crude orange oil product. This oil was subjected to flash chromatography on silica gel using 50% ethyl acetate:hexanes to give the title compound as an orange oil. Yield 1.1 g (61% for 2 steps); $^1$H NMR (300 MHz, DMSO-d$_6$) δ8.33 (d, J=4.8 Hz, 1H), 7.93 (d. J=7.3 Hz, 1H), 7.50 (m, 1H), 3.93 (s, 2H), 2.46 (s, 3H): ESI MS m/z 201, 203 [C$_7$H$_9$N$_2$Br+H]$^+$ Preparation of 2-(5-bromo-3-((methylamino)methyl)pyridin-2-yl)cyclobutanone Step C: A solution of (2,5-dibromopyridin-3-yl)-N-methylmethanamine (95 mg, 0.47 mmol), azetidinone (34 mg, 0.47 mmol), $Cs_2CO_3$ (308 mg, 0.94 mmol) in 5 mL of toluene was degassed with bubbling argon for 30 mm followed by the addition of $Pd_2(dba)_3$ (6 mg, 0.01 mmol) and Xantphos (12 mg, 0.02 mmol). The resulting yellow solution was then stirred at 90° C. 18 h. The dark coloured solution was removed from the heat and poured over a pad of celite washing with 50 mL of ethyl acetate. The filtrate was diluted with 50 mL of water, the organic layer was washed with brine, dried over $MgSO_4$, and concentrated in vacuo. The crude product was purified using flash chromatography on silica gel using 95% dichloromethane:methanol to obtain the product as a orange sticky solid. Yield 66 mg (73%); $^1$H NMR (400: MHz, DMSO-$d_6$) δ8.09 (d, J=4.8 Hz, 1H), 7.28 (d, J=7.2 Hz, 1H), 6.78 (m, 1H), 4.92 (bs, 1H), 4.51 (s, 2H), 3.58 (q, J=6.0 Hz, 2H), 3.04 (t, J=8.8 Hz, 2H), 2.84 (s, 3H); ESI MS m/z 192 $[C_{10}H_{13}N_3O+H]^+$ Preparation of 5-methyl-2,3,5,6-tetrahydropyrido[2,3-bh][1,5]diazocin-4(1H)-one Step D: A solution of 2-(5-bromo-3-((methylamino)methyl)pryrin-2-yl)cyclobutanone (66 mg, 0.35 mmol) and Ti(o-iPr)$_4$ (50 μL, 0.17 mmol) in toluene under argon was stirred at 110° C. for 20 h. The yellow solution was cooled to room temperature and concentrated in vacuo. The crude mixture was then redissolved in 1.0 mL of DCM:methanol (90:10) and passed through a silica gel plug and rinsed with a further 40 mL of the DCM/methanol solution to obtain the product as an off-white solid. Yield 63 mg (96%); $^1$H NMR (400 MHz, CDCl$_3$) δ8.08 (d, J=4.8 Hz, 1H), 7.70 (d, 7.2 Hz, 1H), 6.77 (m, 1H), 4.96 (bs, 1H), 4.50 (s, 2H), 3.57 (q, J=6.4 Hz, 2H), 3.03 (t, J=6.8 Hz, 2H), 2.84 (s, 3H); ESI MS m/z 192 $[C_{10}H_{13}N_3O+H]^+$ Preparation of 8-bromo-5-methyl-2,3,5,6-tetrahydropyrido[2,3-b][1,5]diazocin-4(1H)-one Step E: Bromine (189 μL, 3.7 mmol) was added to a solution of 5-methyl-2,3,5,6-tetrahydropyrido[2,3-b][1,5]diazocin-4(1H)-one (460 mg, 2.4 mmol) in 10 mL of acetic acid and stirred at room temperature for 17 h. Add 30 mL of diethyl ether and collect orange solid product via suction filtration. Redissolve the solid in DCM and wash with NaHCO$_3$, dry the organic layer over MgSO$_4$, and concentrate in vacuo to obtain orange solid product. Yield 670 mg (quant); $^1$H NMR (400 MHz, CDCl$_3$) δ8.10 (d, J=2.0 Hz, 1H), 7.50 (d, J=2.4 Hz, 1H), 5.17 (bs, 1H), 4.49 (s; 2H), 3.59 (bm, 2H), 3.04 (t, J=6.8 Hz, 2H), 2.85 (s, 3H); ESI MS m/z 270, 272 $[C_{10}H_{12}N_3OBr+H]^+$ Preparation of (E)-tert-butyl-3-(5-methyl-4-oxo-1,2,3,4,5,6-hexahydropyrido[2,3-b][1,5]diazocin-8-yl)acrylate Step F: A suspension of 8-bromo-5-methyl-2,3,5,6-tetrahydropyrido[2,3-b][1,5]diazocin-4(1H)-one (670 mg, 2.48 mmol), tert-butyl acrylate (1.8 mL, 12.4 mmol) and (i-Pr)$_2$EtN (1.3 mL, 7.44 mmol) in 30 mL of DMF:Propionitriole (4:1) was de-oxygenated with Ar for 30 min. The mixture was treated with Pd(OAc)$_2$ (19.4 mg, 0.09 mmol) and P(o-tol)$_3$ (51.7 mg, 0.18 mmol) then heated to 110° C. for 16 h. The hot mixture was filtered through a pad of celite. The filtrate was diluted with 100 mL H$_2$O then extracted with 2×100 mL ethyl acetate. The resulting brown solid was triturated with a solution of hexanes ethyl acetate (4:1) followed by filtration to yield the brown solid product. Yield 391 mg (50%); $^1$H NMR (400 MHz, CDCl$_3$) δ8.17 (s, 1H), 7.51 (s, 1H), 7.49 (d, J=16.4 Hz, 1H), 6.26 (d, J=16.0 Hz, 1H), 5.22 (bm, 1H), 4.55 (s, 2H), 3.66 (q, J=7.2 Hz, 2H), 3.07 (t, J=7.2 Hz, 2H), 2.81 (s, 3H), 1.55 (s, 9H); ESI MS m/z 318 $[C_{17}H_{23}N_3O_3+H]^+$ Preparation of (E)-3-(5-methyl-4-oxo-1,2,3,4,5,6-hexahydropyrido[2,3-b][1,5]diazocin-8-yl)acrylic acid hydrochloride Step G: A suspension of (E)-tert-butyl 3-(5-methyl-4-oxo-1,2,3,4,5,6-hexahydropyrido[2,3-b][1,5]diazocin-8-yl)acrylate (391 mg, 1.23 mmol) in CH$_2$Cl$_2$ (10 mL) was treated with TFA (10 mL). After stirring at room temperature for 2 h, the solution was concentrated in vacuo. The resulting oil was treated with anhydrous HCl in dioxane (4 mL, 4.0 M) and sonicated until the oil was converted to a fine off-white solid. After stirring for 20 min, the suspension was concentrated. The solid was washed with Et$_2$O, isolated by filtration and dried under vacuum. Yield: 388 mg (quant); $^1$H NMR (400 MHz, CDCl$_3$) δ8.17 (s, 1H), 8.04 (s, 1H), 7.48 (d, J=16.0 Hz, 1H), 6.48 (d, J=16.0 Hz, 1H), 4.78 (bs, 1H), 3.90 (s, 2H), 2.99 (s, 2H), 2.79 (s, 2H), 2.58 (s, 3H); ESI MS m/z 298 $[C_{13}H_{15}N_3O_3+H]^+$ (E)-N-methyl-3-methyl-4-oxo-1,2,3,4,5,6-hexahydropyrido[2,3-b][1,5]diazocin-8-yl)-N-((3-methylbenzofuran-2-yl)methyl)acrylamide hydrochloride

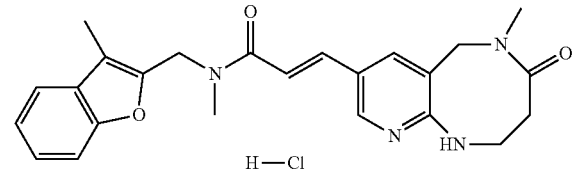 [SMILES: Cc1c(CN(C)C(=O)/C=C/c2cnc3c(c2)CN(C)C(=O)CCN3)oc2ccccc12 ; Cl]

EDC (116 mg, 0.61 mmol) was added to a suspension of (E)-3-(5-methyl-4-oxo-1,2,3,4,5,6-hexahydropyrido[2,3-b][1,5]diazocinn-8-yl)acrylic acid hydrochloride (150 mg, 0.50 mmol), HOBt (75 mg, 0.55 mmol), methyl-(3-methyl-benzofuran-2-ylmethyl)-amine (97 mg, 0.55 mmol) and (i-Pr)$_2$EtN (0.43 mL, 2.5 mmol) in DMF (8 mL). The mixture was allowed to stir for 18 h at 40° C. The mixture was cooled to room temperature and diluted with ethyl acetate (40 mL) and washed with water (50 mL) and brine (50 mL), dried over MgSO$_4$ and dried under high vacuum. The solid was then subjected to flash chromatography on silica gel using 5% methanol:dichloromethane to obtain 120 mg of yellow oil product. The product is redissolved in DCM followed by the addition of 1M HCl in diethyl ether (287 μL, 0.29 mmol) and sonicate for 5 min. Concentrate the suspension in vacuo to obtain the beige solid product Yield: 130 mg (57%): $^1$H NMR (400 MHz, CDCl$_3$) δ8.22 (bs, 1H), 7.65 (d, J=14.2 Hz, 1H), 7.50 (s, 1H), 7.41 (d, J=7.6 Hz, 1H), 7.25 (m, 2H), 7.03-6.79 (m, 1H), 5.22 (bm, 1H), 4.83 (s, 2H), 4.55 (s, 2H), 3.65 (q, J=7.6 Hz, 2H), 3.24 (s, 3H), 3.06 (t, J=7.2 Hz, 2H), 2.82 (s, 3H), 2.32 (s, 3H); ESI MS m/z 41.9 $[C_{24}H_{26}N_4O_3+H]^+$ Example 32

Preparation of (E)-N-(3-methoxy-2-propxybenzyl)-N-methyl-3-(5-methyl-4-oxo-1,2,3,4,5,6-hexahydropyrido[2,3-b][1,5]diazocin-8-yl)acrylamide

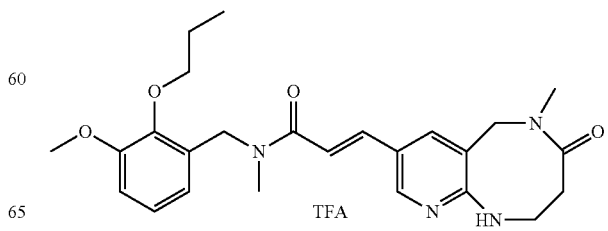

EDC (54 mg, 0.28 mmol) was added to a suspension of (E)-3-(5-methyl-4-oxo-1,2,3,4,5,6-hexahyydropyrido[2,3-b][1,5]diazocin-8-yl)acrylic acid hydrochloride (70 mg, 0.23 mmol), HOBt (34 mg, 0.25 mmol), (3-methoxy-2-propoxyphenyl)-N-methylmethanamine (52 mg, 0.25 mmol) and (i-Pr)₂EtN (0.20 mL, 1.2 mmol) in 5 mL of DMF;propionitrile (4:1). The mixture was allowed to stir for 17 h at 40° C. The mixture was cooled to room temperature and diluted with ethyl acetate (40 mL) and washed with water (50 mL) and NaHCO₃ (50 mL), dried over MgSO₄ and dried under high vacuum. The solid was then subjected to purification on Prep HPLC to obtain the product as a fluffy white solid. Yield 64 mg (62%); ¹H NMR (400 MHz, CDCl₃) δ7.87 (s, 1H), 7.73 (s, 1H), 7.50 (m, 2H), 7.05 (m, 1H), 6.86 (m, 2H), 6.73 (d, J=7.6 Hz, 1H), 4.72 (s, 3H), 4.00 (m, 2H), 3.89 (s, 5H), 3.14 (m, 5H), 2.83 (s, 3H), 1.82 (q, J=6.8 Hz, 2H), 1.06 (t, J=7.6 Hz, 3H); ESI MS m/z 453 [C₂₅H₃₂N₄O₄+H]⁺

Example 33

Preparation of (E)-N-methyl-3-(5-methyl-4-oxo-1,2,3,4,5,6-hexahydropyrido[2,3-b][1,5]diazocin-8-yl)-N-((3-methylbenzo[b]thiophen-2-yl)methyl)acrylamide

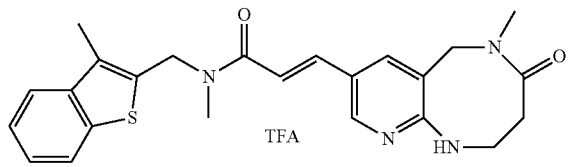 [SMILES: Cc1c(CN(C)C(=O)/C=C/c2cnc3c(c2)CN(C)C(=O)CCN3)sc2ccccc12]

EDC (54 mg, 0.28 mmol) was added to a suspension of (E)-3-(5-methyl-4-oxo-1,2,3,4,5,6-hexahydropyrido[2,3-b][1,5]diazocin-8-yl)acrylic acid hydrochloride (70 mg, 0.23 mmol), HOBt (34 mg, 0.25 mmol), N-methyl(3-methylbenzo[b]thiophen-2-yl)methanamine (48 mg, 0.25 mmol) and (i-Pr)₂EtN (0.20 mL, 1.2 mmol) in 5 mL of DME:propionitrile (4:1). The mixture was allowed to stir for 1 h at 40° C. The mixture was cooled to room temperature and diluted with ethyl acetate (40 mL) and washed with water (50 mL) and NaHCO₃ (50 mL), dried over MgSO₄ and dried under high vacuum. The solid was then subjected to purification on Prep HPLC to obtain the product as a fluffy white solid. Yield 54 mg (54%); ¹H NMR (400 MHz, CDCl₃) δ10.41 (bs, 1H), 8.08 (s, 1H), 7.79-7.68 (m, 3H), 7.59 (d, J=15.2 Hz, 1H), 7.40 (m, 2H), 6.95-6.86 (m, 1H), 4.96 (s, 2H), 4.72 (bs, 2H), 3.90 (s, 2H), 3.15 (m, 5H), 2.84 (s, 3H), 2.46 (s, 3H); ESI MS m/z 435 [C₂₄H₂₆N₄O₂S+H]⁺

Example 34

Preparation of (E)-3-(5-hydroxy-8-oxo-6,7,8,9-tetrahydro-5H-pyrido[2,3-b]azepin-3-yl)-N-methyl-N-((3-methylbenzofuran-2-yl)methyl)acrylamide (a) NBS, BPO, CHCl₃, reflux Preparation of 3-bromo-5-hydroxy-6,7-dihydro-5H-pyrido[2,3-b]zaepin-8(9H)-one Step A: A solution of benzoyl peroxide (46 mg, 0.189 mmol), N-bromosuccinimide (251 mg, 1.42 mmol), and 3-bromo-6,7-dihydro-5H-pyrido[2,3-]azepin-8(9H)-one (228 mg, 0.946 mmol) in 20 mL of chloroform is set at reflux temperature and stirred for 19 h. The reaction is then cooled to room temperature, diluted with 20 mL DCM, washed with water and saturated sodium bicarbonate, organic layer dried over magnesium sulphate, and concentrated in vacuo. The resulting crude product was purified via prep column HPLC to obtain 150 mg of white powder product (>90% pure). A second prep HPLC afforded the pure compound as a fluffy white solid. Yield 46 mg (15%); ¹H: NMR (400 MHz, CDCl₃) δ7.95 (s, 1H), 7.84 (s, 1H), 5.46 (m, 1H), 2.79-2.72 (m, 3H), 2.30 (m, 1H), 2.02 (s, 1H); ESI MS m/z 257, 259 [C₉H₉N₂O₂Br+H]⁺

Preparation of (E)-3-(5-hydroxy-8-oxo-6,7,8,9-tetrahydro-5H-pyrido[2,3]azepin-3-yl)-N-methyl-N-((3-methylbenzofuran-2-yl)methyl)acrylamide

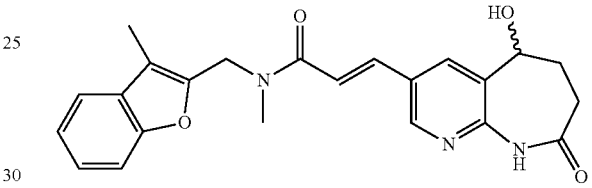

A suspension of 3-bromo-5-hydroxy-6,7-dihydro-5H-pyrido[2,3-b]azepin-8(9H)-one (40 mg, 0.16 mmol), N-methyl-N-(3-methylbenzofuran-2-yl)methyl)acrylamide (71 mg, 0.31 mmol) and (i-Pr)₂EtN (0.14 mL, 0.78 mmol) in 3 mL of DMF) was de-oxygenated with Ar for 30 min in a microwave reaction vial. The mixture was treated with Pd(OAc)₂ (4.0 mg, 0.02 mmol) and P(o-tol)₃ (9.0 mg, 0.04 mmol) then heated to 130° C. for 5 min in the microwave. The hot mixture was filtered through a pad of celite and washed liberally with ethyl acetate. The filtrate was diluted with 20 mL H₂O then extracted with 2×20 mL ethyl acetate. The resulting crude product was subjected to prep HPLC purification to yield 47 mg of product (75% pure). A seond prep HPLC purification was performed to obtain pure product as a fluffy white powder. Yield 5.1 mg (8%); ¹H NMR (400 MHz, CDCl₃) δ8.31 (s, 1H), 8.09 (s, 1H), 7.56 (d, J=7.4 Hz, 1H), 7.47 (m, 2H), 7.35-7.21 (m, 3H), 7.14 (d, J=15.2 Hz, 1H), 5.60 (s, 1H), 4.77 (s, 2H), 3.17 (s, 3H), 2.65 (s, 3H), 2.26 (m, 4H); ESI MS m/z 406 [C₂₃H₂₃N₃O₄+H]⁺

Example 35

Preparation of (E)-3-(1,2,3,4,5,6-hexahydropyrido[2,3-b][1,5]diazocin-8-yl)-N-methyl-N-((3-methylbenzofuran-2-yl)methyl)acrylamide

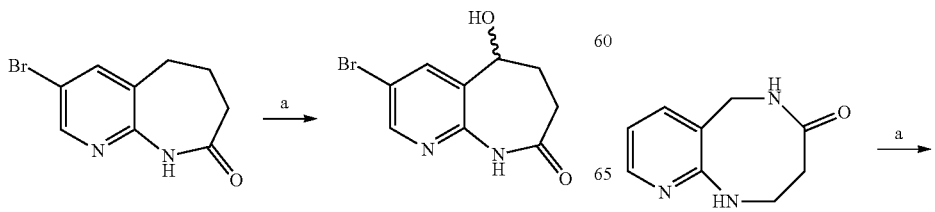

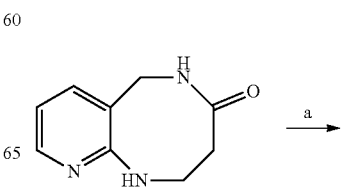

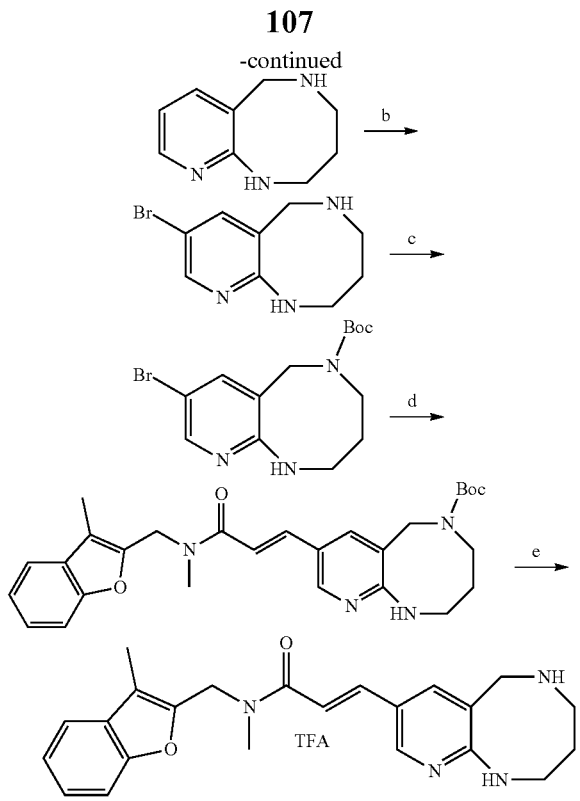

(a) LAH, THF, reflux, 20 h; (b) bromine, acetic acid, R.T., 20 h; (c) Boc$_2$O, DCM, R.T., 20 h; (d) R.H.S., Pd(OAc)$_2$, P(o-tol)$_3$, (i-Pr)$_2$EtN, DMF, 110° C., 20 h; (e) TFA, DCM, R.T., 1 h.

Preparation of 1,2,3,4,5,6-hexahydropyrido[2,3-b][1,5]diazocine

Step A: A solution of 2,3,5,6-tetrahydropyrido[2,3-b][1,5]diazocin-4(1H)-one (400 mg, 33.5 mmol) in 30 mL THF was added dropwise to 22.6 mL of a 1M solution of lithium aluminum hydride in THF at 0° C. The resulting solution was heated to reflux and allowed to stir for 24 h. The reaction was cooled to R.T. and the reaction was quenched with 1 mL of water, followed by 3 mL of 2M NaOH, and 3 mL water. The resulting slurry was poured through eelite and washed with 100 mL ethyl acetate. The filtrate was concentrated in vacuo to yield the pure product as a white solid. Yield 180 mg (49%); %); $^1$H NMR (400 MHz, CDCl$_3$) δ7.96 (d, J=5.2 Hz, 1H), 7.22 (d, J=7.6 Hz, 1H), 6.55 (m, 1H), 4.12 (s, 2H), 3.68 (t, J=6.0 Hz, 2H), 2.94 (m, 2H), 1.90 (m, 2H); ESI MS m/z 164 [C$_9$H$_{13}$N$_3$+H]$^+$ Preparation of 8-bromo-1,2,3,4,5,6-hexahydropyrido[2,3][1,5]diazocine Step B: Bromine (33 μL, 0.63 mmol) was added to a solution of 1,2,3,4,5,6-hexahydropyrido[2,3-b][1,5]diazocine (69 mg, 0.42 mmol) in 5 mL of acetic acid and stirred at room temperature for 19 h. Dilute with DCM and wash with saturated NaHCO$_3$, wash the organic layer with brine, separate, dry over MgSO$_4$, and concentrate in vacuo to obtain orange solid product. Yield 91 mg. (90%); $^1$H NMR (400 MHz, CDCl$_3$) δ8.05 (s, 1H), 7.54 (s, 1H), 4.44 (s, 2H), 3.68 (s, 2H), 3.33 (m, 2H), 2.05 (m, 2H); ESI MS m/z 242, 244 [C$_9$H$_{12}$N$_3$Br+H]$^+$ Preparation of tert-butyl 8-bromo-1,2,3,4-tetrahydropyrido[2,3-b][1,5]diazocine-5(6H)-carboxylate Step C: NEt$_3$ (0.04 mL, 0.30 mmol) was added to a solution of 8-bromo-1,2,3,4,5,6-hexahydropyrido[2,3-b][1,5]diazocine (55 mg, 0.23 mmol) in 3 mL of DCM under argon, followed by the addition of Boc$_2$O (57 mg, 0.25 mmol). The solution was stirred for 20 h and then concentrated to dryness in vacuo. The crude mixture was then subjected to flash column chromatography on Silica gel with a solvent system of 95:5 (DCM:2M NH$_3$ in methanol) to yield the pure product as a yellow oil. Yield 49 mg (64%); $^1$H NMR (400 MHz, CDCl$_3$) δ8.08 (s, 1H), 7.45 (s, 1H), 5.12 (bs, 1H), 4.43 (s, 2H), 3.46 (bs, 4H), 1.91 (bs, 2H), 137 (s, 9H); ESI MS m/z 342, 344 [C$_{12}$H$_{20}$N$_3$O$_2$Br+H]$^+$ Preparation of (E)-tert-butyl 8-(3-(methyl((3-methylbenzofuran-2-yl)methyl)amino)-3-oxoprop-1-enyl)-1,2,3,4-tetrahydropyrido[2,3-b][1,5]diazocine-5(6H)-carboxylate Step D: A suspension of tert-butyl 8-bromo-1,2,3,4-tetrahydropyrido[2,3-b][1,5]diazocine-5(6H)-carboxylate (45 mg, 0.13 mmol), N-methyl-N-((3-methylbenzofuran-2-yl)methyl)acrylamide (90 mg, 0.39 mmol) and (i-Pr)$_2$EtN (0.11 mL, 0.66 mmol) in 3.75 mL of DMF:propionitrile (4:1) was de-oxygenated with Ar for 30 min. The mixture was treated with Pd(OAc)$_2$ (3.0 mg, 0.013 mmol) and P(o-tol)$_3$ (8.0 mg, 0.926 mmol) then heated to 110° C. for 20 h. The hot mixture was filtered through a pad of celite and washed with ethyl acetate 2×20 mL. The filtrate was concentrated in vacuo to obtain crude brown oil product. The resulting crude product was subjected to prep HPLC purification to obtain pure product as an off-white solid. Yield 39 mg (60%); ESI MS m/z 491 [C$_{28}$H$_{34}$N$_4$O$_4$+H]$^+$ Preparation of (E)-3-(1,2,3,4,5,6-hexahydropyrido[2,3-b][1,5]diazocin-8-yl)-N-methyl-N-((3-methylbenzofuran-2-yl)methyl)acrylamide Step E: (E)-tert-butyl 8-(3-methyl((3-methylbenzofuran-2-yl)methyl)amino)-3-oxoprop-1-enyl)-1,2,3,4-tetrahyrdopyrido[2,3-b][1,5]diazocine-5(6H)-carboxylate (49 mg, 0.1 mmol) was dissolved in 5 mL of DCM followed by the addition of trifluoroacetic acid (5 mL). The solution was stirred for 1.5 h, then concentrated in vacuo, and subjected to prep HPLC purification to obtain the product as a white solid. Yield 25 mg (64%); $^1$H NMR (400 MHz, CDCl$_3$) δ10.1 (bs, 1H), 8.01 (m, 2H), 7.50-7.22 (m, 6H), 6.86 (d, J=160 Hz, 1H), 4.79 (s, 2H), 4.66 (s; 2H), 3.88 (s, 2H), 3.25 (s, 2H), 3.10 (s, 3H), 2.29 (bs, 5H); ESI MS m/z 391 [C$_{23}$H$_{26}$N$_4$O$_2$+H]$^+$ Example 36

Preparation of (E)-3-((E)-2,2-dimethyl-3-(methylimino)-3,4-dihydro-2H-pyrido[3,2-b][1,4]oxazin-7-yl)-N-methyl-N-((3-methylbenzofuran-2-yl)methyl)acrylamide hydrochloride

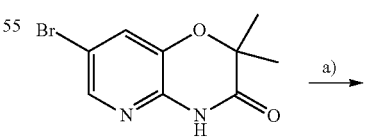

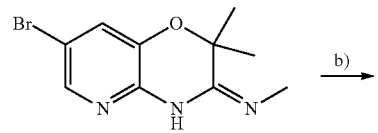

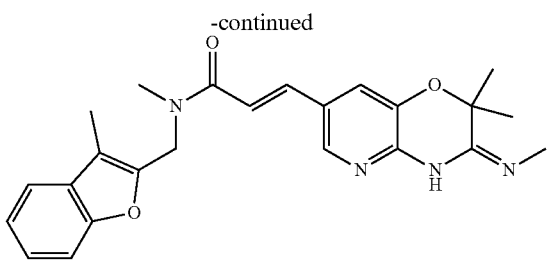

Reagents and conditions: a) PCl$_5$, μwave then NH$_2$Me, b) N-methyl-N-((3-methylbenzofuran-2-yl)methyl)acrylamide, DIPEA, Pd(OAc)$_2$, P(o-Tol)$_3$, DMF, then HCl.

a) (E)-N-(7-bromo-2,2-dimethyl-2H-pyrido[3,2-b][1,4]oxazin-3(4H)-ylidene)methanamine:

A dichloroethane (5 mL) solution of 7-bromo-2,2-dimethyl-2H-pyrido[3,2-b][1,4]oxazin-3(4H)-one (520 mg, 2 mmol) and phosphorus pentachloride (840 mg, 4 mmol) was irradiated in a microwave oven for 10 min at. 160° C. The solution was cooled to −78° C. and methylamine (2M in THF) was added it slowly until it became permanently basic. The mixture was diluted with CH$_2$Cl$_2$, washed with dilute solution of NaOH, dried, and evaporated. Crystallization from CH$_2$Cl$_2$/hexane afforded 480 mg (89%) of the title compound. $^1$H NMR (300 MHz, CDCl$_3$, δ) 8.07 (d, J=2.1 Hz, 1H), 7.21 (d, J=2.1 Hz, 1H), 4.9 (s, br, 1H), 3.06 (d, J=4.5 Hz, 3H), 1.46 (s, 6H). MS (ESI) m/e 270 (M+H)$^+$.

b) (E)-3-((E)-2,2-dimethyl-3-(methylimino)-3,4-dihydro-2H-pyrido[3,2-b][1,4]oxazin-7-yl)-N-methyl-N-((3-methyl-benzofuran-2-yl)methyl)acrylamide:

A DMF (3 mL) solution of (E)-N-(7-bromo-2,2-dimethyl-2H-pyrido[3,2-b][1,4]oxazin-3(4H)-ylidene)methanamine (271 mg, 1 mmol), N-methyl-N-((3-methylbenzofuran-2-yl)methyl)acrylamide (345 mg, 1.5 mmol) and diisopropylethylamine (0.52 mL, 3 mmol) was purged with Argon for 10 min. Pd(OAc)$_2$ (24 mg, 0.1 mmol) and P(o-tol)$_3$ (61 mg, 0.2 mmol) was added and then the Argon purge was repeated. The mixture was irradiated in a microwave oven for 10 min at 160° C. under Argon. Upon cooling, the mixture was diluted with water and extracted with EtOAc. The crude product was purified by chromatography (silica, 0-4% MeOH in CH$_2$Cl$_2$). The free base was turned into the HCl salt by addition of HCl (1 ml, 1M m Et$_2$O) to its CH$_2$Cl$_2$ solution and evaporation to afford 230 mg (55%) of the title compound, as a mixture of amide rotamers. $^1$H NMR (300 MHz, CDCl$_3$, δ, free base) 8.20 (s, 1H), 7.69 and 7.85 (2s, 1H), 7.5-6.7 (m, 6H), 5.14 (s, br, 1H), 4.83 and 4.71 (2s, 2H), 3.21 and 3.10 (2s, 3H), 3.09 (d, J=4.8 Hz, 3H), 2.31 (s, 3H), 1.49 (s, 6H). MS (ESI) m/e 419 (M+H)$^+$.

Example 37

Preparation of (E)-3-((E)-2,2-dimethyl-3-(methylimino)-3,4-dihydro-2H-pyrido[3,2-b][1,4]oxazin-7-yl)-N-methyl-N-((3-methylbenzo[b]thiophen-2-yl)methyl)acrylamide

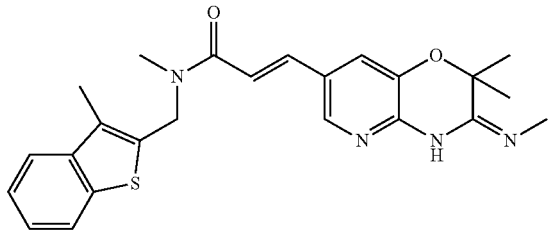 [SMILES: C/N=C1/Nc2ncc(/C=C/C(=O)N(C)Cc3sc4ccccc4c3C)cc2OC1(C)C]

A DMF (3 mL) Solution of (E)-N-(7-bromo-2,2-dimethyl-2H-pyrido[3,2-b][1,4]oxazin-3(4H)-ylidene)methanamine (271 mg, 1 mmol), N-methyl-N-((3-methylbenzofuran[b]thiophen-2-yl)methyl)acryl-ramide (367 mg, 1.5 mmol) and diisopropylethylamine (0.52 mL, 3 mmol) was purged with Argon for 10 min. Pd(OAc)$_2$ (24 mg, 0.1 mmol) and P(o-Tol)$_3$ (61 mg, 0.2 mmol) was added and then the Argon purge was repeated. The mixture was irradiated in a microwave oven for 10 min at. 160° C. under Argon. Upon cooling, the mixture was diluted with water and extracted with EtOAc. The crude product was purified by chromatography (silica, 0-4% MeOH in CH$_2$Cl$_2$). The free base was turned into the HCl salt by addition of HCl (1 mL, 1M in Et$_2$O) to its CH$_2$Cl$_2$ solution and evaporation to afford 287 mg (66%) of the title compound, as a mixture of amide rotamers. $^1$H NMR (300 MHz, CDCl$_3$, δ, free base) 8.21. (s, 1H), 7.8-7.6 (m, 3H), 7.4-7.2 (m, 3H), 6.9-6.7 (m, 1H), 5.30 (s, br, 1H), 4.95 and 4.88 (2s, 2H), 3.10 (m, 6H), 2.43 (s, 3H), 1.49 (s, 6H), MS (ESI) m/e. 435 (M+H)$^+$.

Example 38

E)-N-((1,3-dimethyl-1H-indol-2-yl)methyl)-N-methyl-3-(2-oxo-4-phenyl-2,3,4,5-tetrahydro-1H-pyrido[2,3-e][1,4]diazepin-7-yl)acrylamide

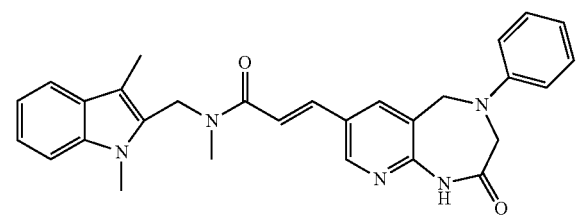 [SMILES: Cc1c(CN(C)C(=O)/C=C/c2cnc3c(c2)CN(c2ccccc2)CC(=O)N3)n(C)c2ccccc12]

A solution of N-((1,3-dimethyl-1H-indol-2-yl)methyl)-N-methylacrylamide (92 mg, 0.3 mmol) and DIPEA (0.16 mL, 0.9 mmol) in DMF (5 mL) was purged with argon for 10 min. Pd(oAC)$_2$ (6 mg, 0.03 mmol) and P(o-Tol)$_3$ (18 mg, 0.06 mmol) were added and the mixture was purged with argon and heated to 100° C. The crude mixture was filtered and water was added. The precipitate that formed was washed with ethyl acetate and dried to afford the title compound (144 mg, 74%). $^1$H NMR (400 MHz, DMSO-d$_6$) δ10.06-9.95 (rotamers, s, 1H), 8.32 (d, J=8.0 Hz, 2H), 7.57 (s, 1H), 7.50 (t, J=7.6 Hz, 2H), 7.38 (m, 3H), 7.12 (t, J=7.6 Hz, 2H), 7.03 (t, J=7.6 Hz, 1H), 6.84-6.35 (m, 2H), 4.90-4.80 (rotamers, s, 2H), 4.80 (s, 2H), 4.50 (s, 3H), 3.63 (s, 3H), 2.98 (s, 2H), 2.32 (s, 3H); MS (ESI): m/e 480.2 (C$_{29}$H$_{29}$N$_5$O$_2$+H)$^+$.

Example 39

(E)-N-methyl-N-((3-methylbenzofuran-2-yl)methyl)-3-(2,3,4,5-tetrahydro-1H-pyrido[2,3-b][1,4]diazepin-8-yl)acrylamide

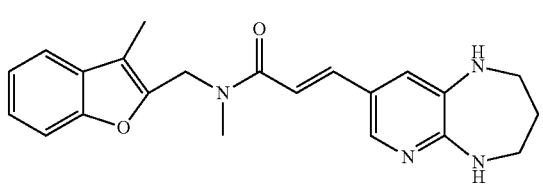

A solution of 8-bromo-2,3,4,5-tetrahydro-1H-pyrido[2,3-b][1,4]diazepin (0.15 g, 0.66 mmol), N-methyl-N-((3-methylbenzofuran-2-yl)methyl)acrylamide (0.30 g, 1.32 mmol), (i-Pr)$_2$EtN (0.34 mL, 2.0 mmol) tn DMF (7 mL) was de-oxygenated with Ar for 30 min. Pd(OAc)$_2$ (15 mg, 0.066 mmol) and P(o-tol)$_3$ (40 mg, 0.13 mmol) was added and the solution was de-oxygenated for an additional 15 min. The reaction was heated to 100° C. for 18 hrs at which time the reaction was cooled to room temperature and then filtered through a short-column of silica washing with EtOAc (20 mL). The filtrate was washed with brine (2×30 mL), dried (MgSO$_4$) and the solvent removed in vacuo. Purification by column chromatography (silica gel, CH$_2$Cl$_2$/MeOH, 99:1) gave the title compound (111 mg, 45%) as a yellow powder; $^1$H NMR (400 MHz, DMSO-d$_6$) δ7.75 (s, 1H), 7.56 (d, J=7.6 Hz, 1H), 7.48 (d, J=7.6, 1H), 7.43 and 7.39 (2×s, 1H), 7.35-7.22 (m, 3H), 7.08 and 6.82 (2×d, J=15, 1H), 6.22 (s, 1H), 5.25 (s, 1H), 4.90 and 478 (2×s, 2H), 3.14-2.93 (m, 7H), 2.26 (s, 3H), 1.68 (m, 2H); ESI MS m/z 377 [C$_{22}$H$_{24}$N$_4$O$_2$+H]$^+$ Example 40

(E)-N-((3-ethylbenzofuran-2-yl)methyl)-N-methyl-3-(8-oxo-6,7,8,9-tetrahydro-5H-pyrido[2,3-b]azepin-3-yl)acrylamide

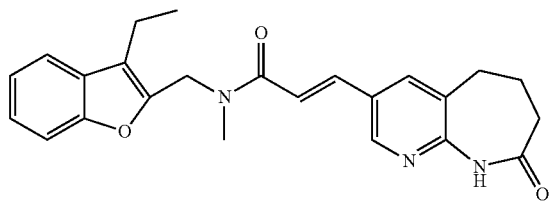 [SMILES: CCc1c(CN(C)C(=O)/C=C/c2cnc3c(c2)CCCC(=O)N3)oc2ccccc12]

Using methods described above the title compound was prepared. Purification by preparative HPLC (water/acetonitrile/0.05% TFA mixture) gave the title compound (70 mg, >95% by HPLC) as a white solid and a mixtare of amide rotomers: ESI MS m/z4o4 [C$_{24}$H$_{25}$N$_3$O$_3$+H]$^+$.

REFERENCES

All publications and patents oientioned herein, including those items listed below, are hereby incorporated by reference in their entirety as if each individual publication or patent was specifically and individually Incorporated by reference. In case of conflict, the present application, including any definitions herein, will control
Heath, et al. *Nature* 406; 145-2006; Bergler, et al, 1994, *J. Biol. Chem.* 269, 5493-5496; Heath, et al, 1996, *J. Biol. Chem.* 271, 1833-1836; Grassberger, et al, 1984 *J. Med Chem* 27 947-953; Turnowsky, et al, 1989, *J. Bacteriol.,* 171, 6555-6563; McMurry, et al, 1998 *Nature* 394, 531-532; Levy, et al, 1999 *Nature* 398, 383-384; Ward, et al, 1999 *Biochem.* 38, 12514-12525; Heck, *Org. Reactions* 1982, 27, 345; *J. Het. Chem.*, 1978, 15, 249-251; Morb. Mortal Wkly Rep. 1998; 46:71-80; Standards, N.C.f.C.L., Methods for Dilution Antimicrobial Susceptibility Tests for Bacteria that Grow Aerobically; Approved Standard—Fifth Edition. 2000; Baxter, D. F., et al., A novel membrane potential-sensitive fluorescent dye improves cell-based assays for ion channels. J Biomol Screen, 2002 7(1): p. 79-85; Ahmed, S. A., R. M. Gogal, Jr., and J. E. Walsh, A new rapid and simple non-radioactive assay to monitor and determine the proliferation of lymphocytes: an alternative to [3H]thyrmidine incorporation assay, J Immunol Methods, 1994 170(2): p. 211-24; http://bbrp.lln-l.gov/bbrp/html/microbe.html; http://artedi.ebc.uu.se/Projects/Francisella/; U.S. patent application Ser. Nos. 08/790,043; 10/009,219, 10/089,019; 09/968,129; 09/968,123; 09/968,236; 09/959,372; 09/979,560; 09/980,369; 10/089,755; 10/089,739; 10/089,740; PCT Application Nos. PCT/US03/38706; WO 0027628; WO 0210332; U.S. Provisional Application Nos. 60/431,406; 60/465,583; U.S. Pat. Nos. 6,531,126; 6,527,759; 6,518,270; 6,518,239; 6,517,827; 6,461,829; 6,448,054; 6,423,341; 6,495,351; 6,486,149; 6,441,162; 6,436,980; 6,399,629; 6,518,263; 6,503,881; 6,503,881; 6,486,148; 6,465,429; 6,388,070; 6,531,649; 6,531,465; 6,528,089; 6,521,408; 6,518,487; 6,531,508; 6,514,962; 6,503,953; 6,492,351; 6,486,148; 6,461,607; 6,448,054; 6,495,161; 6,495,158; 6,492,351; 6,486,165; 6,531,465; 6,514,535; 6,489,318; 6,497,886; 6,503,953; 6,503,539; 6,500,459; 6,492,351; 6,500,463; 6,461,829; 6,448,238; 6,432,444; 6,333,045; 6,291,462; 6,221,859; 6,514,986; 6,340,689; 6,309,663; 6,303,572; 6,277,836; 6,367,985; 6,468,964; 6,461,607; 6,448,449; 6,436,980; 6,423,741; 6,406,8805 6,395,746; 6,346,391; 6,294,192; 6,267,985; 6,235,908; 6,515,113; 6,509,327; 6,593,955; 6,525,066; 6,531,291; 6,517,827; 6,514,953; 6,514,541; 6,428,579; 6,451,339; 6,461,607; 6,461,829; 6,503,906; 6,518,239; 6,133,260; 6,174,878; 6,184,380; 6,187,341; 6,194,429; 6,194,441; 6,198,000; 6,221,859; 6,221,864; 6,239,113; 6,239,141; and 6,248,363.

EQUIVALENTS

While specific embodiments of the subject invention have been discussed, the above specification is illustrative and not restrictive. Many variations of the invention will become apparent to those skilled in the art upon review of this specification. The full scope of the invention should be detennined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound of formula I:

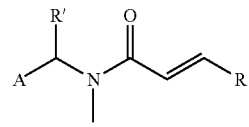

wherein, independently for each occurrence,

A is a monocyclic ring of 4-7 atoms containing 0-2 heteroatoms, a bicyclic ring of 8-12 atoms containing 0-4 heteroatoms or a tricyclic ring of 8-12 atoms containing 0-6 heteroatoms wherein the rings are independently aliphatic, aromatic, heteroaryl or heterocyclic in nature, the heteroatoms are selected from the group consisting of N, S, and O, and the rings are optionally substituted with one or more groups selected from the group consisting of C$_{1-4}$ alkyl, OR", CN, OCF$_3$, F, Cl, Br, and I;

wherein R" is selected from the group consisting of H, alkyl, aralkyl, and heteroaralkyl, wherein the heteroaryl group of the heteroaralkyl is a 3-10 membered ring structure containing 1-4 heteroatoms selected from the group consisting of N, S, and O;

R' is selected from the group consisting of H and alkyl;

R is selected from the group consisting of:

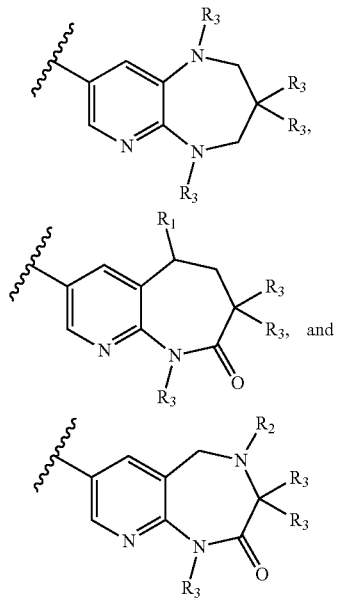

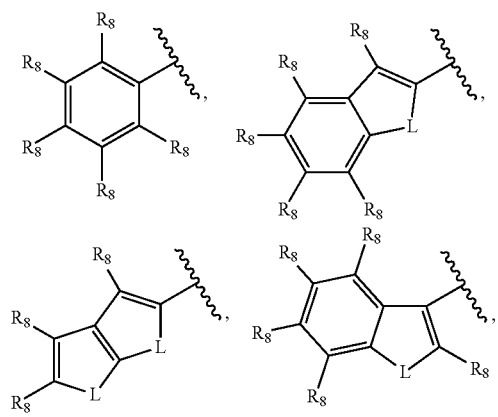

wherein, independently for each occurrence,
R$_1$ is OH;
R$_2$ is OH; and
R$_3$ is selected from the group consisting of H, alkyl, carbonyl, sulfonyl, or aryl;
or a pharmaceutically acceptable salt thereof; wherein:
carbonyl is —C(O)—X$^{50}$—R$^{55}$ or —X$^{50}$—C(O)—R$^{56}$, where X$^{50}$ is a bond, oxygen, or sulfur; R$^{55}$ and R$^{56}$ are hydrogen, alkyl, alkenyl, or —(CH$_2$)$_m$—R$^{61}$; R$^{61}$ is aryl, cloalkyl, cycloalkenyl, or heterocyclyl; and m is zero or an integer in the range of 1 to 8; and sulfonyl is —S(O)$_2$—R$^{58}$, where R$^{58}$ is alkyl, alkenyl, alkenyl, cycloalkyl, heterocyclyl, aryl, or hetero aryl.

2. The compound of claim 1, wherein A is selected from the group consisting of:

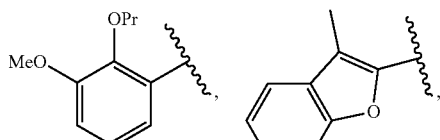

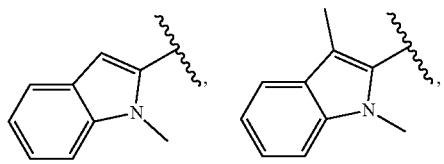

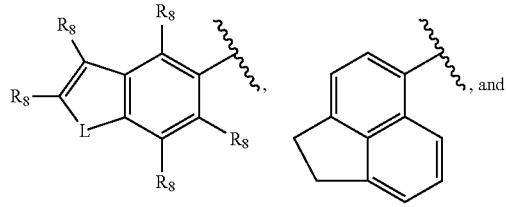

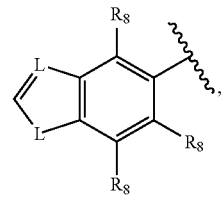

wherein, independently for each occurrence,
R$_8$ is selected from the group consisting of H, C$_{1-4}$ alkyl, C$_{1-4}$ haloalkyl, C$_{1-4}$ alkenyl, OR", CN, OCF$_3$, F, Cl, Br, and I; wherein R" is selected from the group consisting of H, alkyl, aralkyl, and heteroaralkyl; and L is selected from the group consisting of O, S, and NR$_3$.

3. The compound of claim 1, wherein A is selected from the group consisting of:

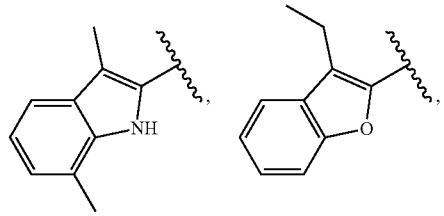

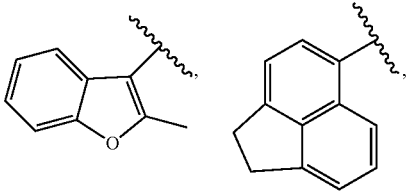

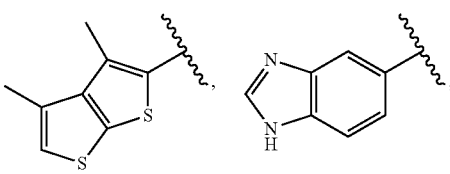

-continued

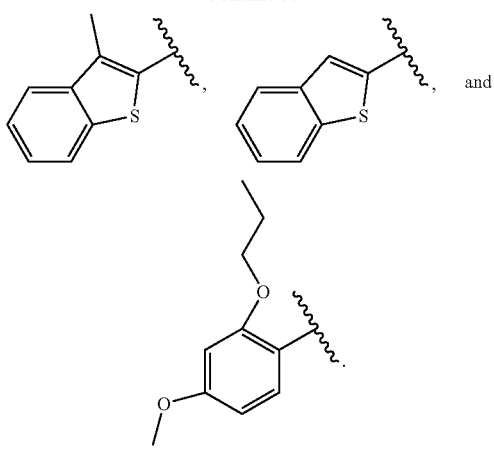

4. A compound of formula Ia:

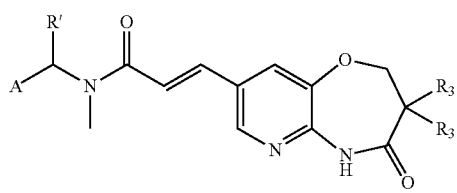

wherein, independently for each occurrence,

A is a bicyclic ring of 8-12 atoms containing 0-4 heteroatoms or a tricyclic ring of 8-12 atoms containing 0-6 heteroatoms wherein the rings are independently aliphatic, aromatic, heteroaryl or heterocyclic in nature, the heteroatoms are selected from the group consisting of N, S, and O, and the rings are optionally substituted with one or more groups selected from the group consisting of $C_{1-4}$ alkyl, OR", CN, OCF$_3$, F, Cl, Br, and I; wherein R" is selected from the group consisting of H, alkyl, aralkyl, and heteroaralkyl, wherein the heteroaryl group of the heteroaralkyl is a 3-10 membered ring structure containing 1-4 heteroatoms selected from the group consisting of N, S, and O;

R' is selected from the group consisting of H and alkyl;

wherein, independently for each occurrence, $R_3$ is selected from the group consisting of H, alkyl, carbonyl, sulfonyl, and aryl; or a pharmaceutically acceptable salt thereof; wherein:

carbonyl is —C(O)—$X^{50}$—$R^{55}$ or —$X^{50}$—C(O)—$R^{56}$, where $X^{50}$ is a bond, oxygen, or sulfur; $R^{55}$ and $R^{56}$ are hydrogen, alkyl, alkenyl, or —(CH$_2$)$_m$—$R^{61}$; $R^{61}$ is aryl, cycloalkyl, cycloalkenyl, or heterocyclyl; and m is zero or an integer in the range of 1 to 8; and sulfonyl is —S(O)$_2$—$R^{58}$, where $R^{58}$ is alkyl, alkenyl, alkynyl, cycloalkyl, heterocyclyl, aryl, or hetero aryl.

5. The compound of claim 4, wherein the compound has formula Ib:

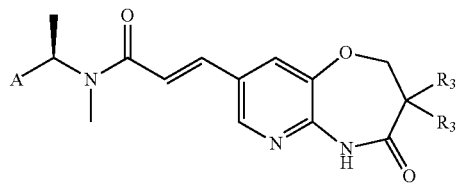

wherein,

A is

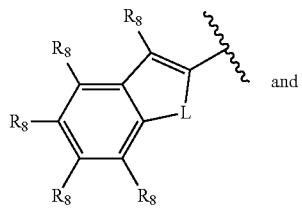

wherein, independently for each occurrence, $R_8$ is selected from the group consisting of H, $C_{1-4}$ alkyl, $C_{1-4}$ haloalkyl, $C_{1-4}$ alkenyl, OR", CN, OCF$_3$, F, Cl, Br, and I; wherein R" is selected from the group consisting of H, alkyl, aralkyl, and heteroaralkyl; and L is selected from the group consisting of O, S, and NR$_3$.

6. The compound of claim 2, wherein the compound has formula Ic:

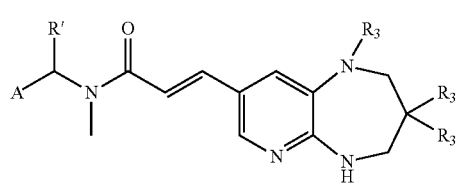

wherein A is:

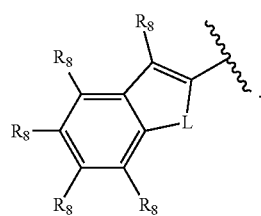

7. The compound of claim 2, wherein the compound has formula Im:

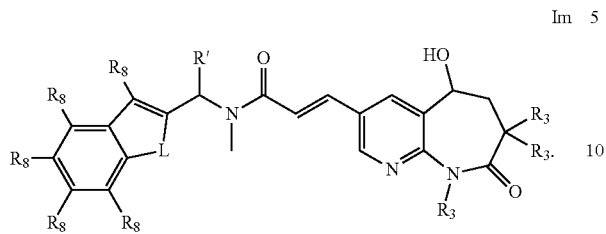

8. The compound of claim 2, wherein the compound has formula In:

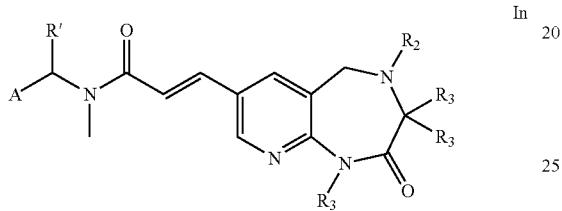

wherein A is

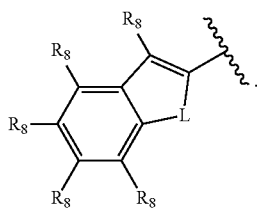

9. A compound of formula Io:

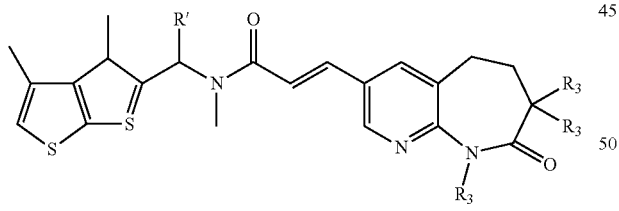

wherein:
R' is selected from the group consisting of H and alkyl;
$R_3$ is, independently for each occurrence, selected from the group consisting of H, alkyl, carbonyl, sulfonyl, and aryl; or a pharmaceutically acceptable salt thereof; wherein:
carbonyl is —C(O)—$X^{50}$—$R^{55}$ or —$X^{50}$—C(O)—$R^{56}$, where $X^{50}$ is a bond, oxygen, or sulfur; $R^{55}$ and $R^{56}$ are hydrogen, alkyl, alkenyl, or —(CH$_2$)$_m$—$R^{61}$; $R^{61}$ is aryl, cycloalkyl, cycloalkenyl, or heterocyclyl; and m is zero or an integer in the range of 1 to 8; and
sulfonyl is —S(O)$_2$—$R^{58}$, where $R^{58}$ is alkyl, alkenyl, alkenyl, cycloalkyl, heterocyclyl, aryl, or hetero aryl.

10. A compound selected from the group consisting of:
(R,E)-(3,3-dimethyl-4-oxo-2,3,4,5-tetrahydropyrido[3,2-b][1,4]oxazepin-8-yl)-N-(1(3-ethylbenzofuran-2-yl)ethyl)-N-methylacrylamide;
(E)-N-((1,3-dimethyl-1H-indol-2-yl)methyl)-N-methyl-3-(2-oxo-4-phenyl-2,3,4,5-tetrahydro-1H-pyrido[2,3-e][1,4]diazepin-7-yl)acrylamide; and
(E)-N-((3-ethylbenzofuran-2-yl)methyl)-N-methyl-3-(8-oxo-6,7,8,9-tetrahydro-5H-pyrido[2,3-b]azepin-3-yl)acrylamide, and pharmaceutically acceptable salts thereof.

11. A pharmaceutical composition comprising a compound of claim 1 and a pharmaceutically acceptable carrier or excipient.

12. The composition of claim 11, wherein the composition is formulated for one of: intraveneous administration, injectable administration, topical application, as a suppository, or systemic administration.

13. The composition of claim 11, wherein the composition is formulated for oral administration.

14. A method of treating a subject with a bacterial infection comprising administering to the subject the pharmaceutical composition of claim 11.

15. The method of claim 14, wherein the compound inhibits the Fab I activity of a microbe with an IC$_{50}$ at least 1 order of magnitude lower than the IC$_{50}$ for inhibiting enoyl CoA hydratase of a mammal.

16. The method of claim 15, wherein the mammal is a human.

17. A method of disinfecting an inanimate surface comprising administering to the inanimate surface a compound of claim 1.

18. A kit comprising the pharmaceutical composition of claim 11 and instructions for use thereof.

19. A pharmaceutical composition comprising a compound of claim 4 and a pharmaceutically acceptable carrier or excipient.

20. A pharmaceutical composition comprising a compound of claim 9 and a pharmaceutically acceptable carrier or excipient.

* * * * *